United States Patent
Papagiannakopoulos

(10) Patent No.: US 12,186,377 B2
(45) Date of Patent: Jan. 7, 2025

(54) MODULATION OF OXIDATIVE STRESS AND AMINO ACID METABOLISM FOR THE TREATMENT OR PREVENTION OF DISEASES AND DISORDERS

(71) Applicant: NEW YORK UNIVERSITY, New York, NY (US)

(72) Inventor: Thales Papagiannakopoulos, Brooklyn, NY (US)

(73) Assignee: New York University, New York, NY (US)

( * ) Notice: Subject to any disclaimer, the term of this patent is extended or adjusted under 35 U.S.C. 154(b) by 704 days.

(21) Appl. No.: 17/029,237

(22) Filed: Sep. 23, 2020

(65) Prior Publication Data

US 2021/0085763 A1   Mar. 25, 2021

Related U.S. Application Data

(60) Provisional application No. 62/904,256, filed on Sep. 23, 2019.

(51) Int. Cl.
| | |
|---|---|
| A61K 38/00 | (2006.01) |
| A61K 31/4164 | (2006.01) |
| A61K 31/554 | (2006.01) |
| A61K 33/26 | (2006.01) |
| A61K 38/44 | (2006.01) |
| A61K 38/50 | (2006.01) |
| A61K 38/51 | (2006.01) |
| A61P 35/00 | (2006.01) |

(52) U.S. Cl.
CPC .......... *A61K 38/51* (2013.01); *A61K 31/4164* (2013.01); *A61K 31/554* (2013.01); *A61K 33/26* (2013.01); *A61K 38/443* (2013.01); *A61K 38/50* (2013.01); *A61P 35/00* (2018.01)

(58) Field of Classification Search
CPC ................ A61K 38/51; A61K 31/4164; A61K 31/554; A61K 33/26; A61K 38/443; A61K 38/50; A61P 35/00
See application file for complete search history.

(56) References Cited

U.S. PATENT DOCUMENTS

2011/0136246 A1* 6/2011 Shibata .................... A61P 43/00
530/389.1
2016/0061841 A1* 3/2016 Mine ...................... A61K 35/13
435/7.1

OTHER PUBLICATIONS

Briggs et al., "Paracrine Induction of HIF by Glutamate in Breast Cancer: EgIN1 Senses Cysteine," Cell. Jun. 30, 2016;166(1):126-39.
Cronin et al., "Annual Report to the Nation on the Status of Cancer, part I: National cancer statistics," Cancer. Jul. 1, 2018; 124(13):2785-2800.
Davidson et al., "Environment Impacts the Metabolic Dependencies of Ras-Driven Non-Small Cell Lung Cancer," Cell Metab. Mar. 8, 2016;23(3):517-28.
Davies et al., "Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery," 2016, Journal of medicinal chemistry 59, 3991-4006.
DeBerardinis et al., "Beyond aerobic glycolysis: transformed cells can engage in glutamine metabolism that exceeds the requirement for protein and nucleotide synthesis", Proc Natl Acad Sci U S A. Dec. 4, 2007;104(49):19345-50.
DeNicola et al., "NRF2 regulates serine biosynthesis in non-small cell lung cancer," Nat Genet. Dec. 2015;47(12):1475-81.
DeNicola et al., "Oncogene-induced Nrf2 transcription promotes ROS detoxification and tumorigenesis," Nature. Jul. 6, 2011;475(7354):106-9.
Dixon et al., "Pharmacological inhibition of cystine-glutamate exchange induces endoplasmic reticulum stress and ferroptosis," Elife. May 20, 2014;3:e02523.
Fox et al., "NRF2-dependent metabolic reprogramming is required for tumor recurrence following oncogene inhibition," 2019, bioRxiv, 513994.
Garcia-Bermudez et al., "Aspartate is a limiting metabolite for cancer cell proliferation under hypoxia and in tumours," Nat Cell Biol. Jul. 2018;20(7):775-781.
Griffith and Meister, "Potent and specific inhibition of glutathione synthesis by buthionine sulfoximine (S—n-butyl homocysteine sulfoximine)," J Biol Chem. Aug. 25, 1979;254(16):7558-60.
Gwinn et al., "Oncogenic KRAS Regulates Amino Acid Homeostasis and Asparagine Biosynthesis via ATF4 and Alters Sensitivity to L-Asparaginase," Cancer Cell. Jan. 8, 2018;33(1):91-107.e6.
Hanahan and Weinberg, "Hallmarks of cancer: the next generation," Cell. Mar. 4, 2011;144(5):646-74.
Heiden and DeBerardinis, "Understanding the Intersections between Metabolism and Cancer Biology," Cell. Feb. 9, 2017;168(4):657-669.
Knott et al., "Asparagine bioavailability governs metastasis in a model of breast cancer," Nature. Feb. 15, 2018;554(7692):378-381.
Koppula et al., "The glutamate/cystine antiporter SLC7A11/xCT enhances cancer cell dependency on glucose by exporting glutamate," J Biol Chem. Aug. 25, 2017;292(34):14240-14249.
Larson et al., Molecular mechanisms contributing to glutamine-mediated intestinal cell survival, Am J Physiol Gastrointest Liver Physiol. Dec. 2007;293(6):G1262-71.
Lewis et al., "Tracing compartmentalized NADPH metabolism in the cytosol and mitochondria of mammalian cells," Mol Cell. Jul. 17, 2014;55(2):253-63.
Maddocks et al., "Modulating the therapeutic response of tumours to dietary serine and glycine starvation," Nature. Apr. 19, 2017;544(7650):372-376.

(Continued)

*Primary Examiner* — Jeanette M Lieb
(74) *Attorney, Agent, or Firm* — Riverside Law LLP

(57) ABSTRACT

The present invention relates methods for treating cancer by comprising administering to the subject an agent for reducing at least one NEAA, inhibiting the PPP pathway, inhibiting the sorbitol pathway, inhibiting heme biosynthesis, or any combination thereof. The invention also includes methods of treating cancer comprising detecting a tumor as having increased ROS administering to the subject an agent for reducing at least one NEAA, inhibiting the PPP pathway, inhibiting the sorbitol pathway or inhibiting heme biosynthesis, or any combination thereof.

2 Claims, 55 Drawing Sheets

(56) References Cited

OTHER PUBLICATIONS

Maddocks et al., "Serine starvation induces stress and p53-dependent metabolic remodelling in cancer cells," Nature. Jan. 24, 2013;493(7433):542-6.

Mehrmohamadi and Locasale, "Context dependent utilization of serine in cancer," Mol Cell Oncol. Oct. 1, 2015;2(4):e996418.

Meylan et al., "Requirement for NF-kappaB signalling in a mouse model of lung adenocarcinoma," Nature. Nov. 5, 2009;462(7269):104-7.

Mitsuishi et al., "Nrf2 redirects glucose and glutamine into anabolic pathways in metabolic reprogramming," Cancer Cell. Jul. 10, 2012;22(1):66-79.

Muir et al., "Environmental cystine drives glutamine anaplerosis and sensitizes cancer cells to glutaminase inhibition," Elife. Aug. 15, 2017;6:e27713.

Nicklin et al., "Bidirectional transport of amino acids regulates mTOR and autophagy," Cell. Feb. 6, 2009;136(3):521-34.

Rhoads et al., "L-glutamine stimulates intestinal cell proliferation and activates mitogen-activated protein kinases," Am J Physiol. May 1997;272(5 Pt 1):G943-53.

Richards and Kilberg, "Asparagine synthetase chemotherapy," Annu Rev Biochem. 2006;75:629-54.

Romero et al., "Keap1 loss promotes Kras-driven lung cancer and results in dependence on glutaminolysis," Nat Med. Nov. 2017;23(11):1362-1368.

Sayin et al., "Activation of the NRF2 antioxidant program generates an imbalance in central carbon metabolism in cancer," Elife. Oct. 2, 2017;6:e28083.

Shin et al., "The glutamate/cystine xCT antiporter antagonizes glutamine metabolism and reduces nutrient flexibility," Nat Commun. Apr. 21, 2017;8:15074.

Storck et al., "Structure, expression, and functional analysis of a Na(+)-dependent glutamate/aspartate transporter from rat brain," Proc Natl Acad Sci U S A. Nov. 15, 1992;89(22):10955-9/.

Tsun and Possemato, "Amino acid management in cancer," Semin Cell Dev Biol. Jul. 2015;43:22-32.

Urig and Becker, "On the potential of thioredoxin reductase inhibitors for cancer therapy," Semin Cancer Biol. Dec. 2006;16(6):452-65.

Vander Heiden et al., "Understanding the Warburg effect: the metabolic requirements of cell proliferation," Science. May 22, 2009;324(5930):1029-33.

Wang et al., "Dimethyl Fumarate Protects Neural Stem/Progenitor Cells and Neurons from Oxidative Damage through Nrf2-ERK1/2 MAPK Pathway," Int J Mol Sci. Jun. 17, 2015;16(6):13885-907.

Watanabe and Bannai, "Induction of cystine transport activity in mouse peritoneal macrophages," J Exp Med. Mar. 1, 1987;165(3):628-40.

Yang and Vousden, "Serine and one-carbon metabolism in cancer," Nat Rev Cancer. Oct. 2016; 16(10):650-62.

\* cited by examiner

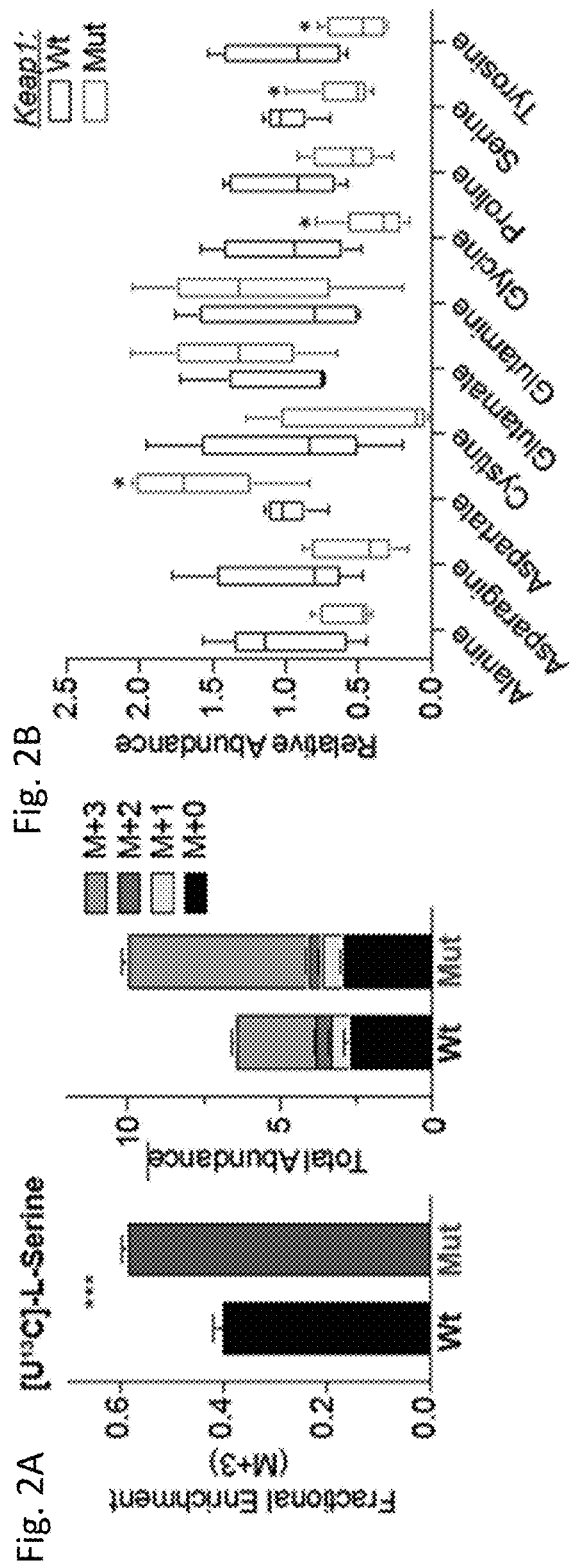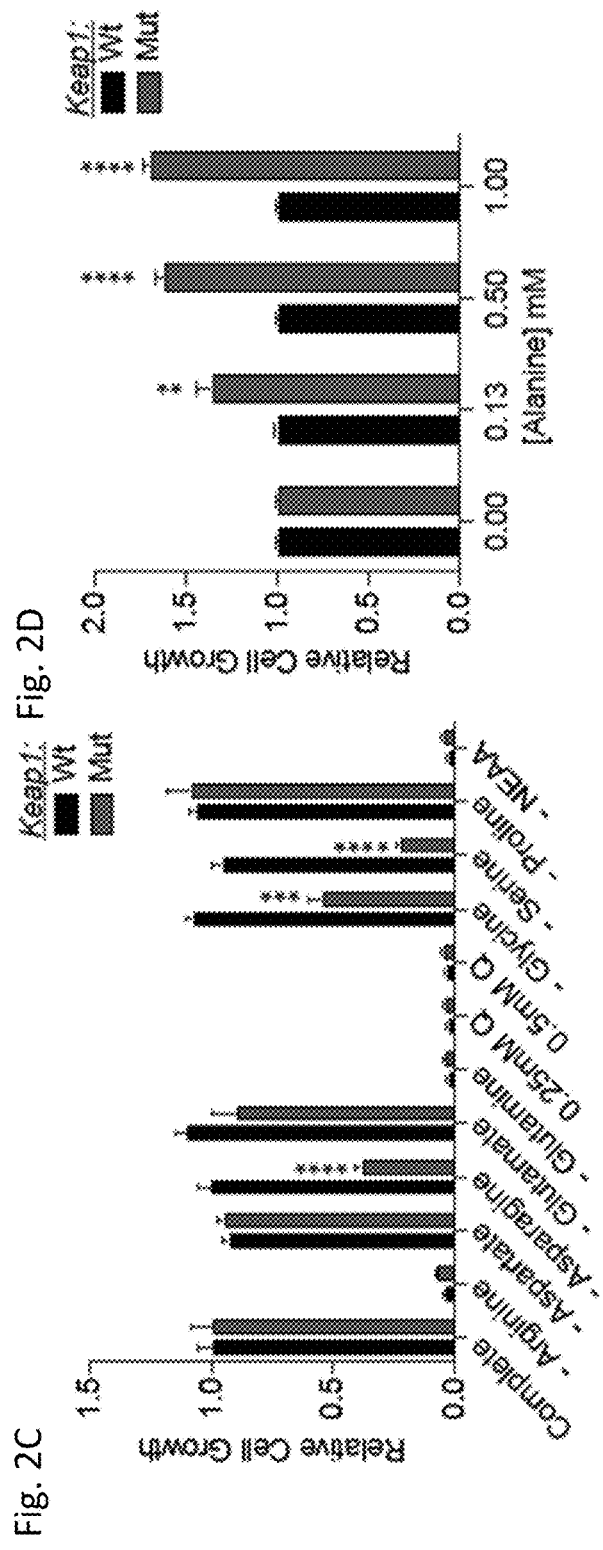

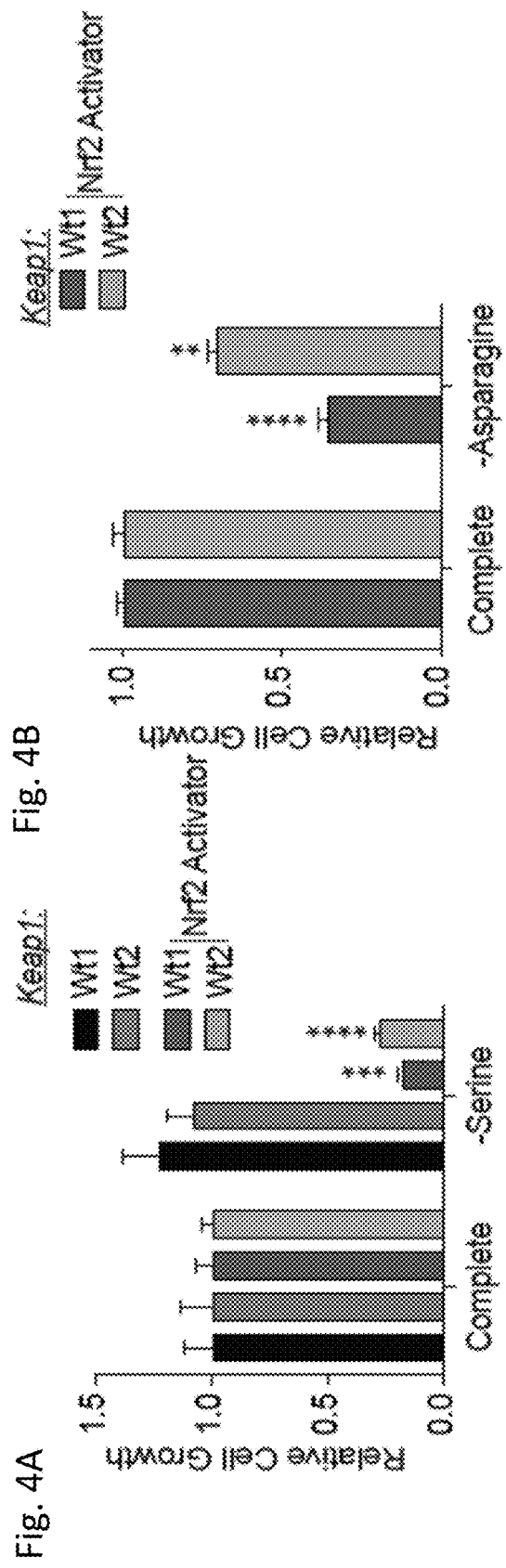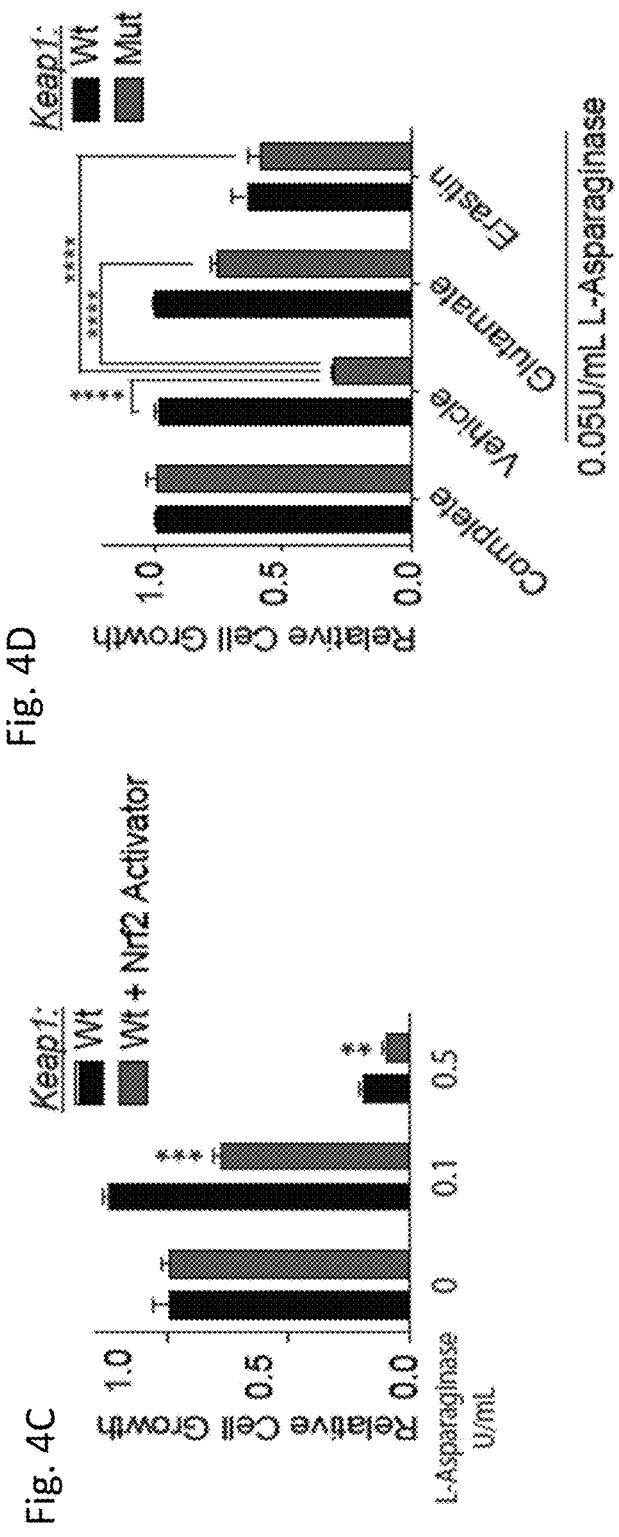
Fig. 4A, Fig. 4B, Fig. 4C, Fig. 4D

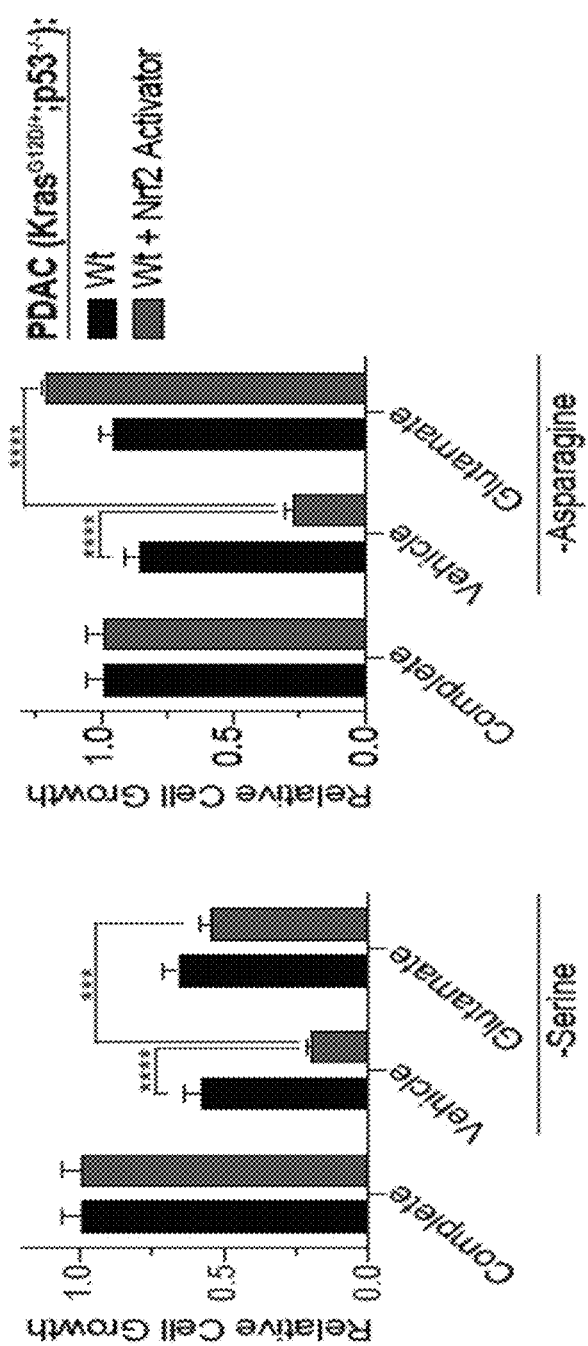
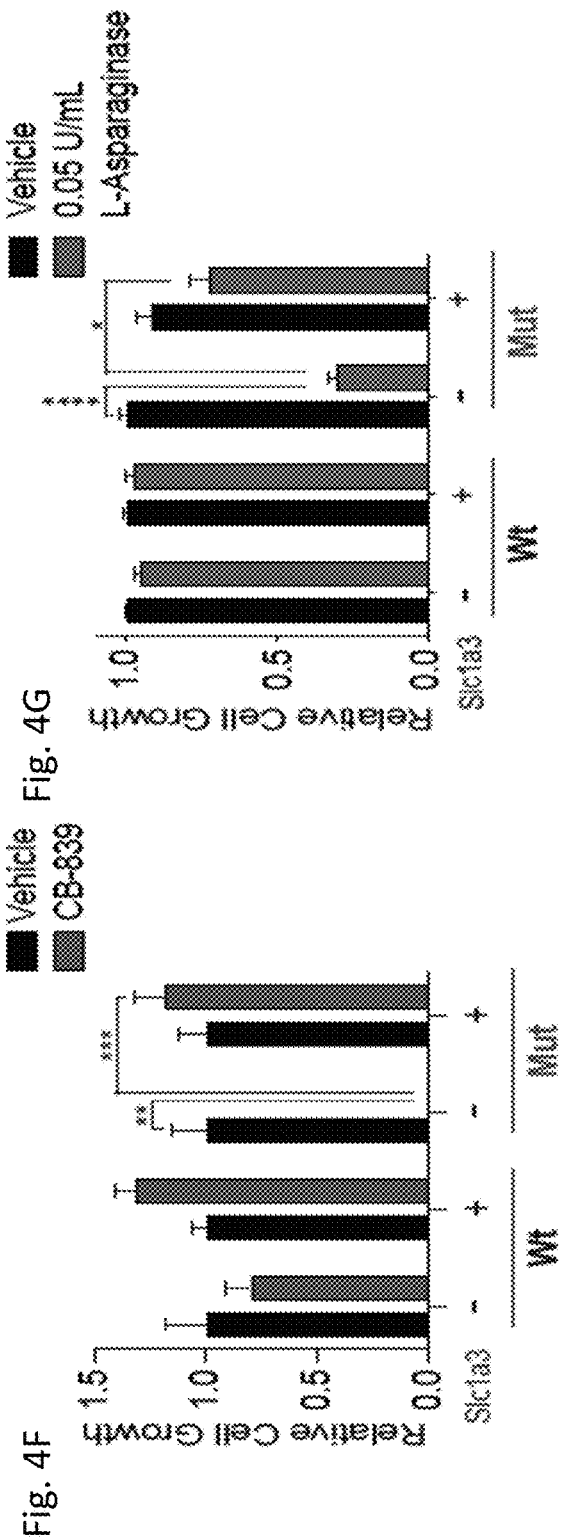
Fig. 4E
Fig. 4F
Fig. 4G

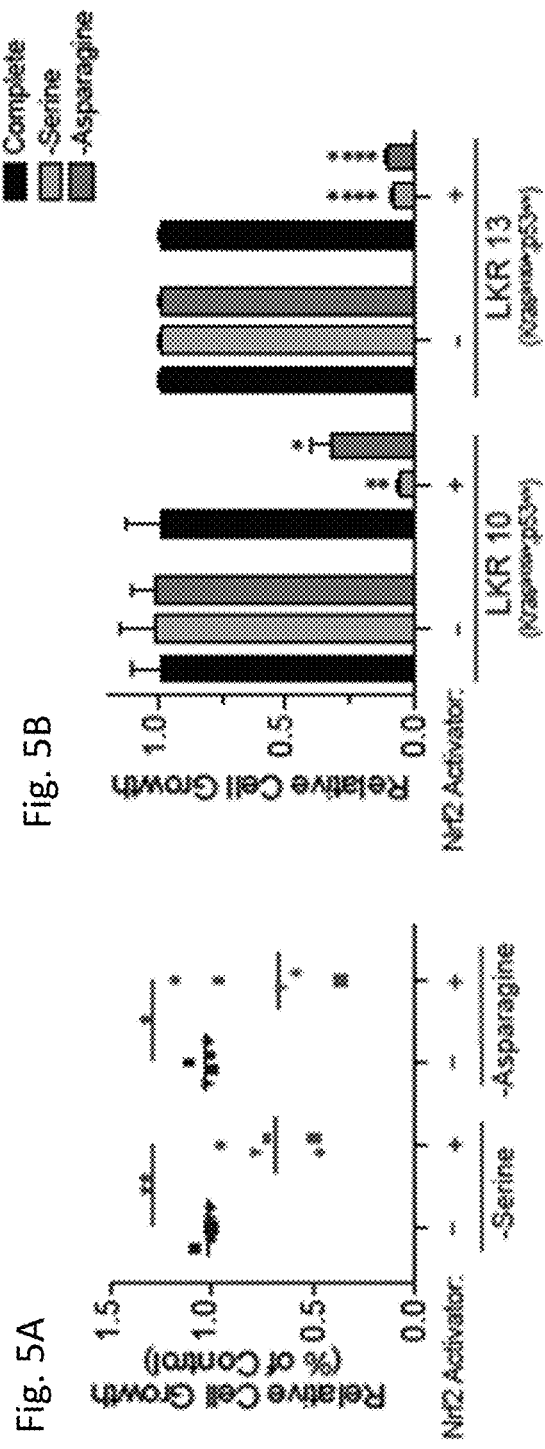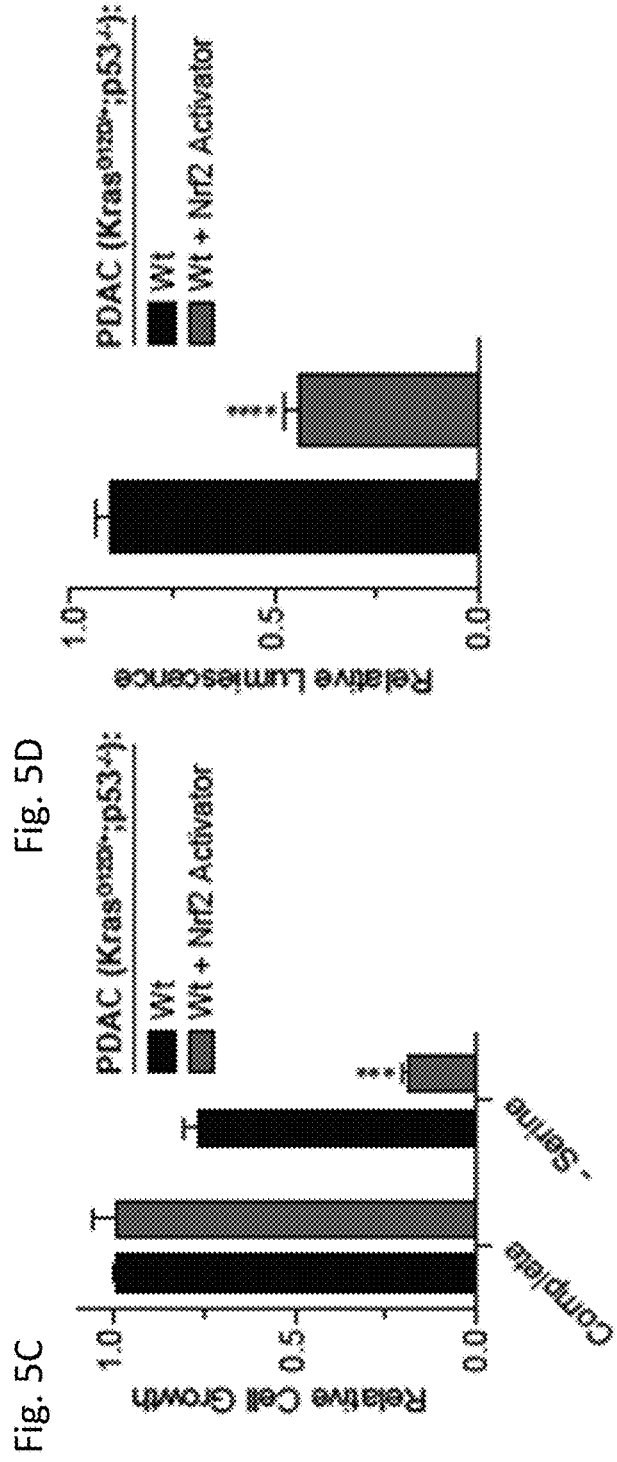

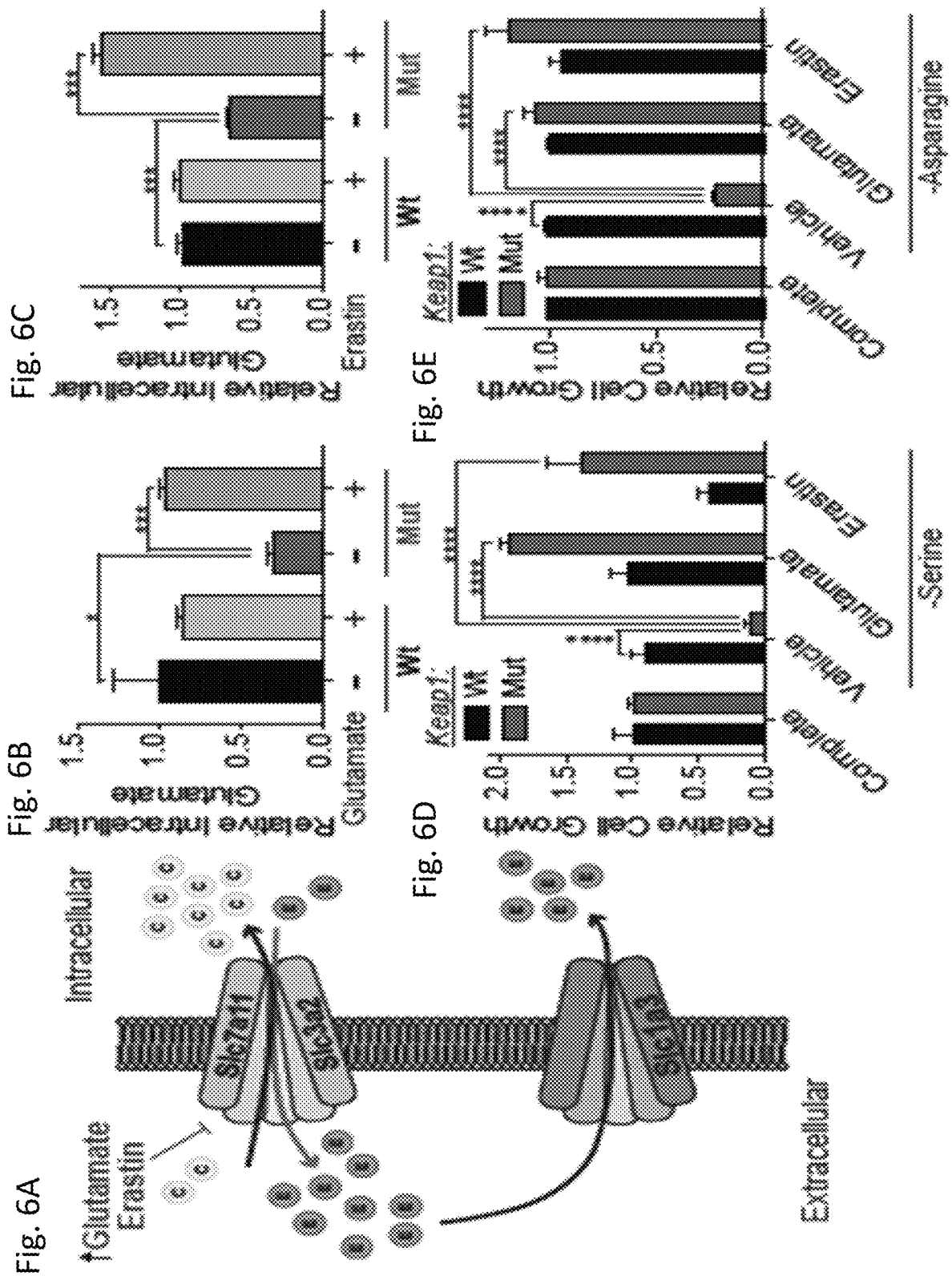

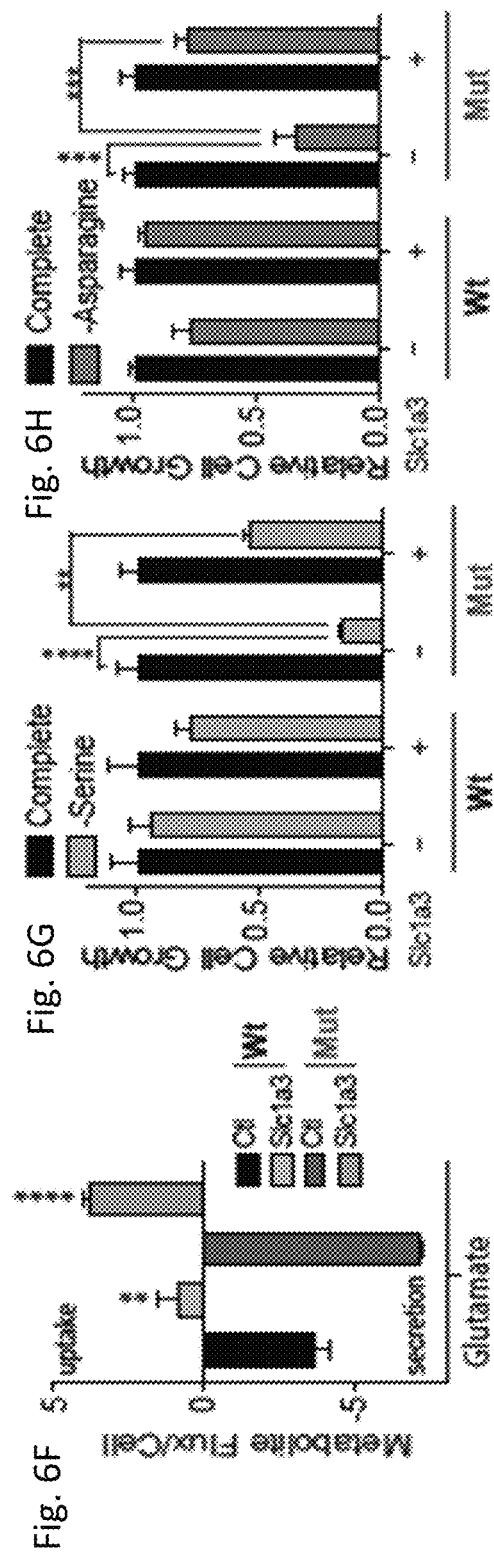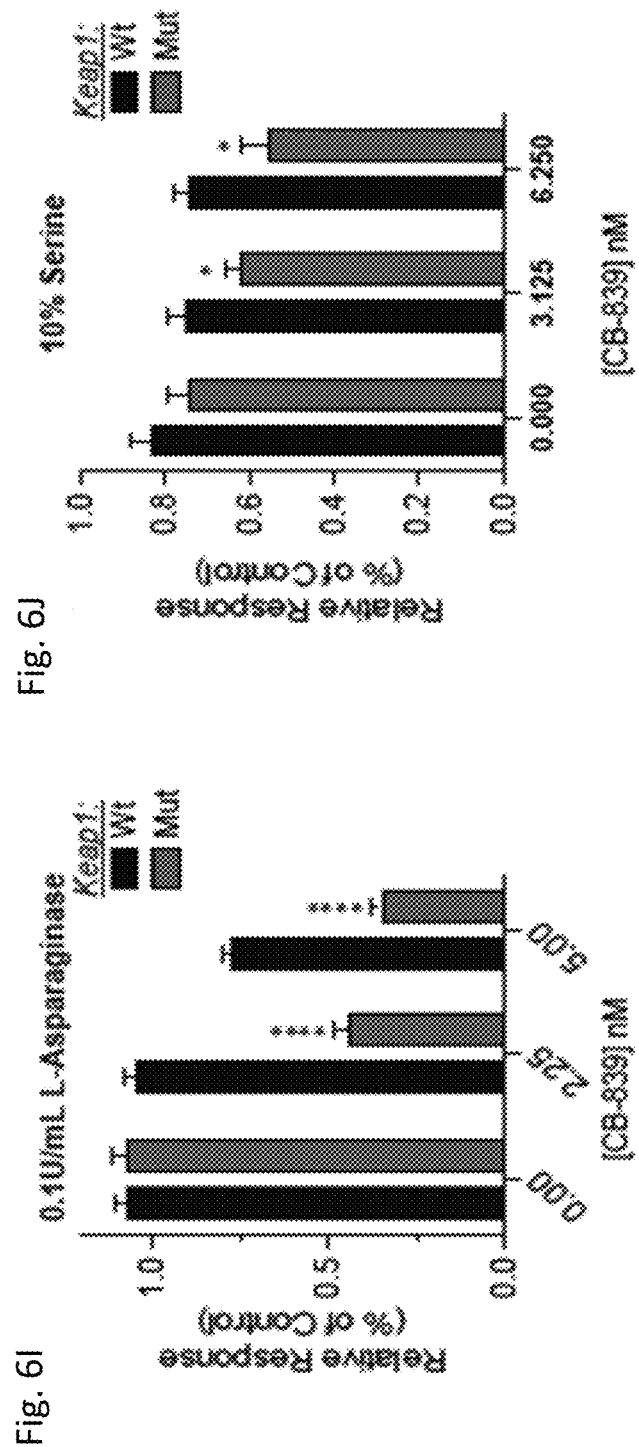

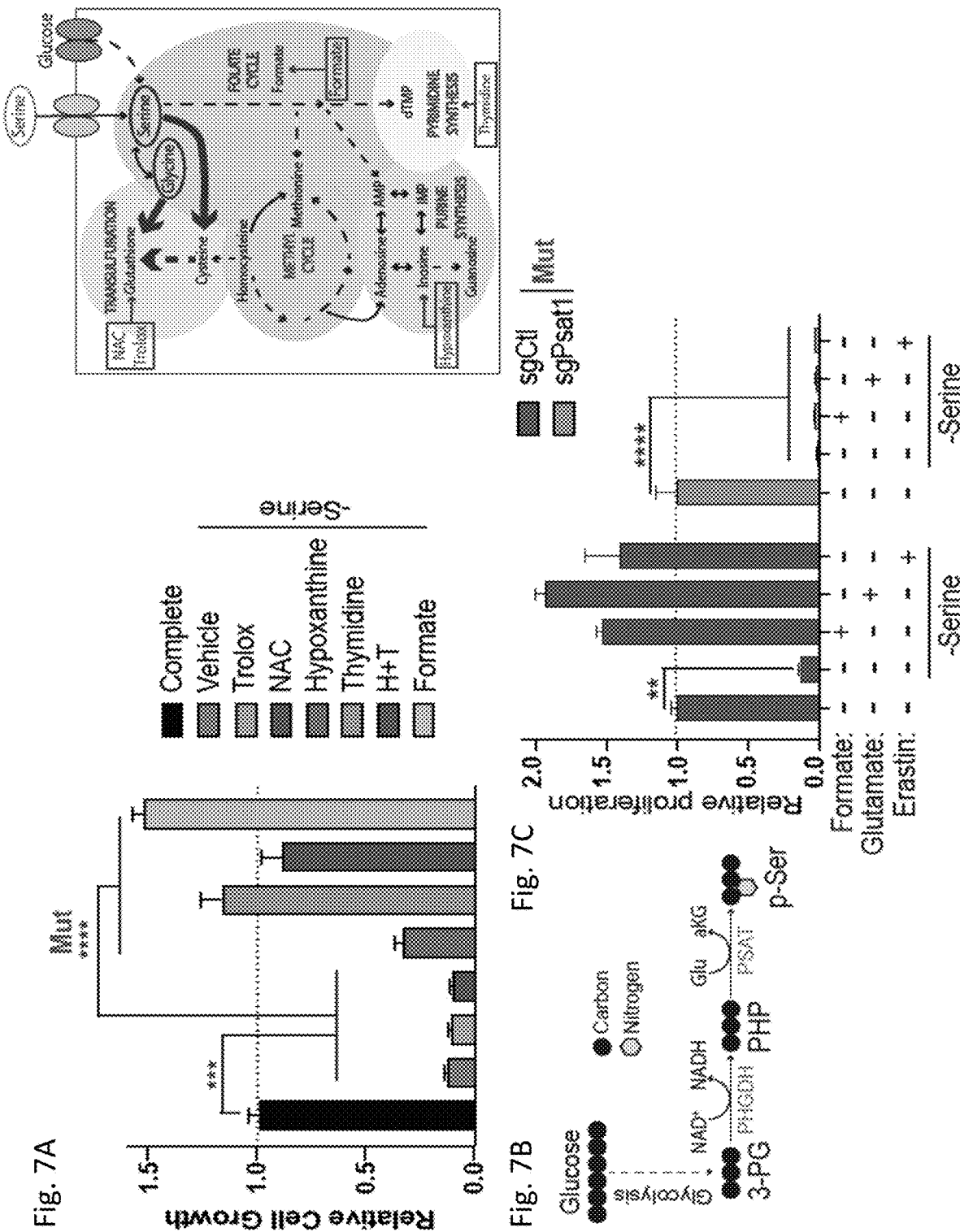

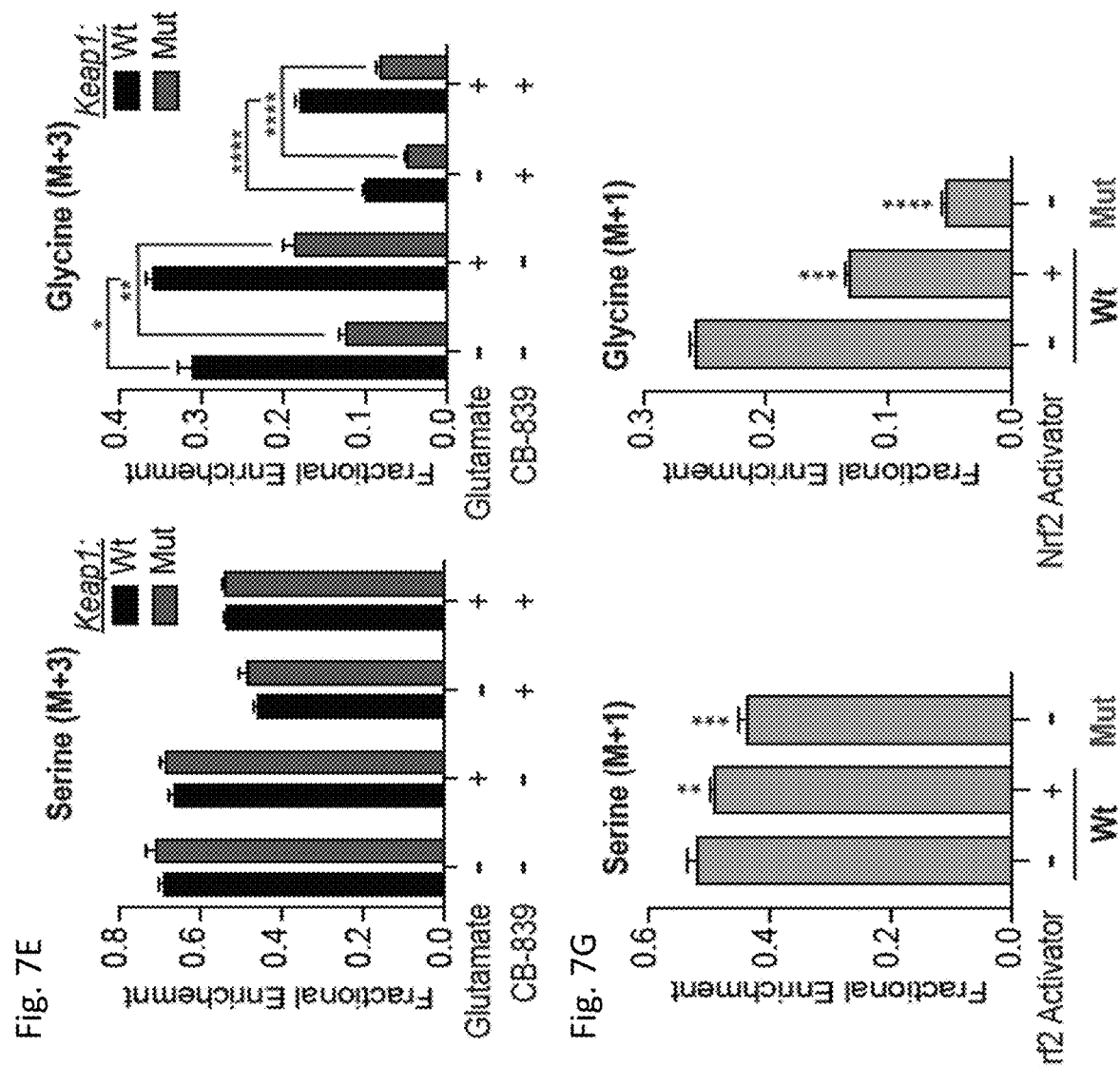

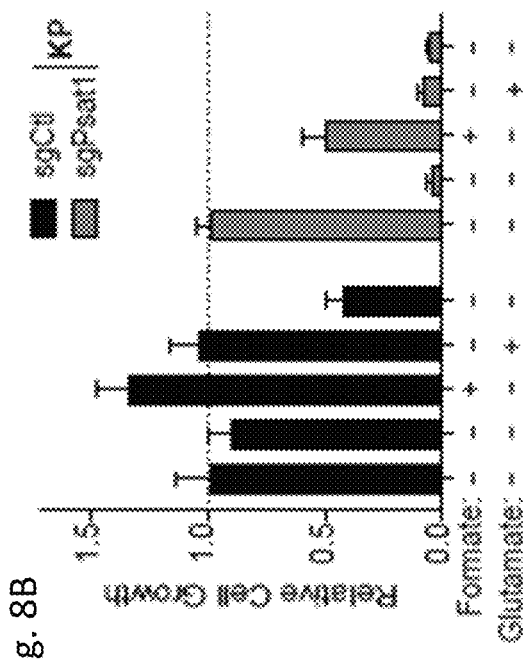
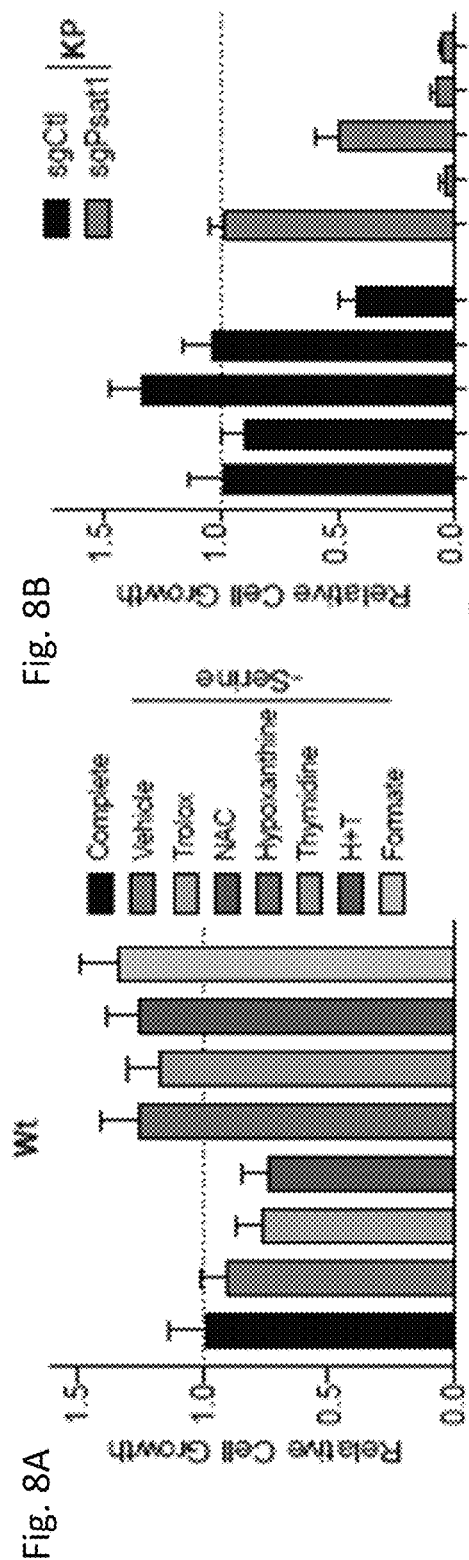
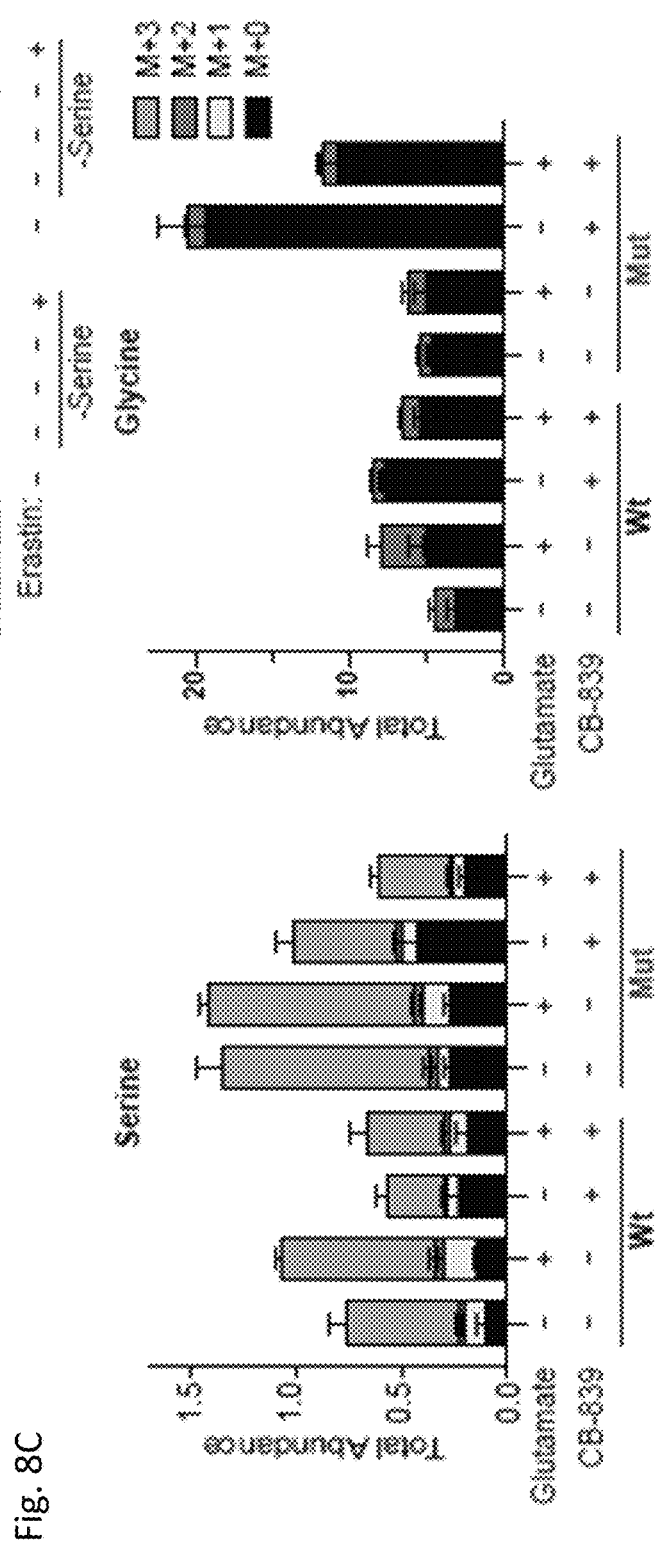

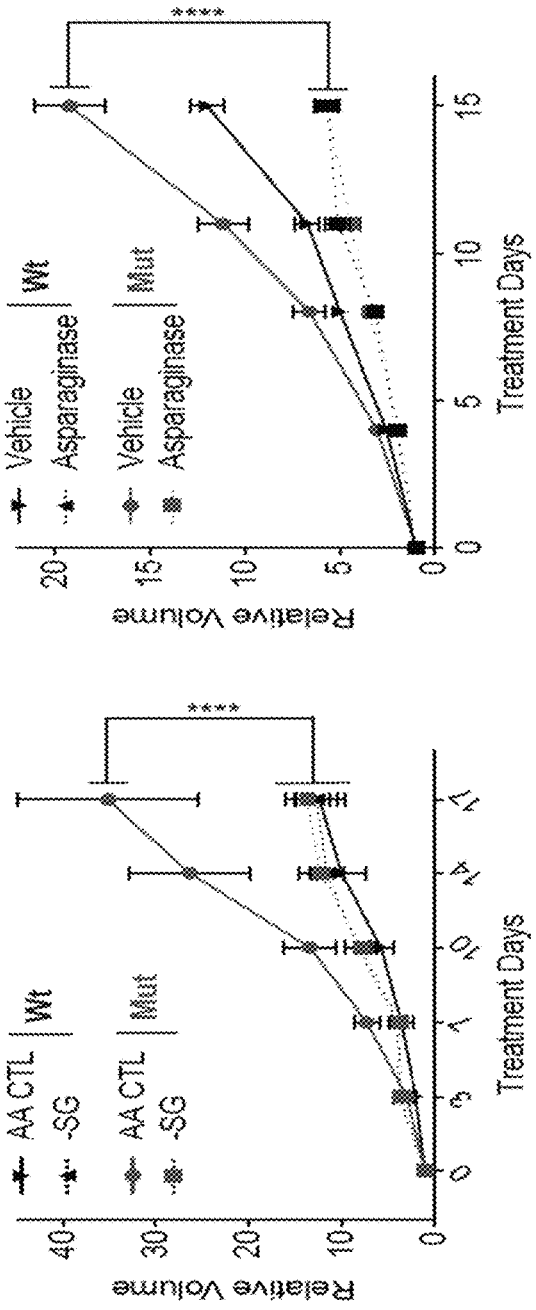
Fig. 9A
Fig. 9B
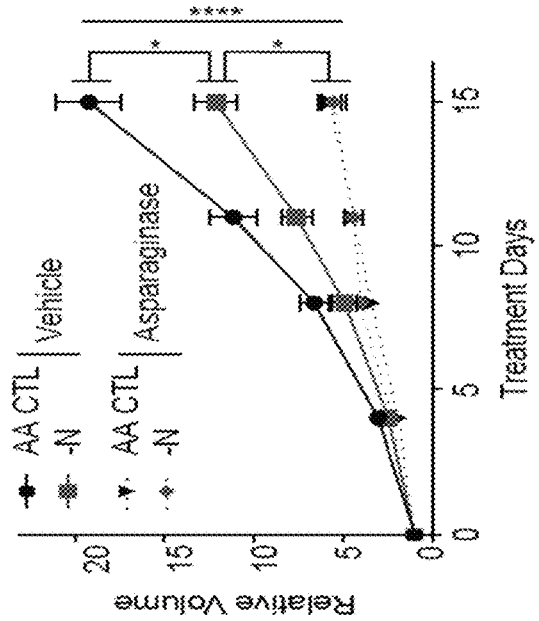
Fig. 9C
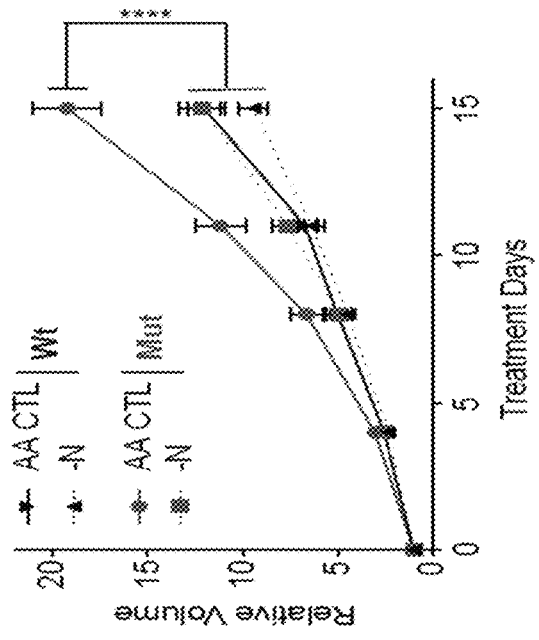
Fig. 9D

MODULATION OF OXIDATIVE STRESS AND AMINO ACID METABOLISM FOR THE TREATMENT OR PREVENTION OF DISEASES AND DISORDERS

CROSS REFERENCE TO RELATED APPLICATIONS

This application claims priority to U.S. Provisional Application No. 62/904,256, filed Sep. 23, 2019 which is hereby incorporated by reference herein in its entirety.

STATEMENT REGARDING FEDERALLY SPONSORED RESEARCH OR DEVELOPMENT

This invention was made with government support under K22 CA201088, R37 CA222504, R01 CA227649 awarded by The National Institutes of Health. The government has certain rights in the invention.

BACKGROUND

Nuclear Factor, Erythroid 2 Like 2 (NFE2L2; hereafter NRF2) is the master transcriptional regulator of the cell's antioxidant response. Nrf2 controls the transcription of a plethora of genes involved in the detoxification of reactive oxygen species (ROS). Under normal conditions Nrf2 is sequestered in the cytoplasm and targeted for proteasomal degradation through its interaction with Kelch-like ECH-associated protein 1 (hereafter Keap1). In the presence of ROS, key cystine residues on Keap1 are oxidized resulting in a conformational change which intern disrupts its interaction with Nrf2, allowing Nrf2 to translocate to the nucleus where it promotes transcription of target genes. KEAP1 or NRF2 are mutated in approximately 20% of KRAS-driven non-small-cell lung cancer (NSCLC), one of the most aggressive lung cancer subtypes, and therefore a major therapeutic target (Cronin et al., 2018, Cancer 124, 2785-2800). Additionally, mutations in the KEAP1/NRF2 antioxidant signaling pathway are common events in several solid cancers and are associated with poor patient prognosis and outcomes. Loss of KEAP1 and subsequent stabilization of NRF2 leads to metabolic reprogramming in order to promote the endogenous antioxidant response, which confers proliferative and survival advantages to tumor cells) (DeNicola et al., 2011, Nature 475, 106; Mitsuishi et al., 2012, Cancer Cell 22, 66-79; Romero et al., 2017, Nat Med 23, 1362-1368; Sayin et al., 2017, Elife 6). However, maintaining oxidative homeostasis through chronic activation of the NRF2 pathway results in a unique set of metabolic requirements to support increased antioxidant capacity (DeNicola et al., 2015 Nat Genet 47, 1475-1481; Koppula et al., 2017, J Biol Chem 292, 14240-14249; Mitsuishi et al., 2012, Cancer Cell 22, 66-79; Romero et al., 2017, Nat Med 23, 1362-1368; Sayin et al., 2017, Elife 6). KEAP1/NRF2-mutant tumors are dependent on exogenous glutamine to sustain proliferation (Romero et al., 2017, Nat Med 23, 1362-1368; Sayin et al., 2017, Elife 6). This dependency is due to two major transcriptional outputs of NRF2: 1) the consumption of glutamine-derived glutamate for glutathione (GSH) synthesis; and 2) the efflux of glutamate through system $x_c^-$, in exchange for cystine, the major source of cysteine for most cancer cells (Muir et al., 2017, Elife 6; Romero et al., 2017, Nat Med 23, 1362-1368; Sayin et al., 2017, Elife 6; Shin et al., 2017, Nat Commun 8, 15074). Depletion of endogenous glutamate pools due to high efflux through system $x_c^-$ compromises the use of glutamate as a carbon source for TCA cycle anaplerosis (Fox et al., 2019, bioRxiv, 513994; Koppula et al., 2017, J Biol Chem 292, 14240-14249; Muir et al., 2017, Elife 6; Sayin et al., 2017, Elife 6; Shin et al., 2017, Nat Commun 8, 15074).

In addition to supplying carbon to fuel central carbon metabolism, glutamate is a critical nitrogen donor for transamination reactions which catalyze the synthesis of NEAAs (DeBerardinis et al., 2007, Proc Natl Acad Sci USA 104, 19345-19350; Umbarger, 1978, nnu Rev Biochem 47, 532-606). NEAAs can be synthesized by cells de novo when their availability becomes limited. However, because of high proliferative capacity and increased metabolic output, many cancer cells become dependent on the exogenous supply of certain metabolites such as NEAAs, and synthesis is not adequate to keep up with demand (Tsun and Possemato, 2015, Semin Cell Dev Biol 43, 22-32). Although KEAP1/NRF2-mutations lead to a reliance on exogenous glutamine to supply glutamate, it remains unclear how other glutamate-dependent biosynthetic reactions, such as NEAA synthesis, are affected by this altered metabolic state where glutamate is actively secreted through system $xc^-$. Although most studies have focused on understanding how individual amino acids contribute to tumorigenesis, it remains elusive whether genetic alterations that promote tumor formation can rewire metabolism to generate a more general requirement for exogenous sources of NEAAs.

There is a great need in the art for novel methods of cancer treatment. The present invention satisfies this need.

SUMMARY OF THE INVENTION

In one embodiment, the invention relates to a method for treating or preventing tumor growth or metastasis in a subject in need thereof, the method comprising at least one of:
  a) increasing the level of reactive oxygen species (ROS) in the subject;
  b) administering a composition, or treatment regimen, for reducing the level of at least one amino acid selected from the group consisting of glutamate, glutamine, proline, serine, alanine, glycine, arginine, lysine, asparagine, methionine, threonine, and isoleucine;
  c) inhibiting the pentose phosphate pathway (PPP);
  d) inhibiting the sorbitol pathway; and
  e) inhibiting the heme biosynthesis pathway.

In one embodiment, the method of increasing the level of reactive oxygen species in the subject comprises a) administering an inhibitor of Keap1; b) administering an inhibitor of glutathione (GSH); c) administering an activator of NRF2; d) administering an inhibitor of thioredoxin reductases; or e) administering an electrophile that reacts with Keap1 cysteines and leads to Nrf2 stabilization, to the subject.

In one embodiment, the inhibitor of Keap1 is a chemical compound, a protein, a peptide, a peptidomemetic, an antibody, a ribozyme, a small molecule chemical compound, a nucleic acid, a vector, or an antisense nucleic acid molecule. In one embodiment, the inhibitor of Keap1 is KI-696 or an imidazole derivative of 2-cyano-3,12-dioxooleana-1,9(11)-dien-28-oic acid (CDDO-Im).

In one embodiment, the activator of NRF2 is a chemical compound, a protein, a peptide, a peptidomemetic, an antibody, a ribozyme, a small molecule chemical compound, a nucleic acid, a vector, or an antisense nucleic acid molecule.

In one embodiment, the method comprises administering at least one composition comprising a chemical compound, a protein, a peptide, a peptidomemetic, an antibody, a ribozyme, a small molecule chemical compound, a nucleic acid, a vector, or an antisense nucleic acid molecule.

In one embodiment, the composition for reducing the level of at least one amino acid comprises an asparaginase, a serine degrading enzyme, an inhibitor of phosphoserine aminotransferase, an inhibitor of an amino acid transporter, wherein the amino acid is selected from the group consisting of glutamate, glutamine, proline, serine, alanine, glycine, arginine, lysine, asparagine, methionine, threonine, and isoleucine, an inhibitor of glutaminase (GLS), an inhibitor of glutamate dehydrogenase (GLUD), or an aminotransferase inhibitor.

In one embodiment, the asparaginase is native asparaginase derived from *Escherichia coli*; a pegylated form of the native *E. coli*-asparaginase (polyethylene glycol-asparaginase); or an asparaginase enzyme isolated from *Erwinia chrysanthemi*.

In one embodiment, the serine degrading enzyme is L-serine ammonia lyase (SDH).

In one embodiment, the composition comprises GPNA, γ-FBP, benzylserine, BPTES, CB-839, compound 968, EGCG, R162, GCN2iA, DON or AOA.

In one embodiment, the treatment regimen is dietary restriction.

In one embodiment, the agent for inhibiting the PPP pathway comprises an inhibitor of glucose-6-phosphate dehydrogenase (G6PD or G6PDH), 6-phosphogluconolactonase, 6-phosphogluconate dehydrogenase, fructose-bisphosphate aldolase B, ribose-5-phosphate isomerase, Ribulose 5-Phosphate 3-Epimerase, transaldolase, solute carrier family 16 member 1 (SLC16A1 or MCT1) or lactate dehydrogenase A (LDHA). In one embodiment, the inhibitor of the PPP pathway is dehydropiandrosterone (DHEA), N-(4-Hydroxynaphthalen-1-yl)-2,5-dimethylbenzenesulfonamide (CB-83), 6-Aminonicotinamide, SR13800, AZD 3965, R-GNE-140, NCI-006 or G6PDi-1.

In one embodiment, the agent for inhibiting the heme pathway comprises an inhibitor of 5-aminolevulinic acid synthase-1 (ALAS1), delta-aminolevulinic acid dehydratase (ALAD), hydroxymethylbilane synthase (HMBS), uroporphyrinogen III synthase (UROS), uroporphyrinogen decarboxylase (UROD), coproporphyrinogen oxidase (CPOX), protoporphyrinogen oxidase (PPOX), transmembrane protein 14C (TMEM14C), FLVCR heme transporter 1 (FLVCR1), solute carrier family 48 member 1 (SLC48A1) or ferrochelatase (FECH). In one embodiment, the agent for inhibiting the heme pathway is heme, 4,6-Dioxoheptanoic acid (Succinylacetone), 6-Methyl-PBG, PI-16, SH-11052 or glucose.

In one embodiment, the agent for inhibiting the sorbitol pathway comprises an inhibitor of sorbitol dehydrogenase (SORD), ketohexokinase, Triokinase and FMN Cyclase (TKFC), aldo-keto reductase family 1, member B1 (AKR1b1), aldo-keto reductase family 1, member B3 (AKR1b3), aldo-keto reductase family 1, member B7 (AKR1b7), aldo-keto reductase family 1, member B8 (AKR1b8), aldo-keto reductase family 1, member B10 (AKR1b10), sterol regulatory element binding protein-1c (SREBP-1c), Carbohydrate-responsive element-binding protein (ChREBP), fructose transporter solute carrier family 2 member 5 (SLC2A5 or GLUT5), solute carrier family 16 member 1 (SLC16A1 or MCT1) or lactate dehydrogenase A (LDHA). In one embodiment, the agent for inhibiting the sorbitol pathway is aldose reductase inhibitors, Epalrestat, KHK-IN-1 hydrochlorid, PF-06835919, 2,5-Anhydro-D-mannitol, SR13800, AZD 3965, R-GNE-140, or NCI-006.

In one embodiment, the invention relates to a method for treating or preventing tumor growth or metastasis in a subject in need thereof, comprising: a) detecting at least one selected from the group consisting of a decreased level of Keap1 activity, an inactivating mutation of Keap1, an increased level of NRF2 activity, an increased level of a marker of NRf2 activation, and a mutation of a gene, wherein the mutation is associated with an increased level of NRF2 activity, in the tumor; and b) administering i) an agent or treatment regimen for reducing the level of at least one amino acid selected from the group consisting of glutamate, glutamine, proline, serine, alanine, glycine, arginine, lysine, asparagine, methionine, threonine, and isoleucine; ii) an agent for inhibiting the pentose phosphate pathway (PPP); iii) an agent for inhibiting the sorbitol pathway; or iv) an agent for inhibiting the heme biosynthesis pathway.

In one embodiment, the composition comprises at least one of a chemical compound, a protein, a peptide, a peptidomemetic, an antibody, a ribozyme, a small molecule chemical compound, a nucleic acid, a vector, or an antisense nucleic acid molecule.

In one embodiment, the agent for reducing the level of at least one amino acid comprises at least one of an asparaginase, a serine degrading enzyme, an inhibitor of phosphoserine aminotransferase, an inhibitor of an amino acid transporter, wherein the amino acid is selected from the group consisting of glutamate, glutamine, proline, serine, alanine, glycine, arginine, lysine, asparagine, methionine, threonine, and isoleucine, an inhibitor of glutaminase (GLS), an inhibitor of glutamate dehydrogenase (GLUD), an aminotransferase inhibitor, and a competitive inhibitor of glutamine.

In one embodiment, the asparaginase is native asparaginase derived from *Escherichia coli*; a pegylated form of the native *E. coli*-asparaginase (polyethylene glycol-asparaginase); or an asparaginase enzyme isolated from *Erwinia chrysanthemi*.

In one embodiment, the serine degrading enzyme is L-serine ammonia lyase (SDH).

In one embodiment, the composition comprises at least one of GPNA, γ-FBP, benzylserine, BPTES, CB-839, compound 968, EGCG, R162, GCN2iA, 6-diazo-5-oxo-1-norleucine (DON) and AOA.

In one embodiment, the treatment regimen is dietary restriction.

In one embodiment, the agent for inhibiting the PPP pathway comprises an inhibitor of glucose-6-phosphate dehydrogenase (G6PD or G6PDH), 6-phosphogluconolactonase, 6-phosphogluconate dehydrogenase, fructose-bisphosphate aldolase B, ribose-5-phosphate isomerase, Ribulose 5-Phosphate 3-Epimerase, transaldolase, solute carrier family 16 member 1 (SLC16A1 or MCT1) or lactate dehydrogenase A (LDHA). In one embodiment, the inhibitor of the PPP pathway is dehydropiandrosterone (DHEA), N-(4-Hydroxynaphthalen-1-yl)-2,5-dimethylbenzenesulfonamide (CB-83), 6-Aminonicotinamide, SR13800, AZD 3965, R-GNE-140, NCI-006 or G6PDi-1.

In one embodiment, the agent for inhibiting the heme pathway comprises an inhibitor of 5-aminolevulinic acid synthase-1 (ALAS1), delta-aminolevulinic acid dehydratase (ALAD), hydroxymethylbilane synthase (HMBS), uroporphyrinogen III synthase (UROS), uroporphyrinogen decarboxylase (UROD), coproporphyrinogen oxidase (CPOX), protoporphyrinogen oxidase (PPOX), transmembrane protein 14C (TMEM14C), FLVCR heme transporter 1 (FLVCR1), solute carrier family 48 member 1 (SLC48A1) or ferrochelatase (FECH). In one embodiment, the agent for inhibiting the heme pathway is heme, 4,6-Dioxoheptanoic acid (Succinylacetone), 6-Methyl-PBG, PI-16, SH-11052 or glucose.

In one embodiment, the agent for inhibiting the sorbitol pathway comprises an inhibitor of sorbitol dehydrogenase (SORD), ketohexokinase, Triokinase and FMN Cyclase (TKFC), aldo-keto reductase family 1, member B1 (AKR1b1), aldo-keto reductase family 1, member B3 (AKR1b3), aldo-keto reductase family 1, member B7 (AKR1b7), aldo-keto reductase family 1, member B8 (AKR1b8), aldo-keto reductase family 1, member B10 (AKR1b10), sterol regulatory element binding protein-1c (SREBP-1c), Carbohydrate-responsive element-binding protein (ChREBP), fructose transporter solute carrier family 2 member 5 (SLC2A5 or GLUT5), solute carrier family 16 member 1 (SLC16A1 or MCT1) or lactate dehydrogenase A (LDHA). In one embodiment, the agent for inhibiting the sorbitol pathway is aldose reductase inhibitors, Epalrestat, KHK-IN-1 hydrochlorid, PF-06835919, 2,5-Anhydro-D-mannitol, SR13800, AZD 3965, R-GNE-140, or NCI-006.

In one embodiment, the invention relates to a method for treating or preventing tumor growth or metastasis in a subject in need thereof, the method comprising a) detecting at least one of a decreased level of Keap1 activity, an inactivating mutation of Keap1, an increased level of NRF2 activity, an increased level of a marker of NRf2 activation, or a mutation of a gene, wherein the mutation is associated with an increased level of NRF2 activity, in the tumor; and b) administering a composition, or treatment regimen, for reducing the level of glutamate, glutamine, proline, serine, alanine, glycine, arginine, lysine, asparagine, methionine, threonine, or isoleucine.

In one embodiment, the composition comprises a chemical compound, a protein, a peptide, a peptidomemetic, an antibody, a ribozyme, a small molecule chemical compound, a nucleic acid, a vector, or an antisense nucleic acid molecule.

In one embodiment, the composition comprises an asparaginase, a serine degrading enzyme, an inhibitor of phosphoserine aminotransferase, an inhibitor of an amino acid transporter, wherein the amino acid is selected from the group consisting of glutamate, glutamine, proline, serine, alanine, glycine, arginine, lysine, asparagine, methionine, threonine, and isoleucine, an inhibitor of glutaminase (GLS), an inhibitor of glutamate dehydrogenase (GLUD), an aminotransferase inhibitor, or a competitive inhibitors of glutamine.

In one embodiment, the asparaginase is native asparaginase derived from *Escherichia coli;* a pegylated form of the native *E. coli*-asparaginase (polyethylene glycol-asparaginase); or an asparaginase enzyme isolated from *Erwinia chrysanthemi*.

In one embodiment, the serine degrading enzyme is L-serine ammonia lyase (SDH).

In one embodiment, the composition comprises GPNA, γ-FBP, benzylserine, BPTES, CB-839, compound 968, EGCG, R162, GCN2iA, 6-diazo-5-oxo-1-norleucine (DON) or AOA.

In one embodiment, the treatment regimen is dietary restriction.

In one embodiment, the invention relates to a method for treating or preventing tumor growth or metastasis in a subject in need thereof, the method comprising: a) increasing the level of reactive oxygen species in the subject; and b) administering a composition, or treatment regimen, for reducing the level of at least one of glutamate, glutamine, proline, serine, alanine, glycine, arginine, lysine, asparagine, methionine, threonine, and isoleucine.

In one embodiment, the method of increasing the level of reactive oxygen species in the subject comprises: a) administering an inhibitor of Keap1; b) administering an inhibitor of glutathione (GSH); c) administering an activator of NRF2; d) administering an inhibitor of thioredoxin reductases; or e) administering an electrophile that reacts with Keap1 cysteines and leads to Nrf2 stabilization, to the subject.

In one embodiment, the inhibitor of Keap1 is a chemical compound, a protein, a peptide, a peptidomemetic, an antibody, a ribozyme, a small molecule chemical compound, a nucleic acid, a vector, or an antisense nucleic acid molecule. In one embodiment, the inhibitor of Keap1 is KI-696 or an imidazole derivative of 2-cyano-3,12-dioxooleana-1,9(11)-dien-28-oic acid (CDDO-Im).

In one embodiment, the activator of NRF2 is a chemical compound, a protein, a peptide, a peptidomemetic, an antibody, a ribozyme, a small molecule chemical compound, a nucleic acid, a vector, or an antisense nucleic acid molecule.

In one embodiment, the composition for reducing the level of at least one of glutamate, glutamine, proline, serine, alanine, glycine, arginine, lysine, asparagine, methionine, threonine, and isoleucine comprises a chemical compound, a protein, a peptide, a peptidomemetic, an antibody, a ribozyme, a small molecule chemical compound, a nucleic acid, a vector, or an antisense nucleic acid molecule. In one embodiment, the composition comprises at least one of an asparaginase, a serine degrading enzyme, an inhibitor of phosphoserine aminotransferase, an inhibitor of an amino acid transporter, wherein the amino acid is selected from the group consisting of glutamate, glutamine, proline, serine, alanine, glycine, arginine, lysine, asparagine, methionine, threonine, and isoleucine, an inhibitor of glutaminase (GLS), an inhibitor of glutamate dehydrogenase (GLUD), and an aminotransferase inhibitor.

In one embodiment, the asparaginase is native asparaginase derived from *Escherichia coli;* a pegylated form of the native *E. coli*-asparaginase (polyethylene glycol-asparaginase); or an asparaginase enzyme isolated from *Erwinia chrysanthemi*.

In one embodiment, the serine degrading enzyme is L-serine ammonia lyase (SDH).

In one embodiment, the composition comprises GPNA, γ-FBP, benzylserine, BPTES, CB-839, compound 968, EGCG, R162, GCN2iA, DON or AOA.

In one embodiment, the treatment regimen is dietary restriction.

BRIEF DESCRIPTION OF THE DRAWINGS

The following detailed description of the invention will be better understood when read in conjunction with the appended drawings. For the purpose of illustrating the invention, several exemplary embodiments are shown in the drawings. It should be understood, however, that the invention is not limited to the precise arrangements and instrumentalities of the embodiments shown in the drawings.

FIG. 1A depicts an in vitro uptake assay comparing uptake of amino acids in wildtype vs Keap1 mutant cell lines after 24 hours in RPMI media. FIG. 1B depicts measurement of serum level of asparagine, glycine and serine in mice bearing a wildtype or Keap1 mutant subcutaneous tumor. FIG. 1C depicts proliferation of wildtype vs Keap1 mutant cells in RPMI media lacking specified amino acid. All data points are relative to vehicle treated controls. FIG. 1D depicts the relative viability assayed with cell-titer glo (relative luminescent units) in wildtype and Keap1 mutant cells cultured in RPMI and treated with L-asparaginase for 3 days. All data points are relative to vehicle treated controls. FIG. 1E depicts proliferation of wildtype (WT) or Keap1 mutant (Mut) LKR (Kras$^{G12D/+}$; p53$^{+/+}$) cell lines in media lacking serine or asparagine. Data is represented as relative to growth in complete media condition.

FIG. 2A through FIG. 2F depicts the results of exemplary experiments demonstrating that KEAP1 loss increases dependency on exogenous supply of NEAAs. FIG. 2A depicts a mass isotopomer analysis of serine in wildtype and Keap1 mutant cells cultured for 3 hours with [U$^{13}$C]-L-serine (Left). Total abundance of serine in wildtype and Keap1 mutant cells depicted in left panel (right). FIG. 2B depicts the measurement of serum level of non-essential amino acids in mice bearing wildtype or Keap1 mutant subcutaneous tumors. Full panel of detectable metabolites that are represented in FIG. 1D. FIG. 2C depicts the proliferation of wildtype vs Keap1 mutant cells in RPMI media lacking specified amino acid. Full panel of deprived amino acids that is represented in FIG. 1A. Data is represented as relative to growth in complete media condition. FIG. 2D depicts the proliferation of wildtype vs Keap1 mutant cells in RPMI (10% dialyzed FBS) supplemented with alanine. Data is represented as relative to growth in complete media condition. FIG. 2E depicts the proliferation of a panel of human lung adenocarcinoma cell lines in RPMI lacking serine Each individual point represents an independent cell line. Response is represented as relative to growth in complete media conditions. FIG. 2F depicts the proliferation of human lung adenocarcinoma cell lines shown in panel e in RPMI lacking serine. Data is represented as relative to proliferation in complete media. All error bars depict s.e.m. *p<0.05, p<0.01, *p<0.001, ****p<0.0001.

FIG. 3A depicts (left panels) a mass isotopomer analysis of serine and glycine in wildtype vs Keap1 mutant cells in complete media vs RPMI lacking serine. Cells were cultured in [U$^{13}$C]-D-glucose for 3 hours; and (right panel) a relative abundance of glycine in wildtype vs Keap1 mutant cells in complete media vs RPMI lacking serine (from left panel). Relative pool sizes are normalized to cell counts for each condition. FIG. 3B depicts (left panels) a mass isotopomer analysis of asparagine and aspartate in wildtype vs Keap1 mutant cells in complete media vs RPMI lacking asparagine. Cells were cultured in [U$^{13}$C]-L-glutamine for 1 hour. The right panel depicts the relative abundance of aspartate in wildtype vs Keap1 mutant cells in complete media vs RPMI lacking asparagine (from left panel). Relative pool sizes are normalized to cell counts for each condition. FIG. 3C depicts the relative abundance of aspartate in Keap1 mutant cells from panel e and relative abundance of asparagine in Keap1 mutant cells from FIG. 1I. Data is represented as relative to proliferation in complete media. All error bars depict s.e.m. *p<0.05, p<0.01, *p<0.001, ****p<0.0001.

FIG. 4A through FIG. 4G depict the results of exemplary experiments demonstrating that acute activation of Nrf2 induces dependency on nonessential amino acids. FIG. 4A depicts the proliferation of wildtype cells in complete media or RPMI lacking serine. Cells were pretreated with 1 μM of Nrf2 activator (KI696) where indicated. Data is represented as relative to proliferation in complete media. FIG. 4B depicts the proliferation of wildtype cells that were pretreated with 1 μM Nrf2 activator (KI696) in complete media or RPMI lacking asparagine. Data is represented as relative to proliferation in complete media. FIG. 4C depicts the proliferation of wildtype cells treated with L-Asparaginase. Cells were pretreated with 1 μM Nrf2 activator (KI696) where indicated. Data is represented as relative to proliferation in complete media. FIG. 4D depicts the proliferation of wildtype vs Keap1 mutant cells treated with L-asparaginase. Cells were supplemented with 6 mM glutamate or 500 nM Erastin where indicated. Data is represented as relative to proliferation in complete media. FIG. 4E depicts the proliferation of murine PDAC (Kras$^{G12D/+}$;p53$^{-/-}$) cell line in media lacking serine (left) or asparagine (right). Cells were pre-treated with 6 mM glutamate and 1 μM Nrf2 activator (KI696) where indicated. Data is represented as relative to proliferation in complete media. FIG. 4F depicts the proliferation of wildtype vs Keap1 mutant cells expressing Slc1a3 or an empty vector control after treatment with 250 nM CB-839. Data is represented as relative to proliferation in complete media. FIG. 4G depicts the proliferation of wildtype vs Keap1 mutant cells expressing Slc1a3 or an empty vector control after treatment with L-asparaginase. Data is represented as relative to proliferation in complete media. All error bars depict s.e.m. *p<0.05, p<0.01, *p<0.001, ****p<0.0001.

FIG. 5A through FIG. 5F depict the results of exemplary experiments demonstrating that acute activation of Nrf2 induces dependency on nonessential amino acids. FIG. 5A depicts the proliferation of a panel of wildtype (Kras$^{G12D/+}$; p53$^{-/-}$) tumor cell lines in the absence of serine or asparagine. Cell lines were pre-treated with 1 μM of Nrf2 activator (KI696) to activate Nrf2 where indicated. Each individual point represents an independent cell line. Response is represented as relative to growth in complete media conditions. FIG. 5B depicts the proliferation of wildtype (WT) LKR (Kras$^{G12D/+}$;p53$^{+/+}$) cell lines in media lacking serine or asparagine. Cells were pre-treated with 11 μM of Nrf2 activator (KI696) where indicated. Data is represented as relative to growth in complete media condition. FIG. 5C depicts the proliferation of wildtype murine Kras$^{G12D/+}$; p53$^{-/-}$ pancreatic cancer cell line in media lacking serine. Cells were pre-treated with 1 μM of Nrf2 activator (KI696) where indicated. Response is represented as relative to growth in complete media conditions. FIG. 5D depicts the relative viability assayed with cell-titer glo (relative luminescent units) in wildtype murine Kras$^{G12D/+}$;p53$^{-/-}$ pancreatic cancer cell line cultured in RPMI and treated with 0.036 U/mL L-asparaginase for 3 days. Cells were pre-treated with 1 μM of Nrf2 activator (KI696) where indicated. All data points are relative to vehicle treated controls. FIG. 5E depicts a schematic depicting mechanism of action of oxidants used to interfere with various aspects of the endogenous anti-oxidant response and activate Nrf2. FIG. 5F depicts a schematic depicting mechanism of action of oxidants used to increase ROS in Keap1 wildtype cells. Auranofin treatment inhibits thioredoxin reductase which catalyzes the reduction of thioredoxin after. Treatment with L-buthionine-sulfoximine (BSO) inhibits GCLC, which catalyzes the rate limiting step of glutathione (GSH) synthesis. Di-methyl fumarate (DMF) acts as a general oxidative stress agent and reacts with free cysteines. Cysteine residues on Keap1 will be oxidized, dissociating it from Nrf2.

FIG. 6A through FIG. 6J depict the results of exemplary experiments demonstrating that low intracellular glutamate levels in cells with Nrf2 activation generates a dependency on exogenous NEAAs. FIG. 6A depicts a schematic depicting modulation of intracellular glutamate levels by: 1) using the small molecule Erastin to inhibit glutamate export through the system xc– cystine/glutamate antiporter 2) supplementation of high levels of extracellular glutamate to reverse the directionality of glutamate transport through system xc– or 3) over expression of Slc1a3, a glutamate transporter that allows for the re-uptake of glutamate from the media. FIG. 6B depicts the relative intracellular abundance of glutamate in wildtype vs Keap1 mutant cells supplemented with 6 mM glutamate where indicated. Total metabolite pool sizes are normalized to cell counts for each condition. FIG. 6C depicts the relative intracellular abundance of glutamate in wildtype vs Keap1 mutant cells treated with 500 nM Erastin where indicated. Total metabolite pool sizes are normalized to cell counts for each condition. FIG. 6D depicts the proliferation of wildtype vs Keap1 mutant cells in media lacking serine. Cells were supplemented with 6 mM glutamate or 500 nM Erastin where indicated. Data is represented as relative to proliferation in complete media. FIG. 6E depicts the proliferation of wildtype vs Keap1 mutant cells in media lacking asparagine. Cells were supplemented with 6 mM glutamate or 500 nM Erastin where indicated. Data is represented as relative to proliferation in complete media. FIG. 6F depicts the relative metabolite flux of glutamate in wildtype vs Keap1 mutant cells expressing Slc1a3 or an empty vector control. FIG. 6F depicts the proliferation of wildtype vs Keap1 mutant cells expressing Slc1a3 or an empty vector control in media lacking serine. Data is represented as relative to proliferation in complete media. FIG. 6H depicts the proliferation of wildtype vs Keap1 mutant cells expressing Slc1a3 or an empty vector control in media lacking asparagine. Data is represented as relative to proliferation in complete media. FIG. 6I depicts the relative viability assayed with cell titer glow of wildtype vs Keap1 mutant cells cultured in 0.1 U/mL of L-Asparaginase with increasing doses of CB-839. Data is represented as response to CB-839 treatment alone. FIG. 6J depicts the relative viability assayed with cell titer glow of wildtype vs Keap1 mutant cells cultured in RPMI containing 10% of the normal concentration of serine with increasing doses of CB-839. Data is represented as response to CB-839 treatment in 100% serine. All error bars depict s.e.m. *$p<0.05$, $p<0.01$, *$p<0.001$, ****$p<0.0001$.

FIG. 7A through FIG. 7G depict the results of exemplary experiments demonstrating that glutamate availability restricts serine biosynthesis. FIG. 7A depicts (left) proliferation of Keap1 mutant cells in RPMI lacking serine. Where indicated cells were supplemented with 3 mM Formate, 30 uM hypoxanthine, 16 μM thymidine, 30 μM hypoxanthine and 16 μM thymidine (H+T), 50 μM Trolox, or 0.5 mM NAC. Data is represented as relative proliferation in vehicle treated complete media; and (right) a schematic depicting serine metabolism and the various biosynthetic pathways it supports. Red boxes and arrows indicate the various metabolites that can supplement serine-derived metabolites in the absence of exogenous serine. FIG. 7B depicts a schematic depicting the first steps of serine biosynthesis from glucose in which the transaminase PSAT catalyzes the transamination of 3-phosphohydroxypurvate (PHP) to 3-phosphoserine (P-Ser) using an amino group from glutamate. Filled black circles indicate carbon atoms and filled yellow hexagons represent nitrogen atoms. FIG. 7C depicts the proliferation Keap1 mutant cells expressing an sgRNA against PSAT or a non-targeting control (sgCtl) in media lacking serine. Cells were supplemented with 3 mM Formate, 6 mM glutamate, or 500 nM Erastin where indicated. FIG. 7D depicts a schematic depicting serine biosynthesis from glucose. Filled blue circles represent $^{13}C$ atoms derived from [U$^{13}C$]-D-glucose. FIG. 7E depicts a mass isotopomer analysis of serine and glycine in wildtype vs Keap1 mutant cells cultured in RPMI lacking serine. Cells were supplemented with 6 mM glutamate or treated with 250 nM CB-839 where indicated. FIG. 7F depicts a schematic depicting serine biosynthesis from glucose utilizing an amino group from glutamate. Filled orange hexagons represent $^{15}N$ atoms derived from [α$^{15}N$]-L-glutamine. FIG. 7G depicts a mass isotopomer analysis of serine and glycine in wildtype vs Keap1 mutant cells cultured in RPMI lacking serine. KP cells were pre-treated with 1 μM of Nrf2 activator (KI696) where indicated. All error bars depict s.e.m. *$p<0.05$, $p<0.01$, **$p<0.0001$.

FIG. 8A through FIG. 8E depict the results of exemplary experiments demonstrating that glutamate availability restricts serine biosynthesis. FIG. 8A depicts the proliferation of wildtype cells in RPMI lacking serine. Where indicated cells were supplemented with 3 mM Formate, 30 μM hypoxanthine, 16 μM thymidine, 30 μM hypoxanthine and 16 μM thymidine (H+T), 50 μM Trolox, or 0.5 mM NAC. Data is represented as relative proliferation in vehicle treated complete media. FIG. 8B depicts the proliferation wildtype cells expressing an sgRNA against PSAT or a non-targeting control (sgCtl) in media lacking serine. Cells were supplemented with 3 mM Formate, 6 mM glutamate, or 500 nM Erastin where indicated. Data is represented as relative proliferation in vehicle treated complete media. FIG. 8A depicts the relative abundance of serine and glycine in wildtype vs Keap1 mutant cells depicted from FIG. 7E. Relative pool sizes are normalized to cell counts for each condition. FIG. 8D depicts the relative abundance of serine and glycine in wildtype vs Keap1 mutant cells depicted from FIG. 7G. Relative pool sizes are normalized to cell counts for each condition. FIG. 8E depicts a mass isotopomer analysis of serine and glycine in wildtype vs Keap1 mutant cells cultured in complete media. KP cells were pre-treated with 1 μM of Nrf2 activator (KI696) where indicated. All error bars depict s.e.m.

FIG. 9A through FIG. 9F depict the results of exemplary experiments demonstrating that Keap1 mutant tumors require exogenous NEAAs in vivo. FIG. 9A depicts the relative tumor growth of subcutaneous wildtype or Keap1 mutant tumors. Animals were randomized to receive either a diet lacking serine and glycine (–SG) or an amino acid control diet (AA CTL). FIG. 9B depicts the relative tumor growth of subcutaneous wildtype or Keap1 mutant tumors. Animals were randomized to be treated with either L-Asparaginase or vehicle. FIG. 9C depicts the relative tumor growth of subcutaneous wildtype or Keap1 mutant tumors. Animals were randomized to receive either a diet lacking asparagine (−N) or an amino acid control diet (AA CTL). FIG. 9D depicts the relative tumor growth of subcutaneous Keap1 mutant tumors. Animals were randomized to receive either a diet lacking asparagine (−N) or an amino acid control diet (AA CTL) and either treated with L-asparaginase or vehicle. FIG. 9E depicts the relative tumor growth of subcutaneous Keap1 mutant tumors. Animals were randomized to receive either a diet lacking serine and glycine (−SG) or an amino acid control diet (AA CTL) and either treated with CB-839 or vehicle. FIG. 9F depicts the relative tumor growth of subcutaneous wildtype tumors. Animals were randomized to receive either a diet lacking serine and glycine (−SG) or an amino acid control diet (AA CTL) and either treated with CB-839 or vehicle. All error bars depict s.e.m. *p<0.05, p<0.01, **p<0.0001.

FIG. 10A depicts tumor volumes of subcutaneous wildtype (left) and Keap1 mutant (right) tumors on AA CTL or −SG diet from FIG. 9A and FIG. 9B. FIG. 10B depicts tumor volumes of subcutaneous wildtype (left) and Keap1 mutant (right) tumors treated with vehicle or L-asparaginase from FIG. 9B. FIG. 10C depicts the measurement of serum level of serine and glycine in mice bearing wildtype (black/grey) or Keap1 mutant (blue/light blue) subcutaneous tumor receiving amino acid control (AA CTL) diet or a diet lacking serine and glycine (−SG). Serum analyzed from mice from FIG. 9A. All error bars depict s.e.m. *p<0.05, p<0.01, **p<0.0001.

FIG. 11A depicts the measurement of serum level of asparagine, glutamine, glutamate and aspartate in mice bearing Keap1 mutant subcutaneous tumors receiving vehicle or L-asparaginase. Serum analyzed from mice from FIG. 9C and FIG. 9D. FIG. 11B depicts the tumor volumes of subcutaneous wildtype and Keap1 mutant tumors on AA CTL or −N diet. FIG. 11C depicts tumor volumes of subcutaneous Keap1 mutant (left) and wildtype (right) tumors on AA CTL or −SG diet and treated with CB-839 or vehicle from FIG. 9E and FIG. 9F. All error bars depict s.e.m. *p<0.05, p<0.01, **p<0.0001.

FIG. 12A depicts a schematic depicting how activation of the oxidative stress response via genetic, pharmacologic or physiological ROS stress to stabilize Nrf2 depletes intracellular glutamate. In cells with activated Nrf2 glutamate is shuttled into glutathione (GSH) biosynthesis or exported through the system xc− antiporter (xCT) to import cystine. This depletes intracellular glutamate levels and limits its availability for other biosynthetic reactions. Reduced availability of intracellular glutamate restricts its use in transamination reactions for synthesis of nonessential amino acids (NEAA) rendering cells dependent on uptake of NEAAs from the microenvironment. FIG. 12B depicts a schematic depicting the balance between the use of glutamate to import cysteine for antioxidant production versus using glutamate for NEAA synthesis (left). Activation of Nrf2 through exposure to ROS or by a small molecule activator (KI696) results in an imbalance between the production of antioxidants and the use of glutamate for NEAA synthesis. Cells with activated Nrf2 have decreased intracellular glutamate availability and are dependent on the exogenous supply of NEAAs. CB-839, a glutaminase inhibitor can be used to decrease intracellular glutamate and further sensitize cells with Nrf2 activation or sensitize wildtype cells to NEAA deprivation.

For the following Figures, the abbreviations are defined as:

KP: $Kras^{G12D/+}$; $p53^{-/-}$ mouse lung cancer cell line (Keap1 wt, named as KP)

KP+KI: KP cells treated with KI696, NRF2 activator, at least two weeks (NRF2 activator, named as KI)

KPKJ: KP cells with Keap1 knocked out

KPKJ Vector: KPKJ cells overexpressing vector (Keap1 knockout, named as KO)

KPKJ wt: KPKJ cells overexpressing Keap1 wt cDNA (Keap1 wt, named as KO+Keap1).

Figure 13A:
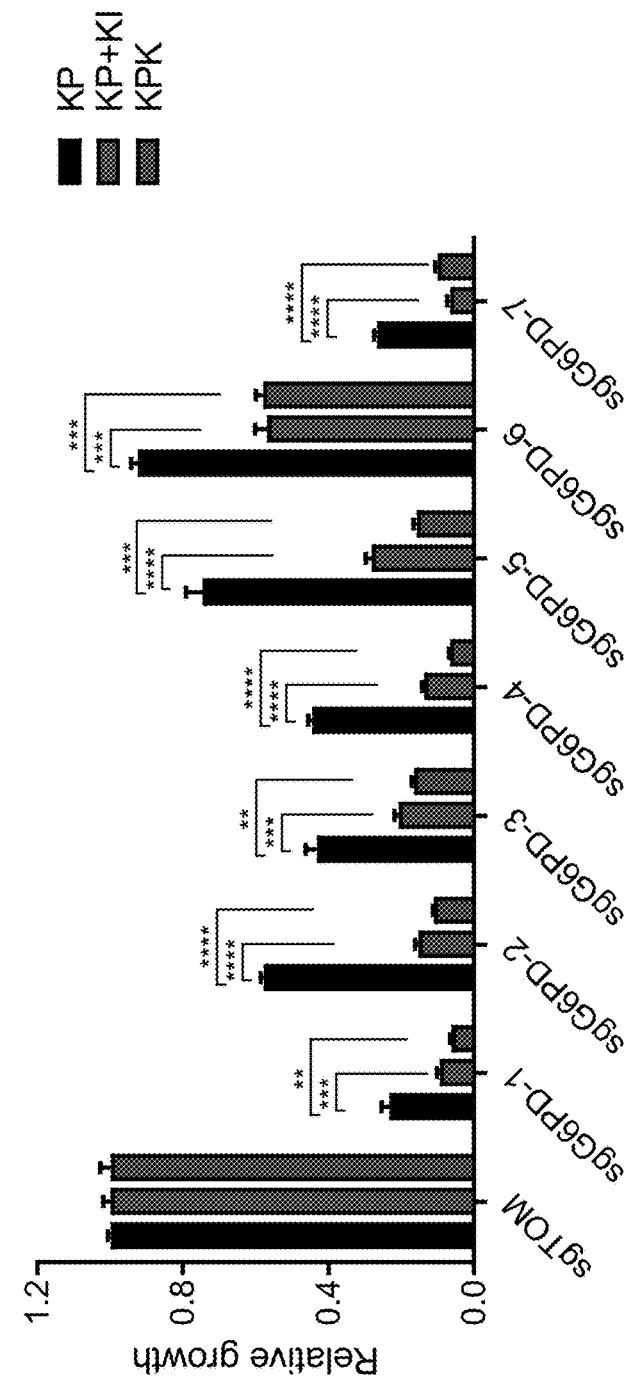
Figure 13B:
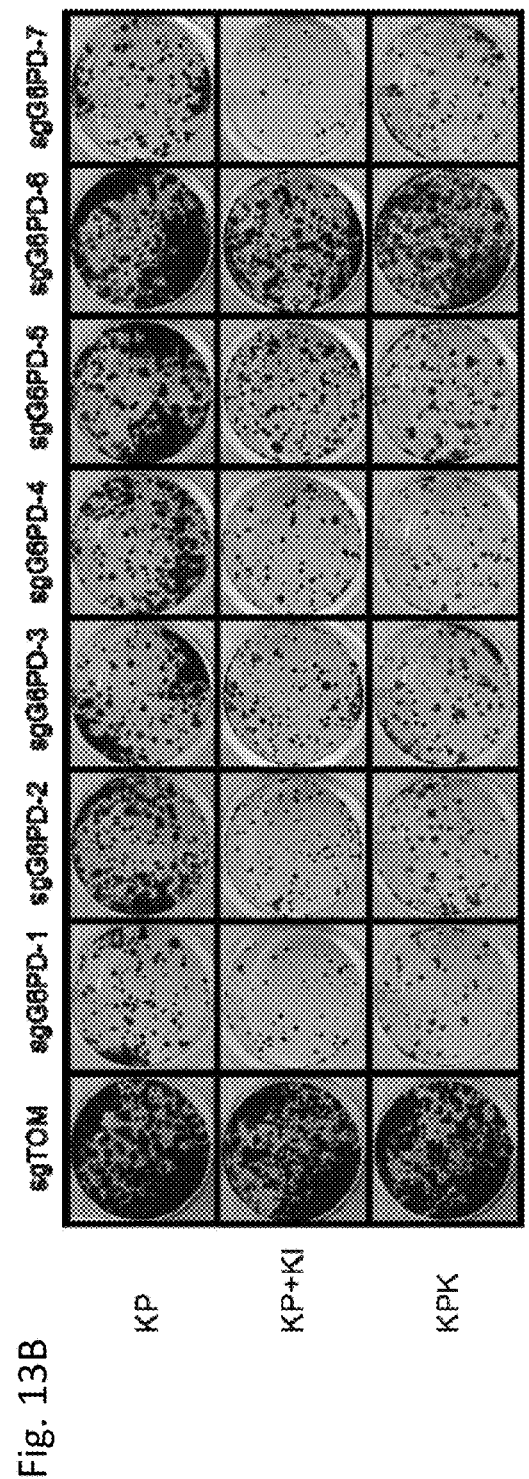

FIG. 13A and FIG. 13B depict the results of exemplary experiments demonstrating KEAP1-G6PD synergy lethality in mouse lung adenocarcinoma. FIG. 13A and FIG. 13B depict a colony formation assay in KP (Keap1 wildtype), KP+KI (NRF2 activator) and KPK (Keap1 KO) cells transduced with sgTom or sgG6pd. FIG. 13A is the quantification of crystal violet staining (FIG. 13B).

Figure 14A:
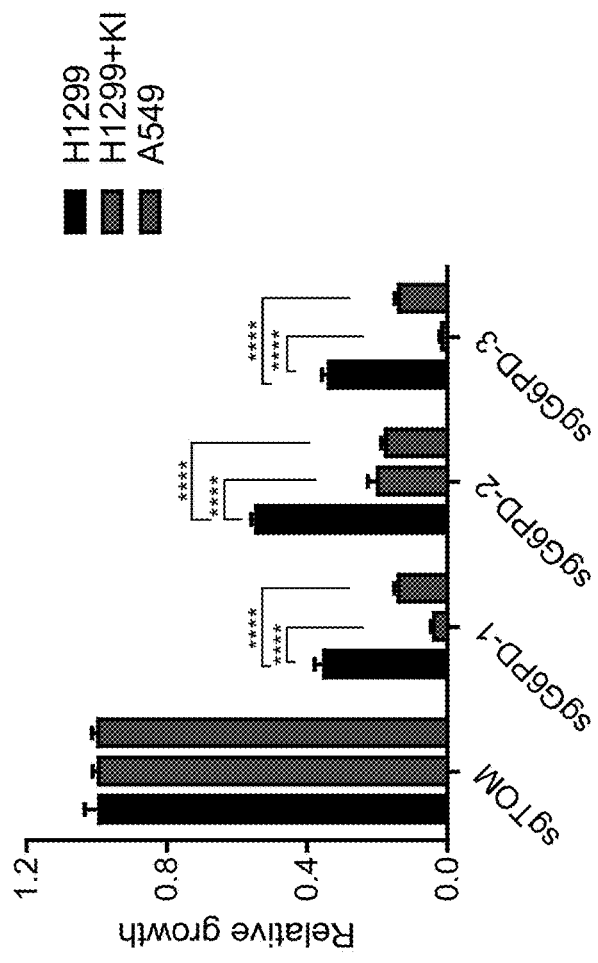
Figure 14B:
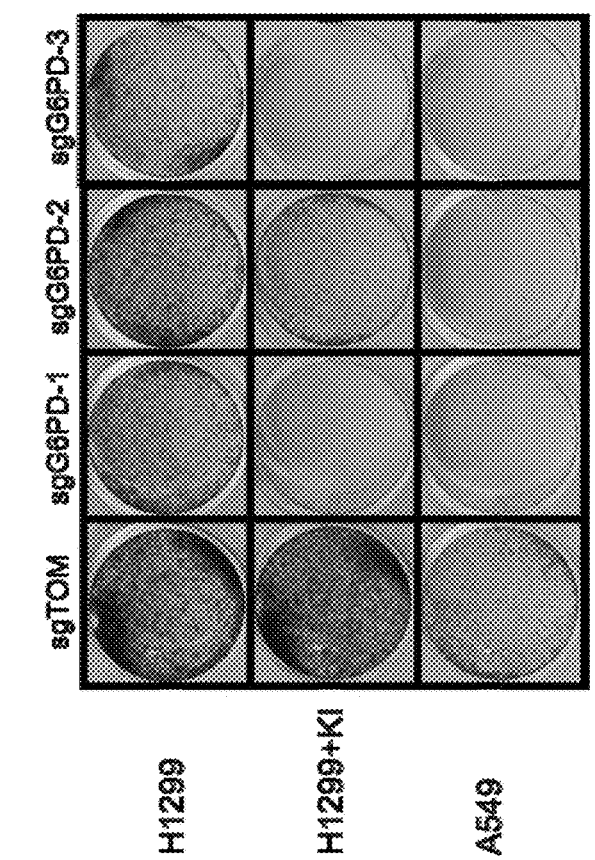
Figure 14C:
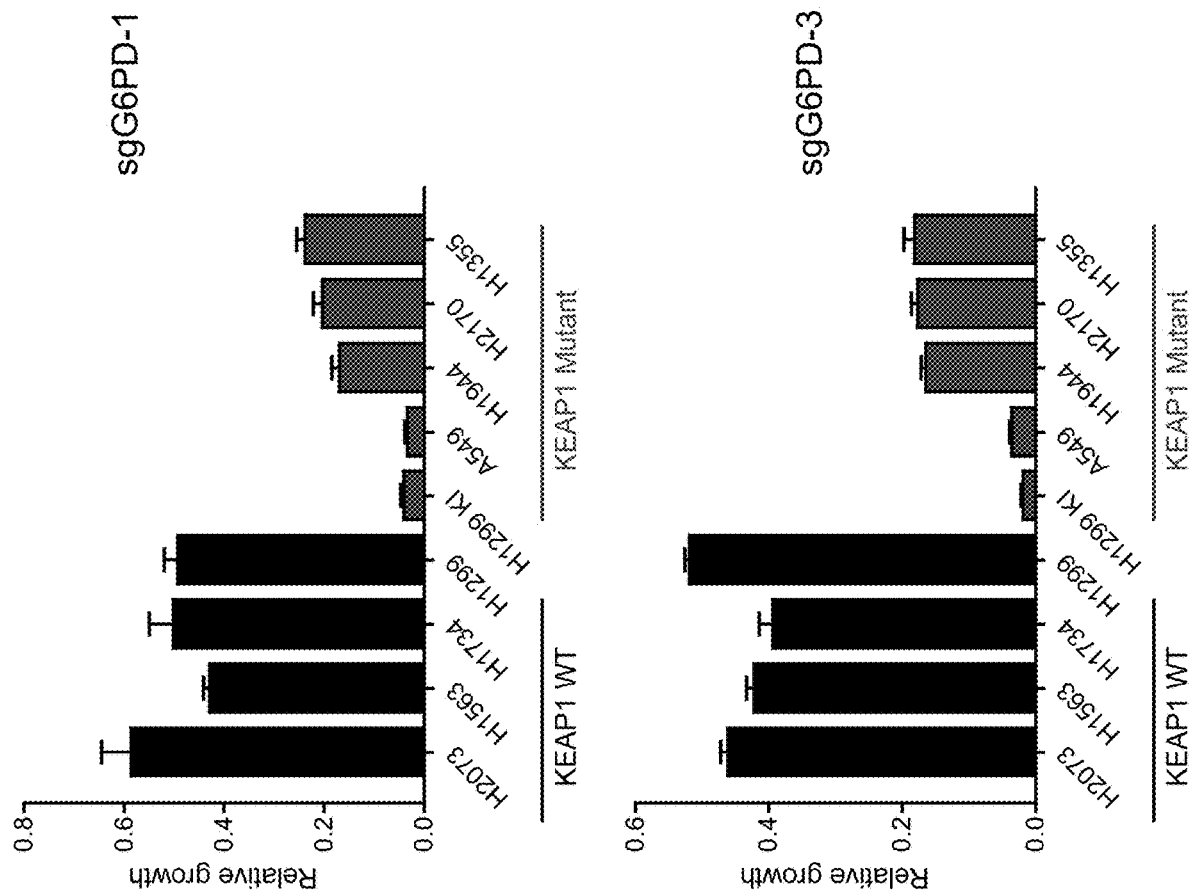

FIG. 14A through FIG. 14C depict the results of exemplary experiments demonstrating KEAP1-G6PD synergy lethality in human lung adenocarcinoma. H1299: KEAP1 wildtype human lung cancer cell; A549: KEAP1 mutant human lung cancer cell; KI: KI696, KEAP1/NRF2 inhibitor, activating NRF2. FIG. 14A and FIG. 14B depict a colony formation assay in H1299 (Keap1 wildtype), H1299+KI (NRF2 activator) and A549 (Keap1 mutants) cells transduced with sgTom or sgG6pd. FIG. 14A is the quantification of crystal violet staining (FIG. 14B). FIG. 14C depicts a quantification of cell growth of human KEAP1 wt or mutated cell lines. Cells infected with sgTom or sgG6PD, upper and bottom figure show two different sgRNA.

Figure 15A:
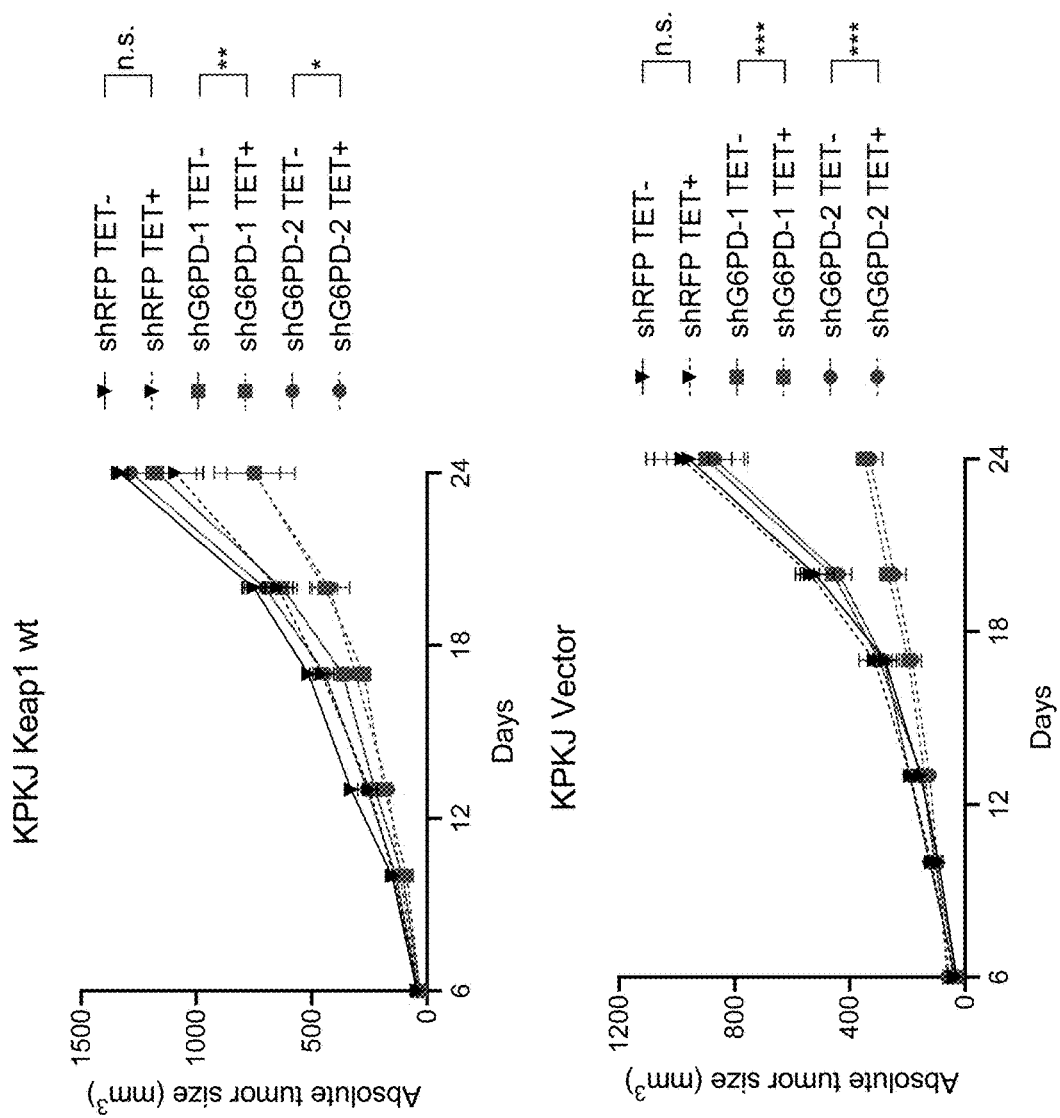
Figure 15B:
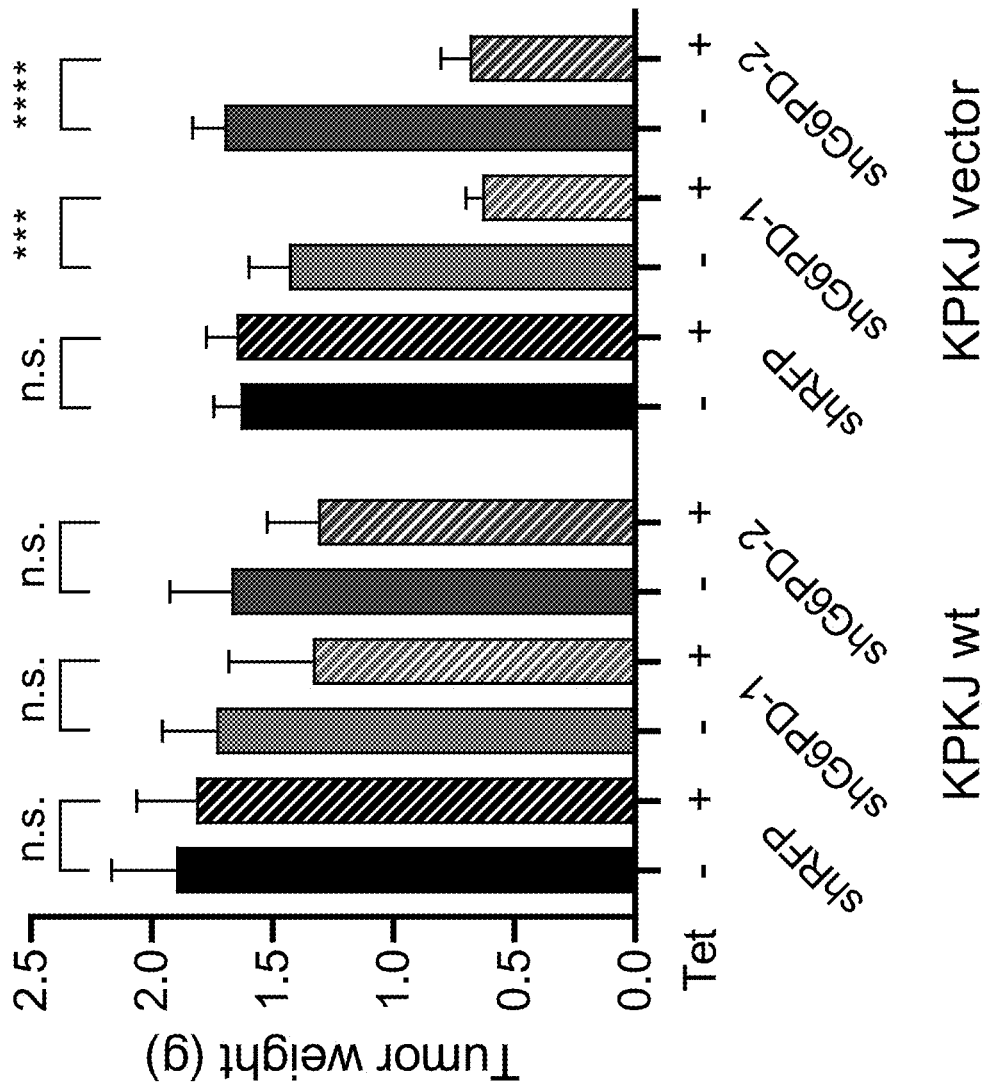

FIG. 15A and FIG. 15B depict the results of exemplary experiments demonstrating G6PD knockdown in subcutaneous models. Shown are growth curves of subcutaneous Keap1 wt/mutant tumors in B6 wildtype mice. FIG. 15A depicts tumor growth of subcutaneous tumors in animals receiving either KPKJ Keap1 wt (Keap1 wildtype) or KPKJ Vector (Keap1 KO) cells transduced with shRFP or shG6pd. Diet containing doxycyclin was supplied one week after transplantation. FIG. 15B depicts the tumor weight of subcutaneous tumors in animals receiving either KPKJ Keap1 wt (Keap1 wildtype) or KPKJ Vector (Keap1 KO) cells transduced with shRFP or shG6pd.

Figure 16:
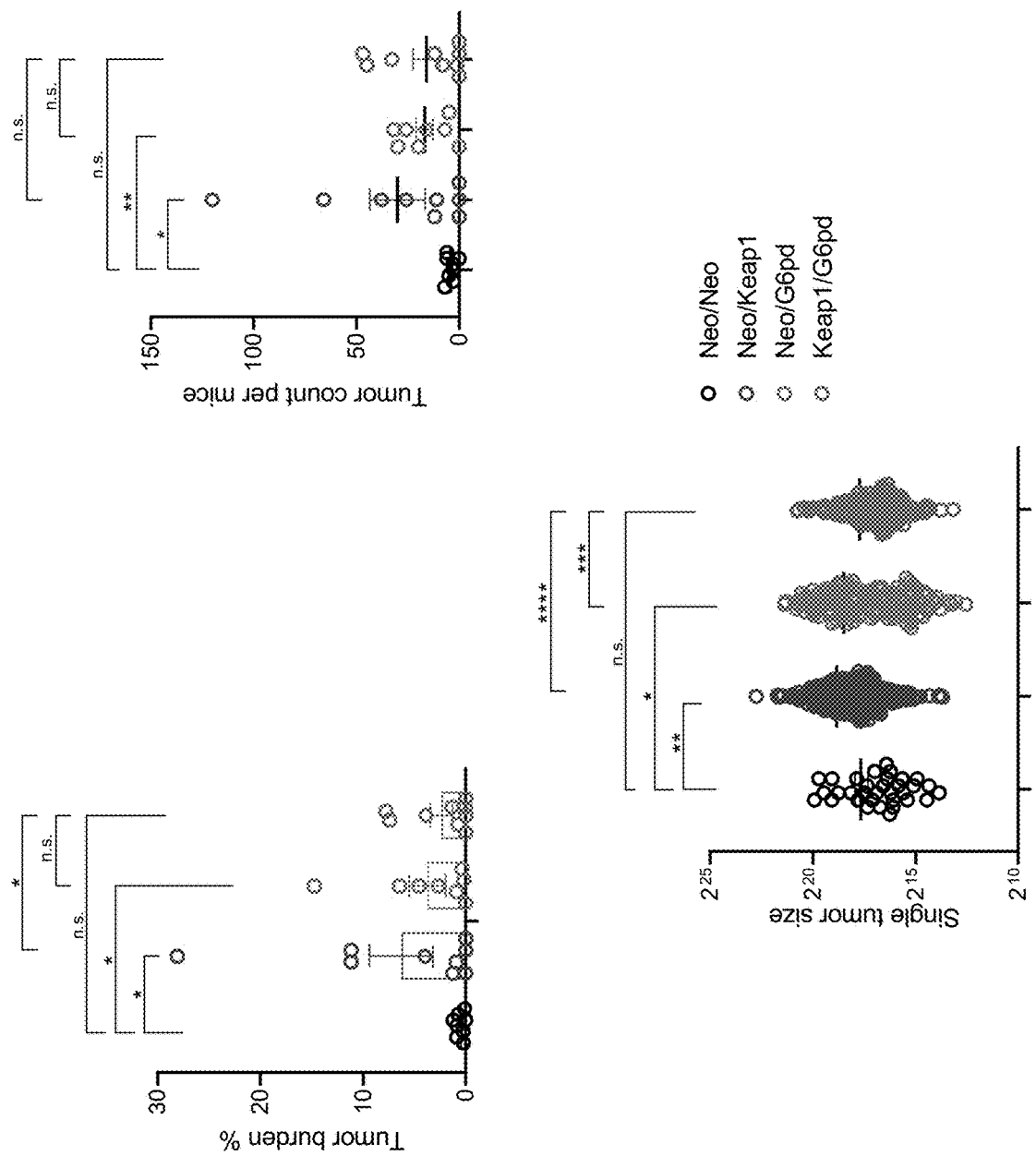

FIG. 16 depicts the results of exemplary experiments demonstrating G6PD KO in KP GEMM model. Quantification of primary lung tumor burden in sgNeo/Neo (control), sgNeo/Keap1, sgNeo/G6pd and sgKeap1/G6pd mice. KPC (Kras LSL-G12D/+; p53 fl/fl; Rosa26 LSL-Cas9) mice were intra-tracheally infected with pUSEC lentiviruses containing dual sgRNAs targeting Keap1 and G6pd.

Figure 17:
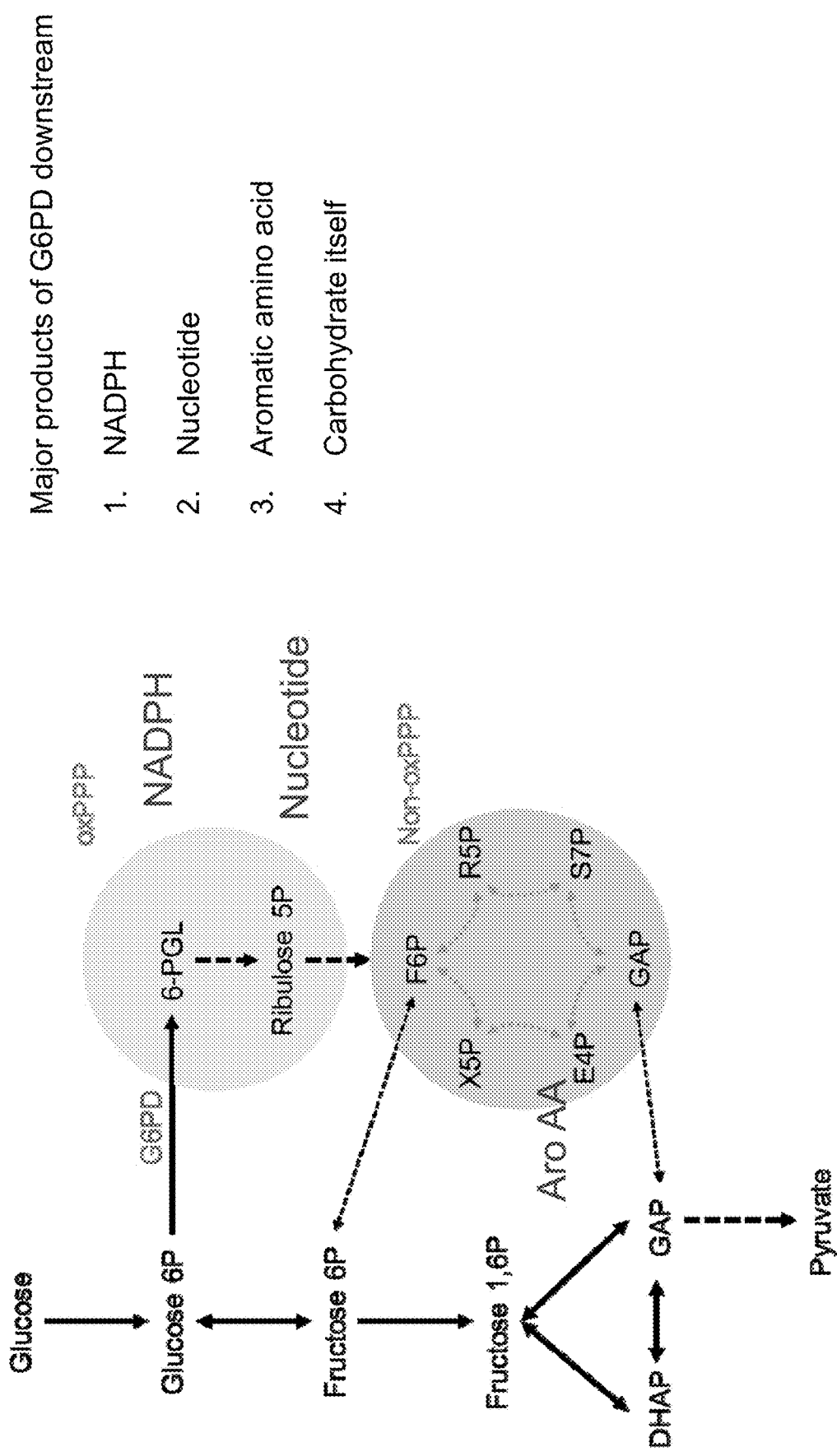

FIG. 17 depicts a schematic diagram of the pentose phosphate pathway (PPP). Classical glycolysis (light grey), oxidative PPP (light green) and non-oxidative PPP (light yellow).

Figure 18:
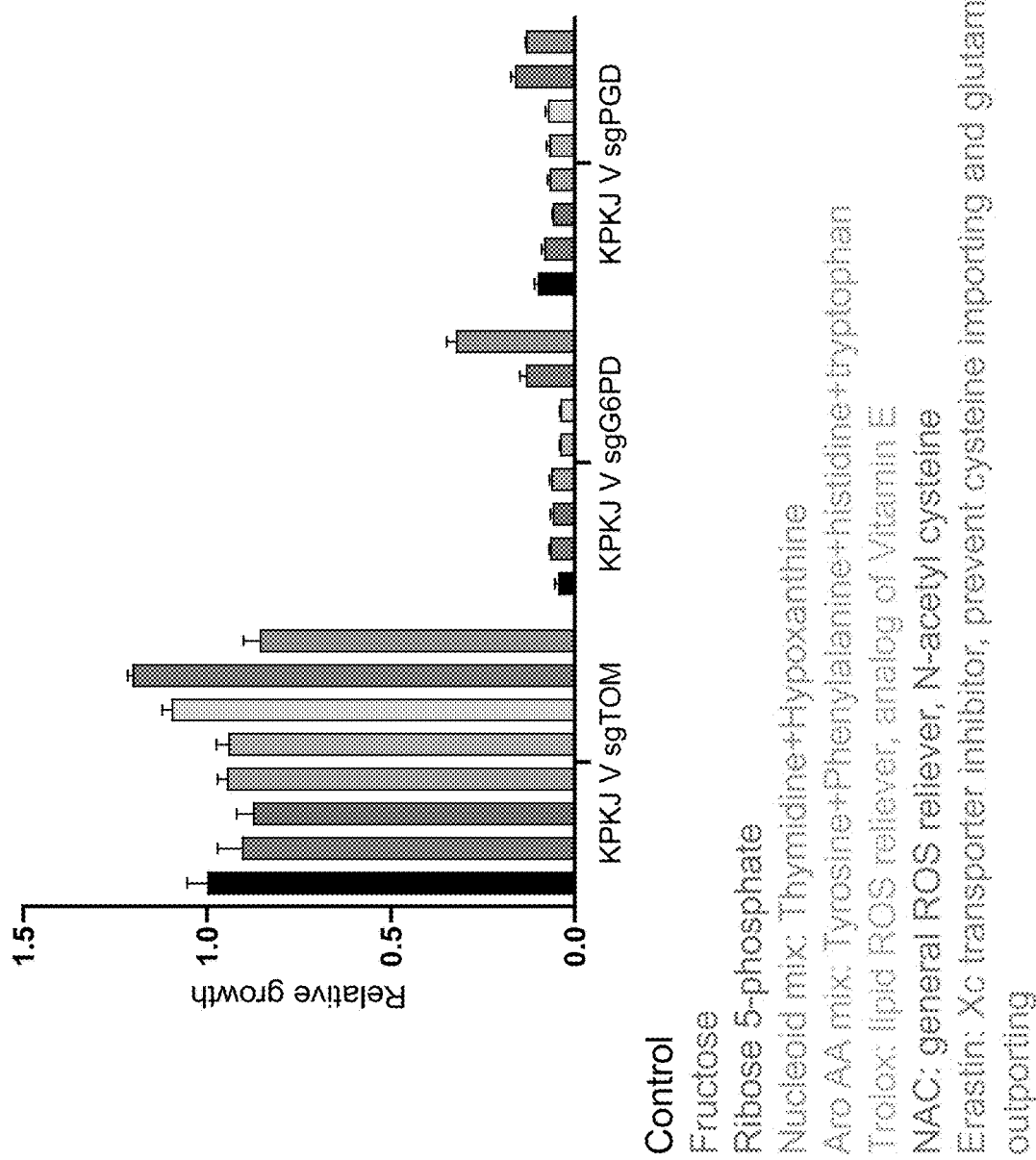
Figure 18:
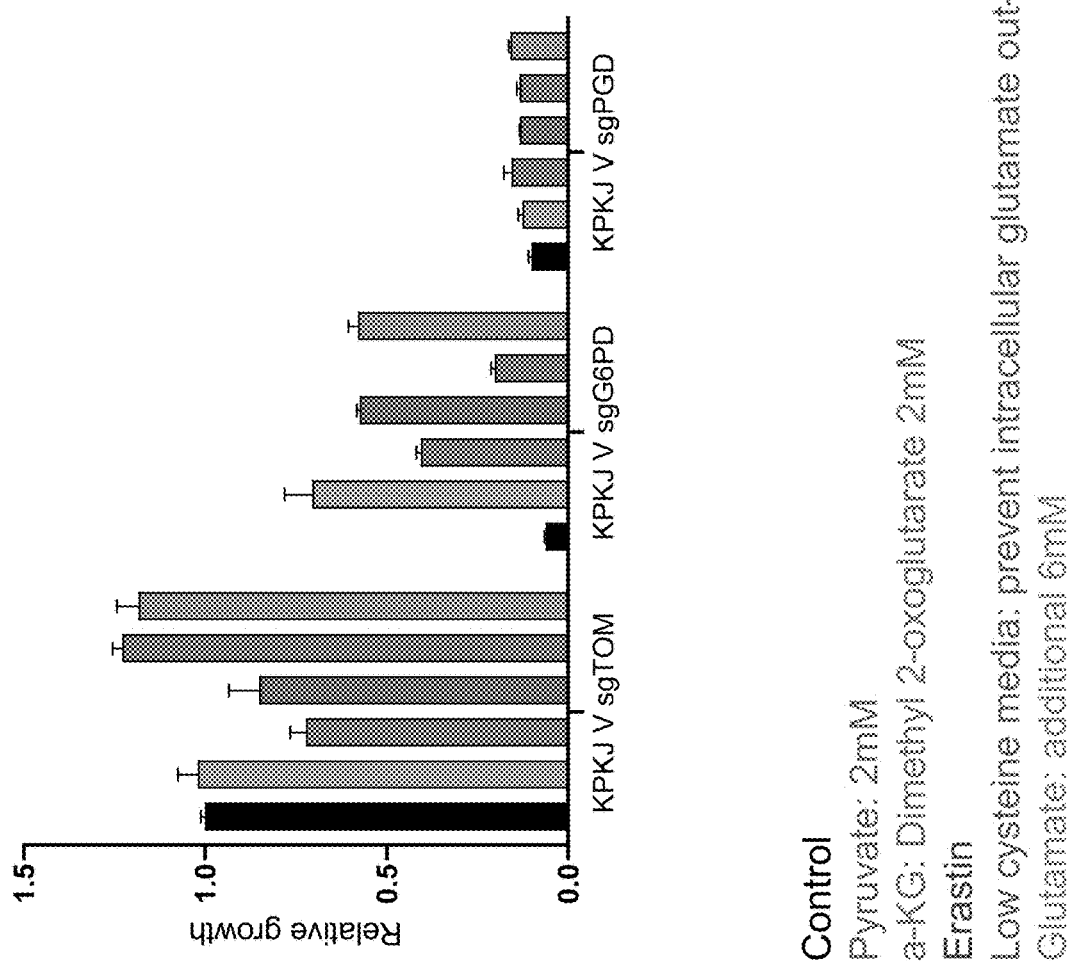

FIG. 18 depict the results of exemplary experiments demonstrating that pyruvate, a-KG and glutamate can rescue G6PD KO cells. Colony formation assay of KPKJ Vector (Keap1 KO) cells transduced with sgTom, sgG6pd and sgPGD, and rescued with several metabolites. FIG. 18 shows the quantification of crystal violet staining. G6PD KO rescue: Completely rescue: pyruvate, glutamate, a-KG; Partially rescue: Erastin, Low cysteine media; No rescue: Trolox, NAC, Aromatic amino acid, nucleotides. PGD KO rescue: Nothing rescue.

Figure 19A:
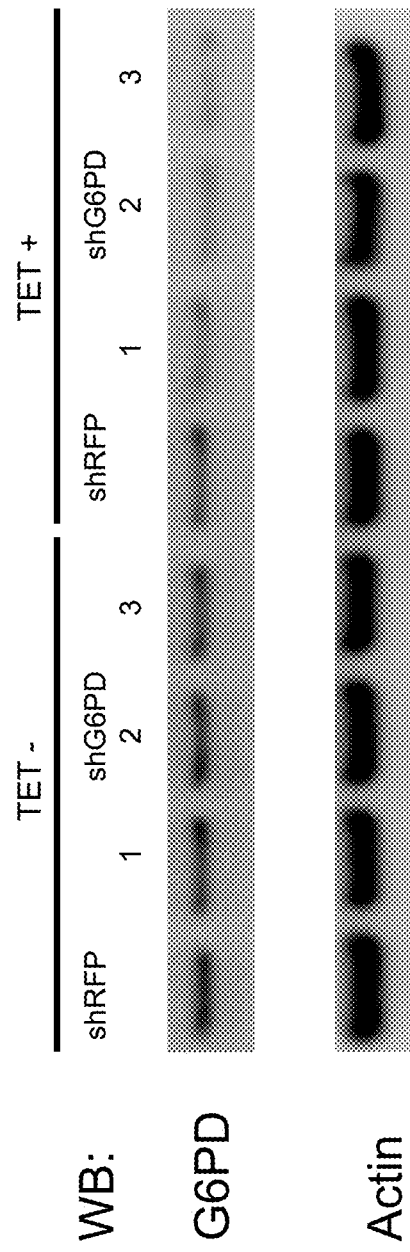
Figure 19B:
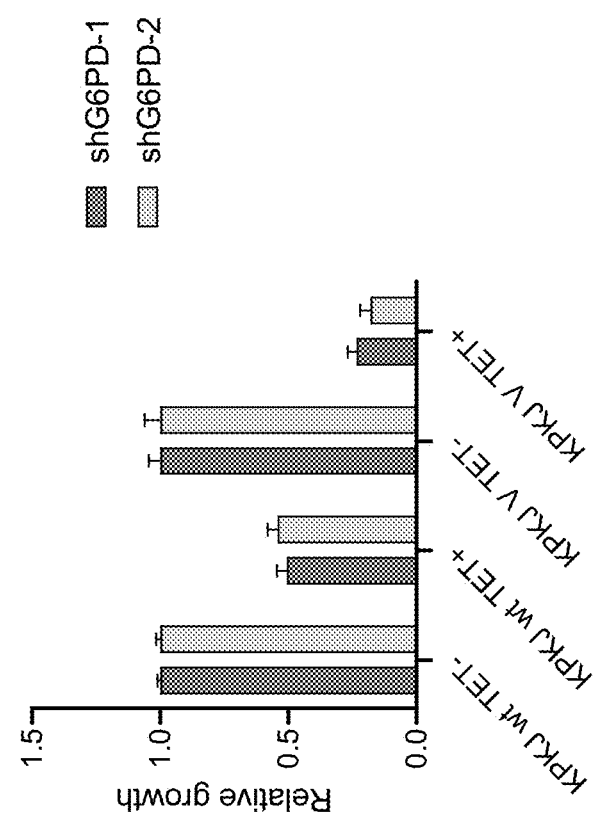

FIG. 19A and FIG. 19B depict the results of exemplary experiments demonstrating a G6PD shRNA model. FIG. 19A depicts a western blot analysis of KP cells inducible expressing shRFP (control) or shG6pd. TET+ stands for 3 days treatment of 1 ug/ml doxycycline for inducing shRNA expression. Actin as internal control. FIG. 19B depicts a colony formation assay in KPKJ wt (Keap1 wildtype) and KPKJ V (Keap1 KO) cells expressing shRFP (control) or shG6pd. TET+ stands for 3 days treatment of 1 ug/ml doxycycline for inducing shRNA expression. Because G6PD knockout is very stressful for Keap1 mutant cells, there is no G6PD KO phenotype only one week after puromycin selection. Single colonies of G6PD KO all escape knockout. An inducible TET-on shRNA knockdown system was used for in vivo subQ and some in vitro experiments. shRFP was used as a scramble control.

Figure 20:
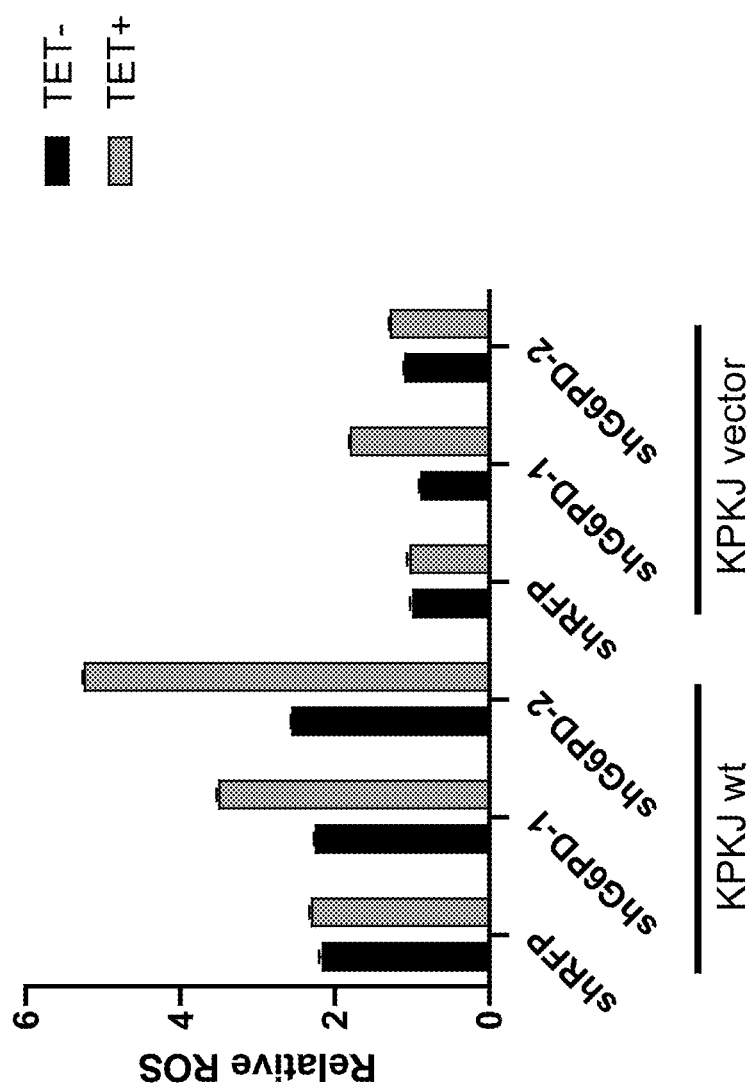

FIG. 20 depict the results of exemplary experiments demonstrating the quantification of cell ROS level in KPKJ wt (Keap1 wildtype) and KPKJ V (Keap1 KO) cells expressing shRFP (control) or shG6pd. TET+ stands for 3 days treatment of 1 μg/ml doxycycline for inducing shRNA expression. G6PD knockdown induces more ROS in Keap1 wildtype cells. Keap1 mutants show lower cell ROS. ROS level was measured by DCFCA assay. G6PD KO induces accumulation of ROS in Keap1 wildtype cells. Measured by FACS (DCFCA assay.) TET treatment 4 day before measuring. $H_2O_2$ positive control is about 200-fold increase.

Figure 21:
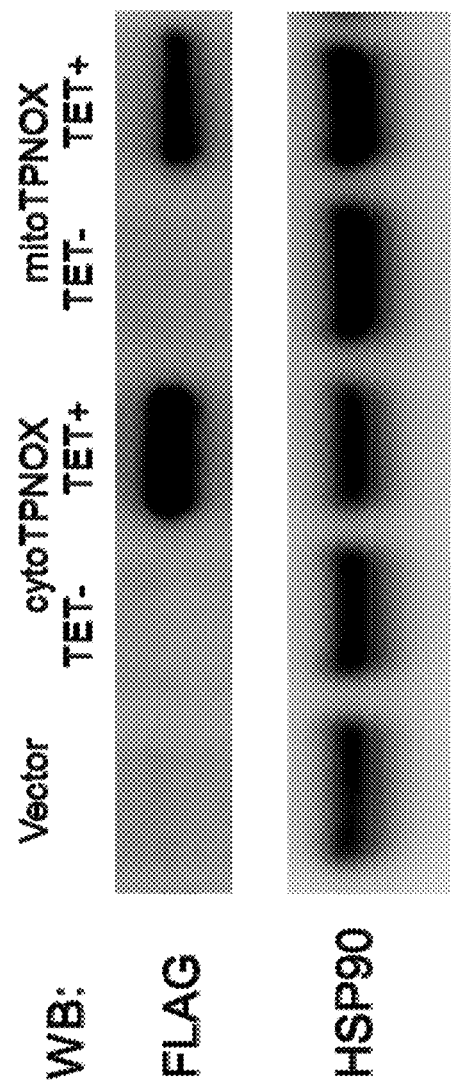

FIG. 21 depicts a western blot analysis of KPKJ wt cells inducible expressing Vector (control), cytoplasma TPNOX or mitochondria TPNOX. TPNOX protein is fused with Flag tag for detection. TET+ stands for 3 days treatment of 1 μg/ml doxycycline for inducing TPNOX expression, HSP90 as internal control. TPNOX is a water-soluble NADPH oxidase (nchembio.2454), which depletes NADPH, inducible cytoplasmic TPNOX and mitochondria TPNOX overexpressing cell lines were generated. Flag tag is fused with TPNOX.

Figure 22A:
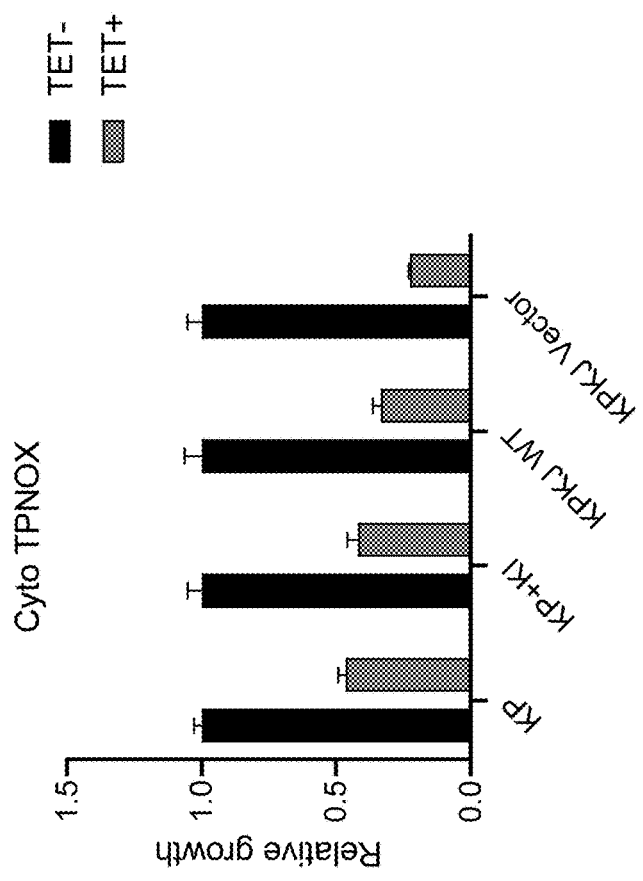
Figure 22B:
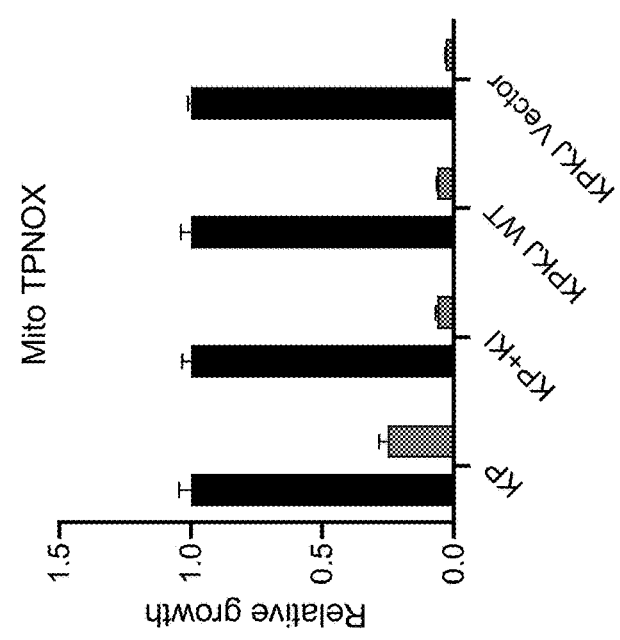

FIG. 22A and FIG. 22B depict the results of exemplary experiments demonstrating that NADPH depletion affects cell growth. FIG. 22A depicts a colony formation assay in KP (Keap1 wildtype), KP+KI (NRF2 activator), KPKJ wt (Keap1 wildtype) and KPKJ V (Keap1 KO) cells expressing mitochodria TPNOX. TET+ stands for 3 days treatment of 1 μg/ml doxycycline for inducing TPNOX expression. FIG. 22B depicts a colony formation assay in KP (Keap1 wildtype), KP+KI (NRF2 activator), KPKJ wt (Keap1 wildtype) and KPKJ V (Keap1 KO) cells expressing cytoplasma TPNOX. TET+ stands for 3 days treatment of 1 μg/ml doxycycline for inducing TPNOX expression. Mito TPNOX induction increases more growth disadvantage in Keap1 mutants, cyto TPNOX don't have big difference. Both Keap1 wt and mutant cells tolerate cyto NADPH depletion than mito NADPH depletion. Virus titer for different cell lines are control as the same. Tpnox expression level are confirmed as same between by western blot.

Figure 23A:
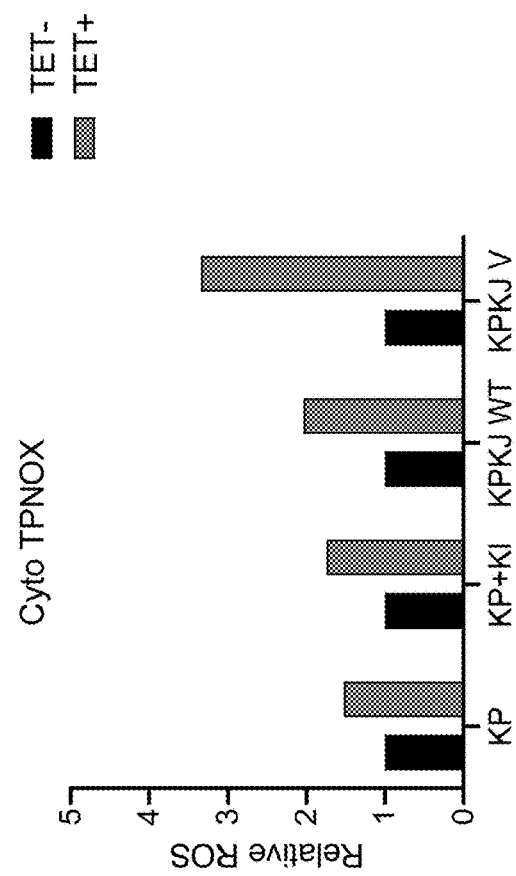
Figure 23B:
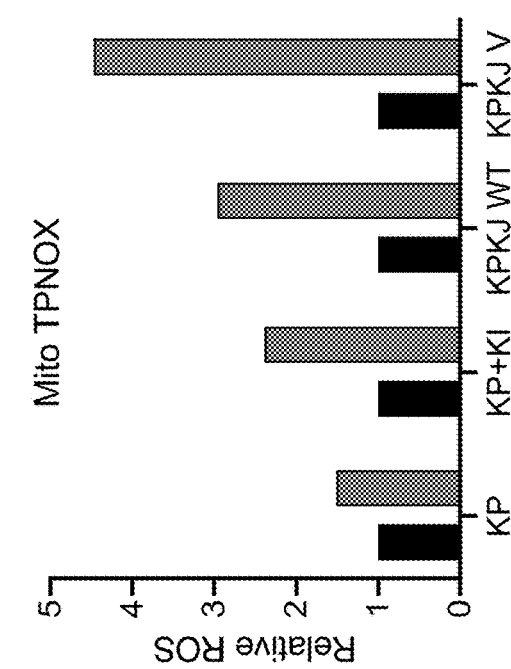

FIG. 23A and FIG. 23B depict the results of exemplary experiments demonstrating that NADPH depletion affects cell growth. FIG. 23A depicts a quantification of cell ROS level in KP (Keap1 wildtype), KP+KI (NRF2 activator), KPKJ wt (Keap1 wildtype) and KPKJ V (Keap1 KO) cells expressing mitochodria TPNOX. TET+ stands for 3 days treatment of 1 μg/ml doxycycline for inducing TPNOX expression. ROS level was measured by DCFCA assay. FIG. 23B depicts a quantification of cell ROS level in KP (Keap1 wildtype), KP+KI (NRF2 activator), KPKJ wt (Keap1 wildtype) and KPKJ V (Keap1 KO) cells expressing cytoplasma TPNOX. TET+ stands for 3 days treatment of 1 μg/ml doxycycline for inducing TPNOX expression. ROS level was measured by DCFCA assay. Mito NADPH depletion induces more ROS than cyto NADPH depletion. TPNOX induction increases more ROS in Keap1 mutants. Enzymes consuming NADPH in Keap1 mutant cells are also much higher expressed and active, leading to a bigger shortage of NADPH.

Figure 24:
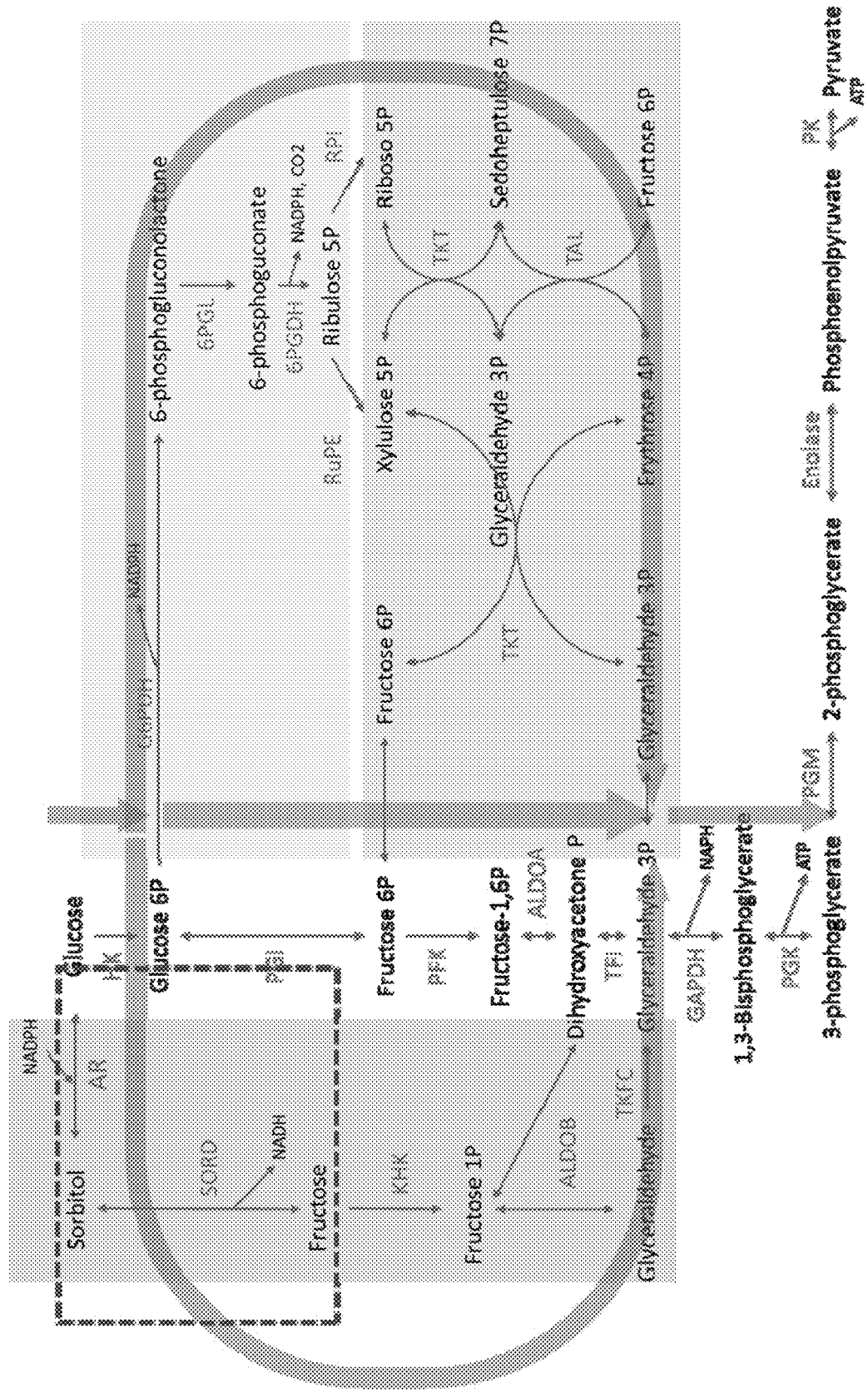
Figure 24:
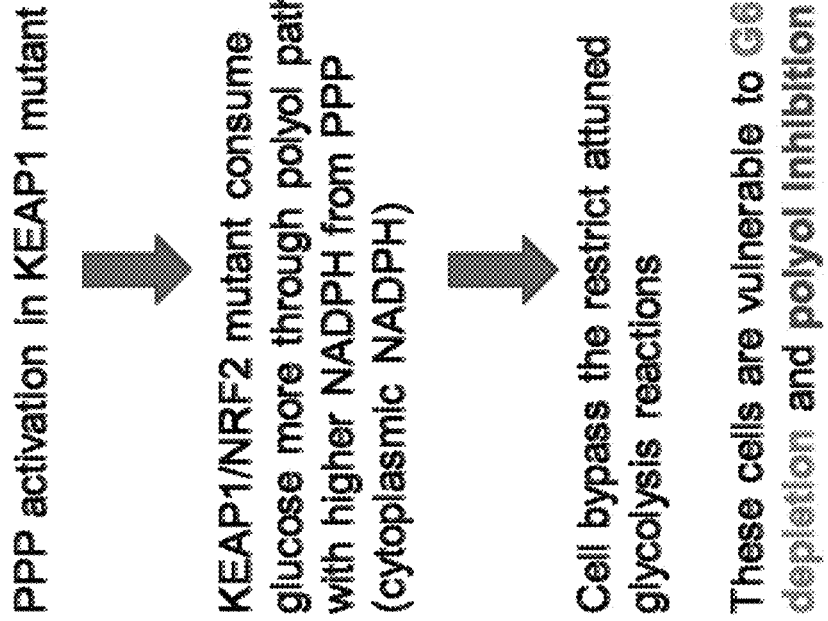

FIG. 24 depicts a Keap1 and polyol pathway schematic map. The schematic map demonstrates how the polyol pathway is connected with Keap1 and the PPP pathway.

Figure 25A:
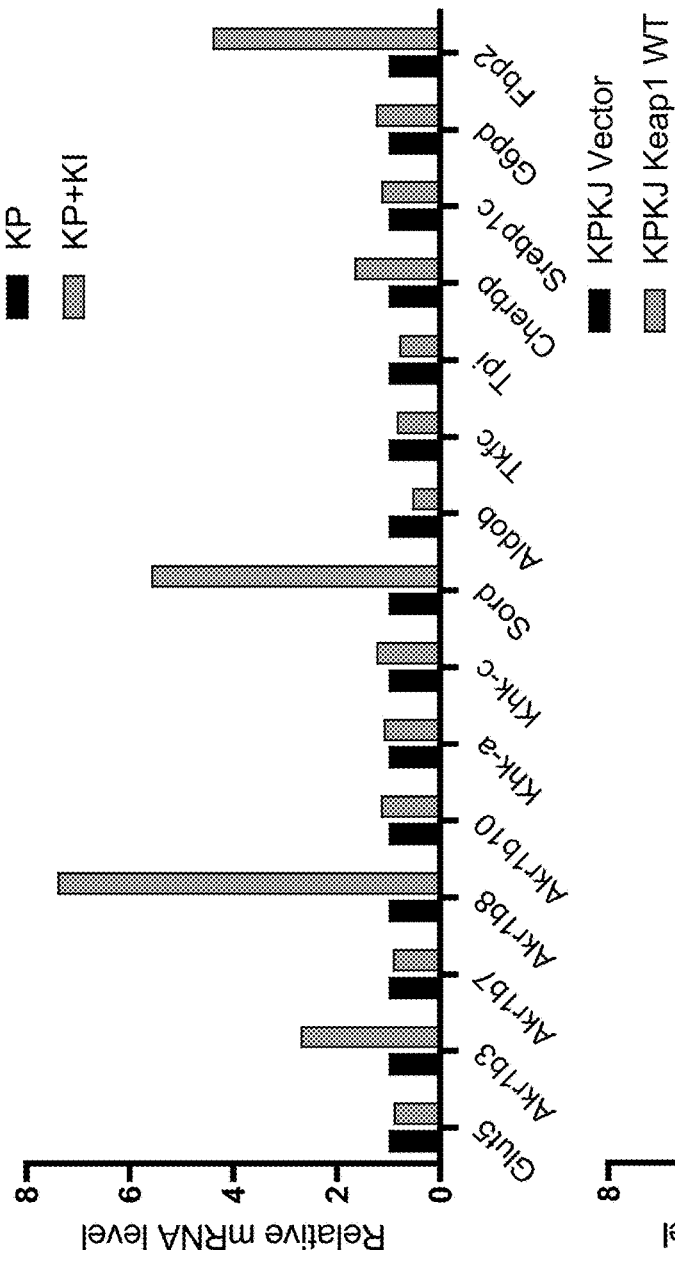
Figure 25B:
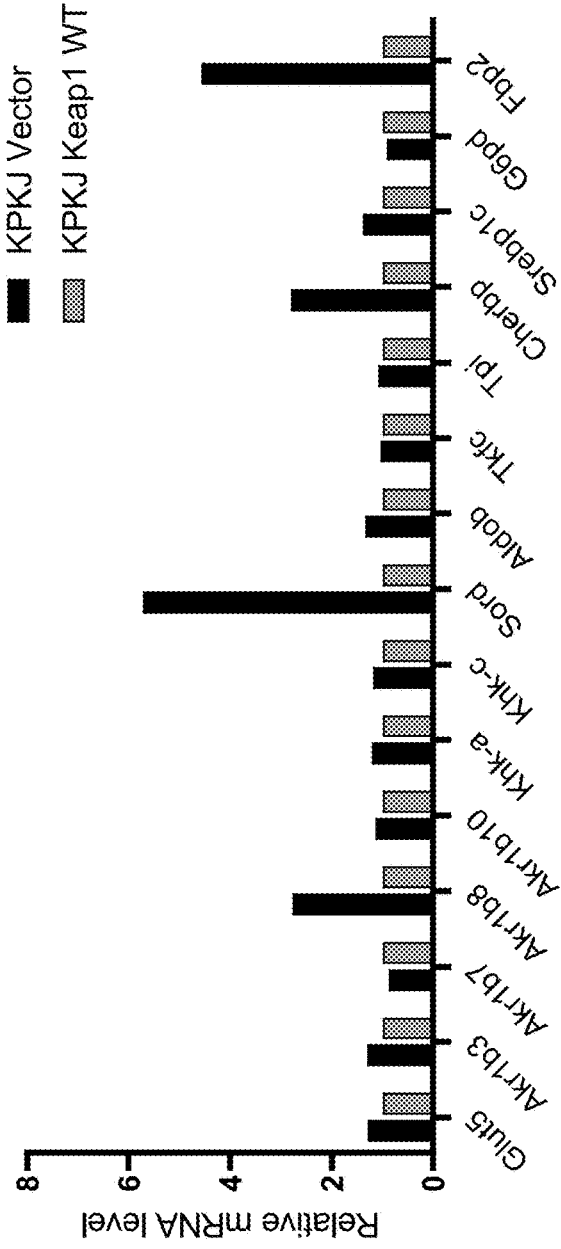

FIG. 25A and FIG. 25B depict the results of exemplary experiments demonstrating polyol pathway related enzyme expression. FIG. 25A depicts a quantitative PCR (qPCR) analysis of polyol pathway gene in KP (Keap1 wildtype), KP+KI (NRF2 activator) cells. RNA expression normalized to Gapdh. FIG. 25B depicts a quantitative PCR (qPCR) analysis of polyol pathway gene in KPKJ wt (Keap1 wildtype) and KPKJ V (Keap1 KO) cells. RNA expression normalized to Gapdh. Akr1b1/Akr1b8/Sord/Cherbp are confirmed as NRF2 substrate. Glut5 is not regulated by NRF2, thus the growth advantage in media with fructose is contributed by higher fructose utilization rate rather than higher transport activity.

Figure 26:
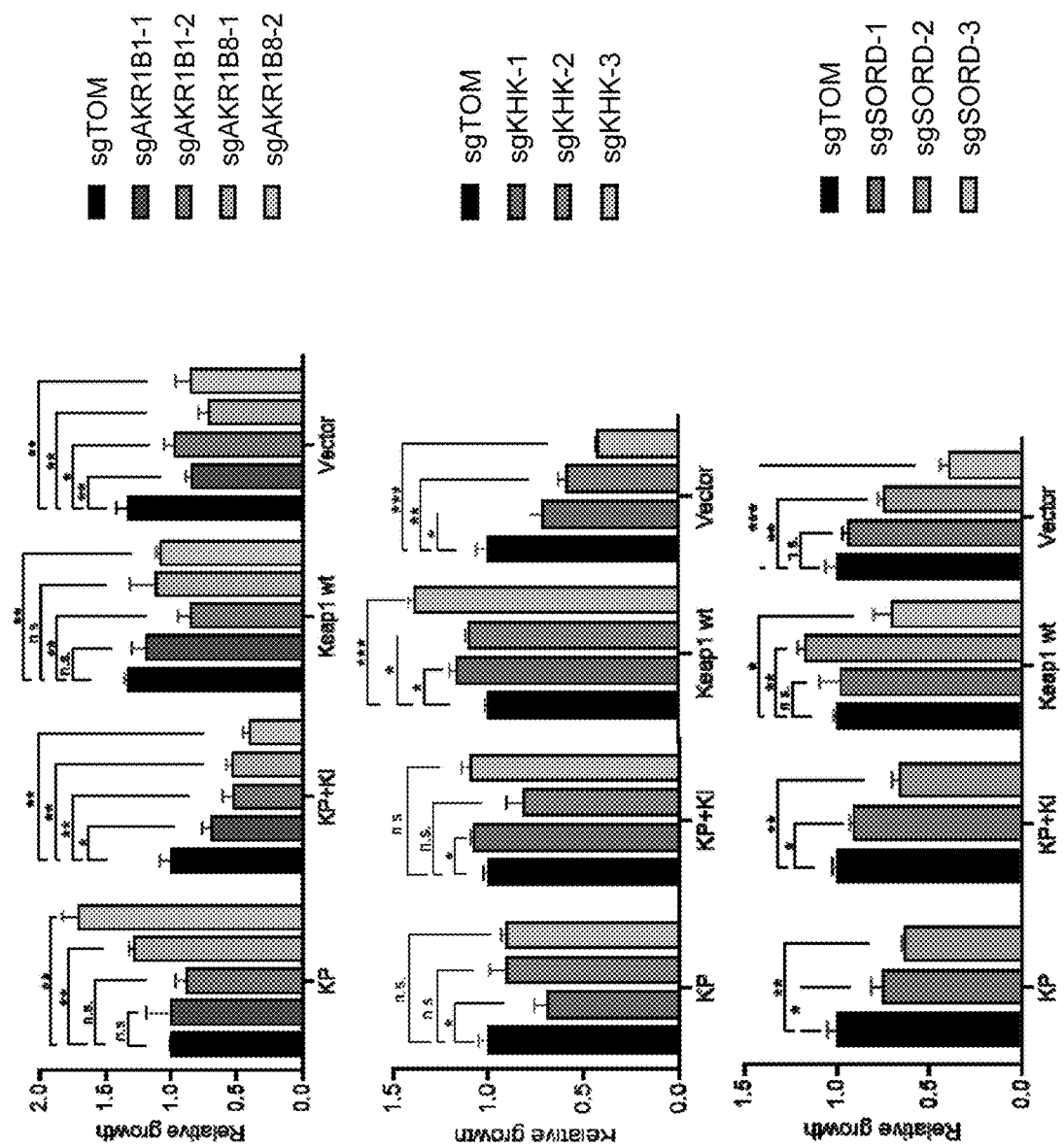

FIG. 26 depicts the results of exemplary experiments demonstrating that KEAP1 mutants are sensitive to polyol enzymes KO. Shown is a quantification of colony formation assay of KP (Keap1 wildtype), KP+KI (NRF2 activator), KPKJ wt (Keap1 wildtype) and KPKJ V (Keap1 KO) cells transduced with sgTom or sgAkr1b1/Akr1b8/Khk/Sord.

Figure 27:
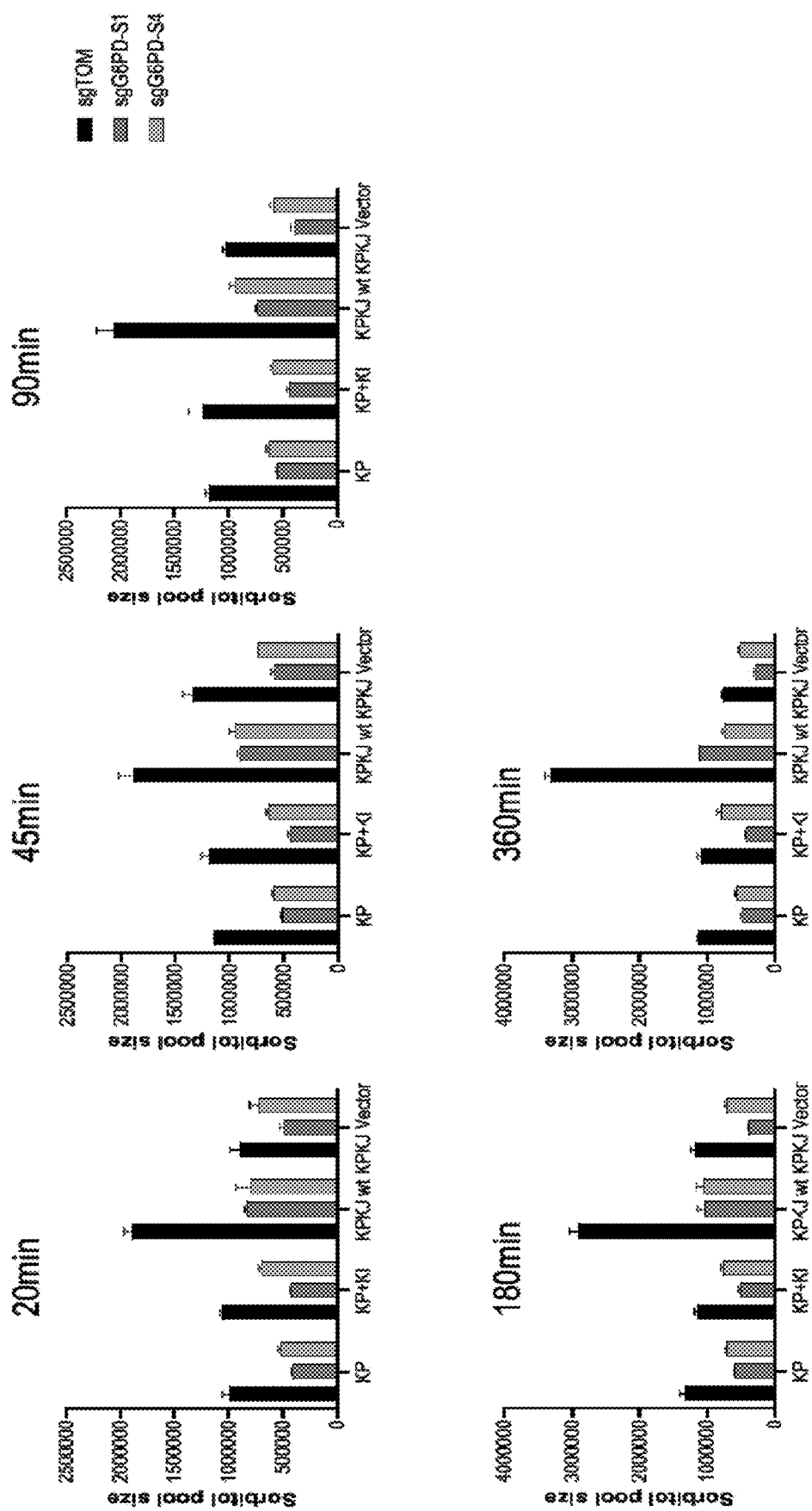

FIG. 27 depicts the results of exemplary experiments demonstrating a mass isotopomer analysis of sorbitol pool-size in KP (Keap1 wildtype), KP+KI (NRF2 activator), KPKJ wt (Keap1 wildtype) and KPKJ V (Keap1 KO) cells expressing sgTOM or sgG6PD, cells were cultured in RPMI media with diFBS and fully labeled 13C glucose for 20/45/90/180/360 min. Measured by GCMS, samples are derivatized with TMS, and normalized with cell count and internal control.

Figure 28:
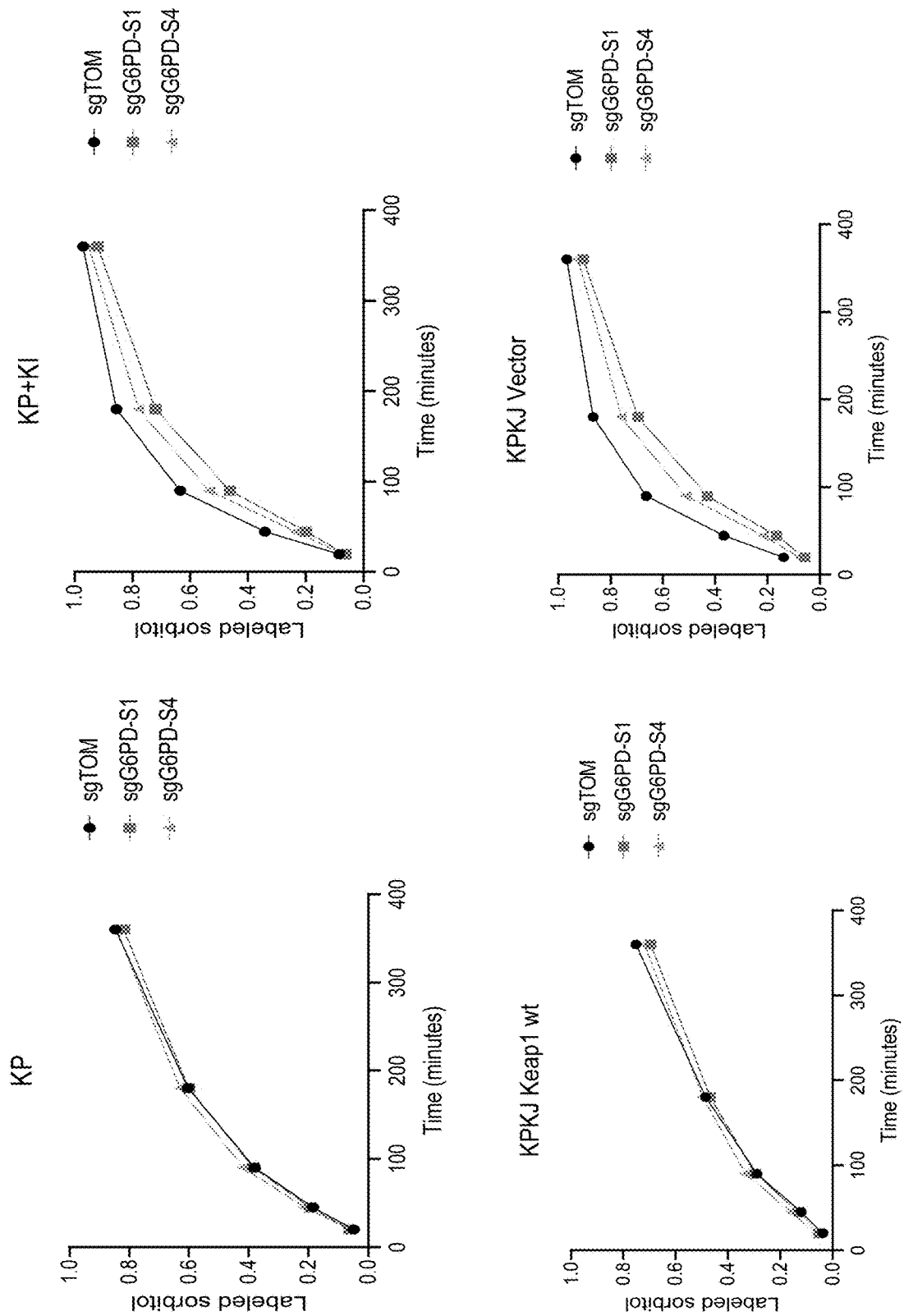

FIG. 28 depicts the results of exemplary experiments demonstrating a mass isotopomer analysis of sorbitol labeling percentage in KP (Keap1 wildtype), KP+KI (NRF2 activator), KPKJ wt (Keap1 wildtype) and KPKJ V (Keap1 KO) cells expressing sgTOM or sgG6PD, cells were incubated in RPMI media with diFBS and fully labeled 13C glucose for 20/45/90/180/360 min. Measured by GCMS, samples are derivatized with TMS, and normalized with cell count and internal control.

Figure 29:
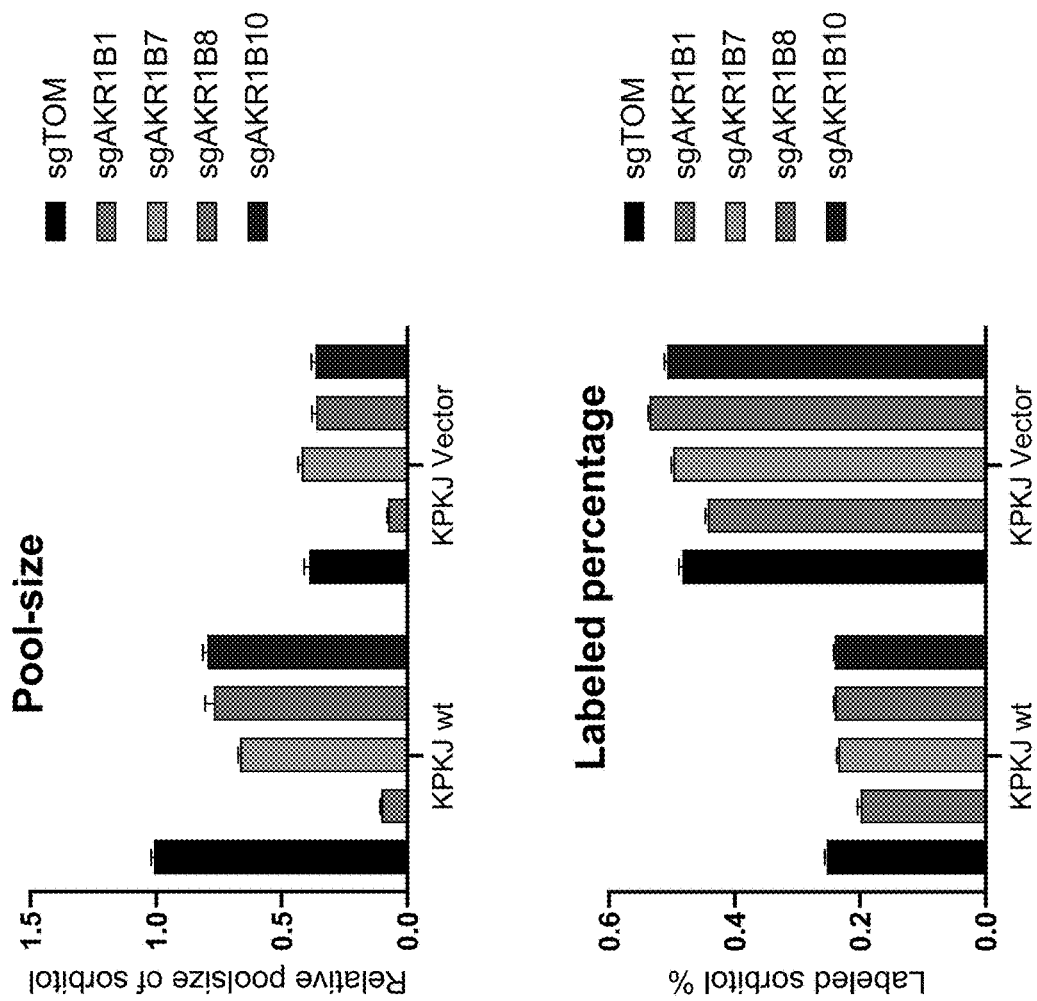

FIG. 29 depicts the results of exemplary experiments demonstrating a mass isotopomer analysis of sorbitol pool-size and labeling percentage in KPKJ wt (Keap1 wildtype) and KPKJ V (Keap1 KO) cells expressing sgTOM or sgAkr1b1/1b7/1b8/1b10, cells were cultured in RPMI media with diFBS and fully labeled 13C glucose for 45 minutes. sgRNA efficiency is validated by qPCR. Measured by GCMS, samples are derivatized with TMS, and normalized with cell count and internal control.

Figure 30:
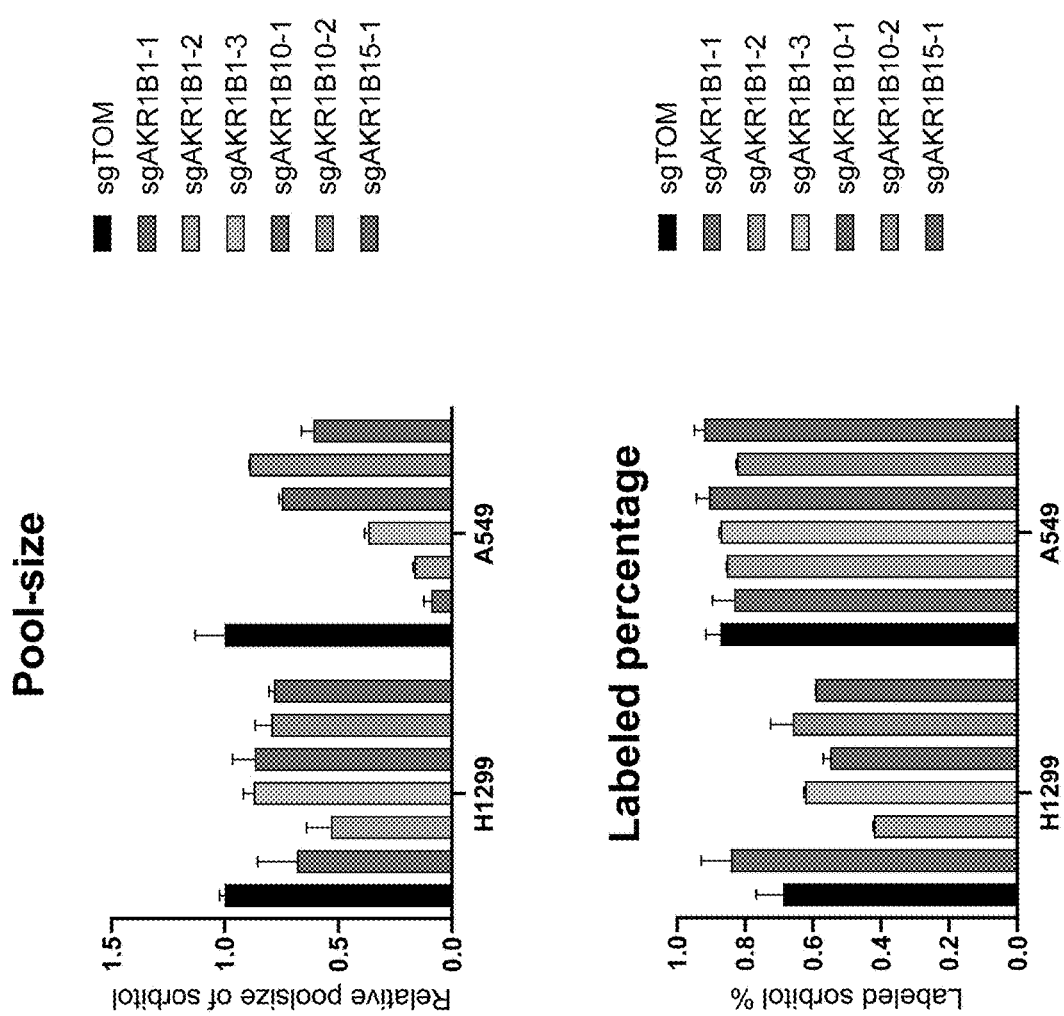

FIG. 30 depicts the results of exemplary experiments demonstrating a mass isotopomer analysis of sorbitol pool-size and labeling percentage in H1299 (Keap1 wildtype) and A549 (Keap1 KO) cells expressing sgTOM or sgAKR1B1/1B10/1B15, cells were cultured in RPMI media with diFBS and fully labeled 13C glucose for 45 minutes. sgRNA efficiency is validated by qPCR. Measured by GCMS, samples are derivatized with TMS, and normalized with cell count and internal control.

Figure 31:
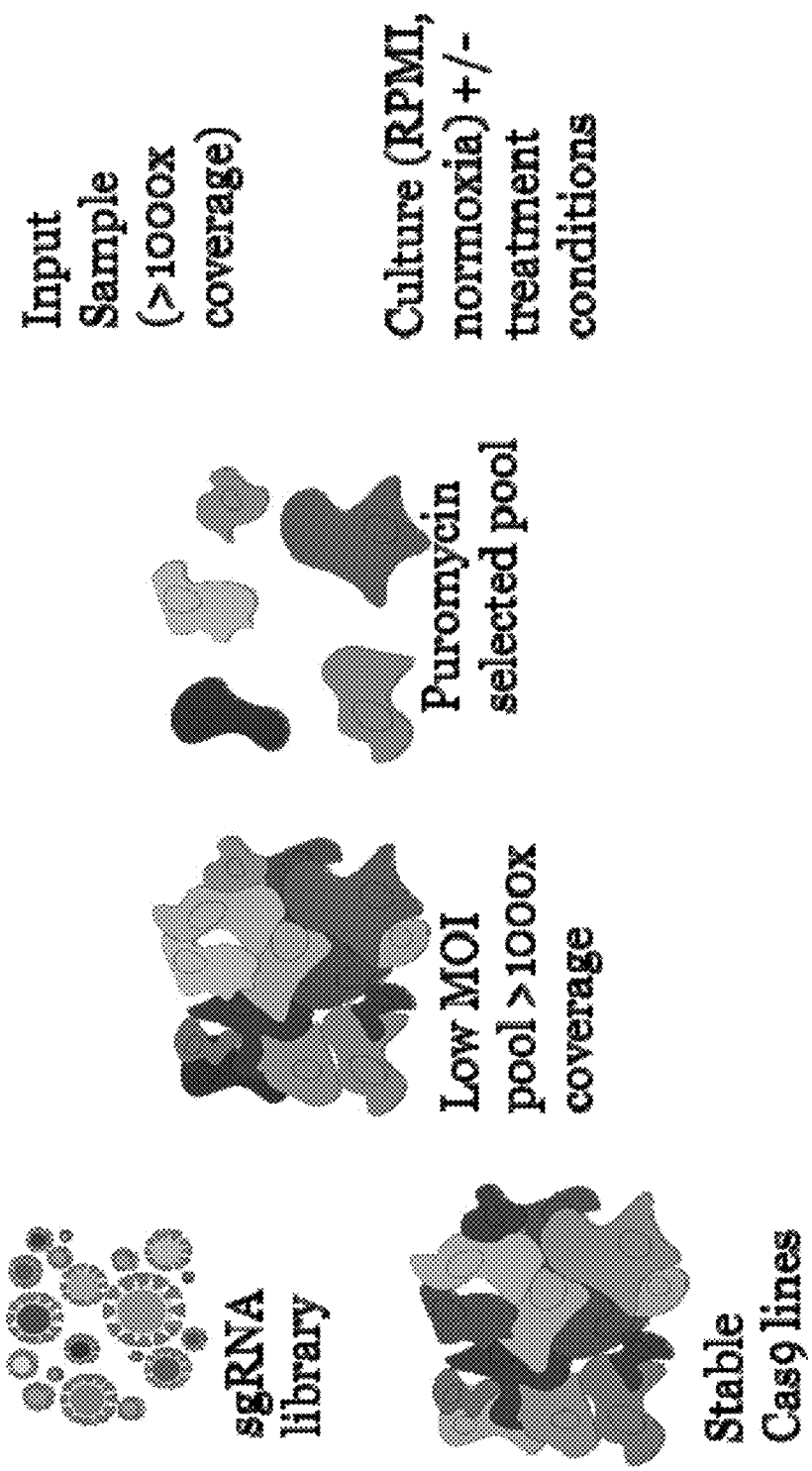

FIG. 31 depicts a general experimental work schematic. ~200 genes targeted, with 5 guides per gene. Targets represent broad sampling of metabolic pathways (low representation from each pathway).

Figure 32:
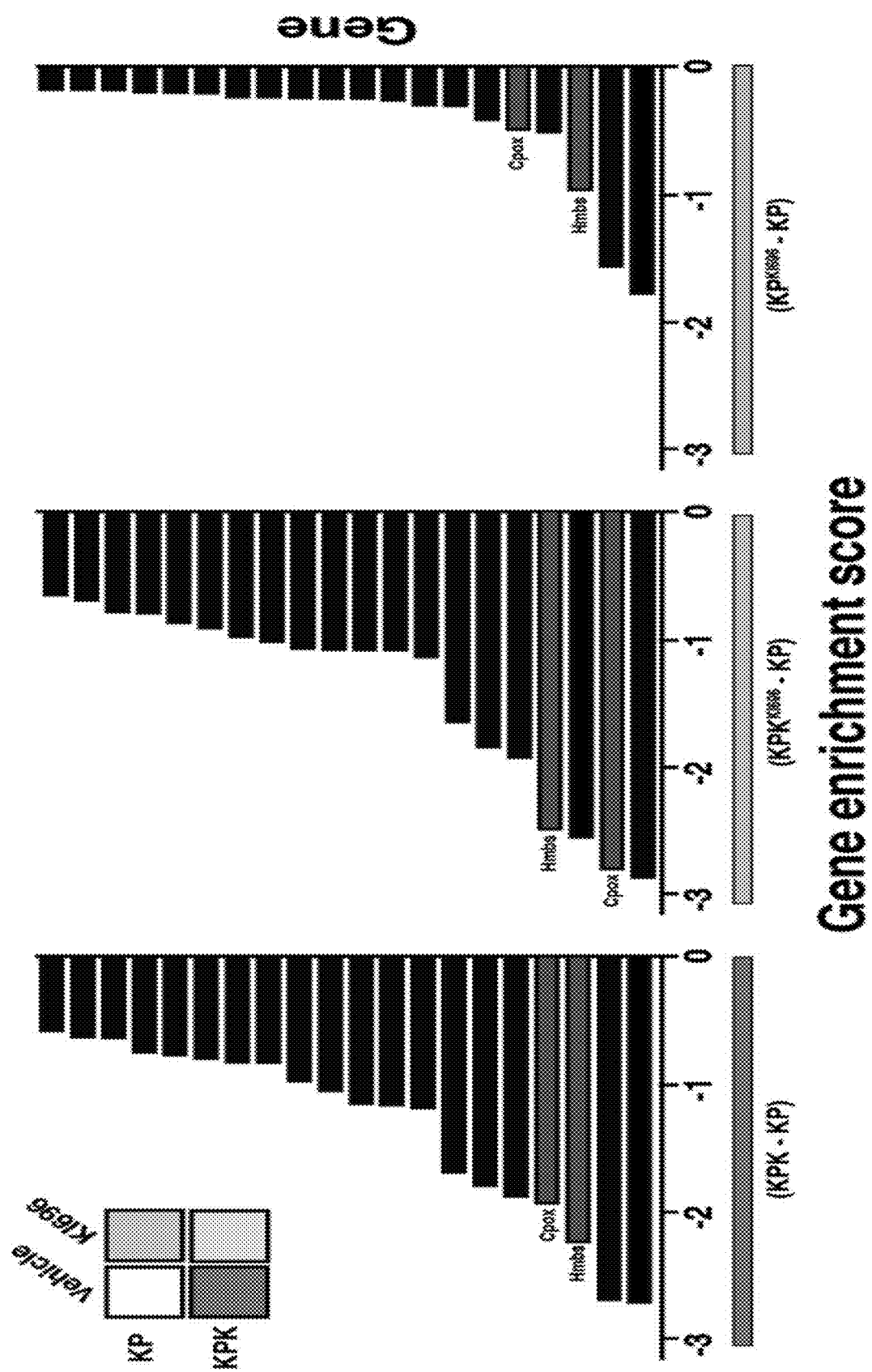

FIG. 32 depicts the results of exemplary experiments demonstrating a heme biosynthesis genes are synthetic lethal in Keap1-mutant and Nrf2-activated KP LUAD cells. Top 15 scoring genes from a metabolic CRISPR/Cas9 screen in KP vs KPK mouse LUAD cell lines. Gene enrichment score shows log2 fold change in final guide representation in KPK relative to KP cells.

Figure 33:
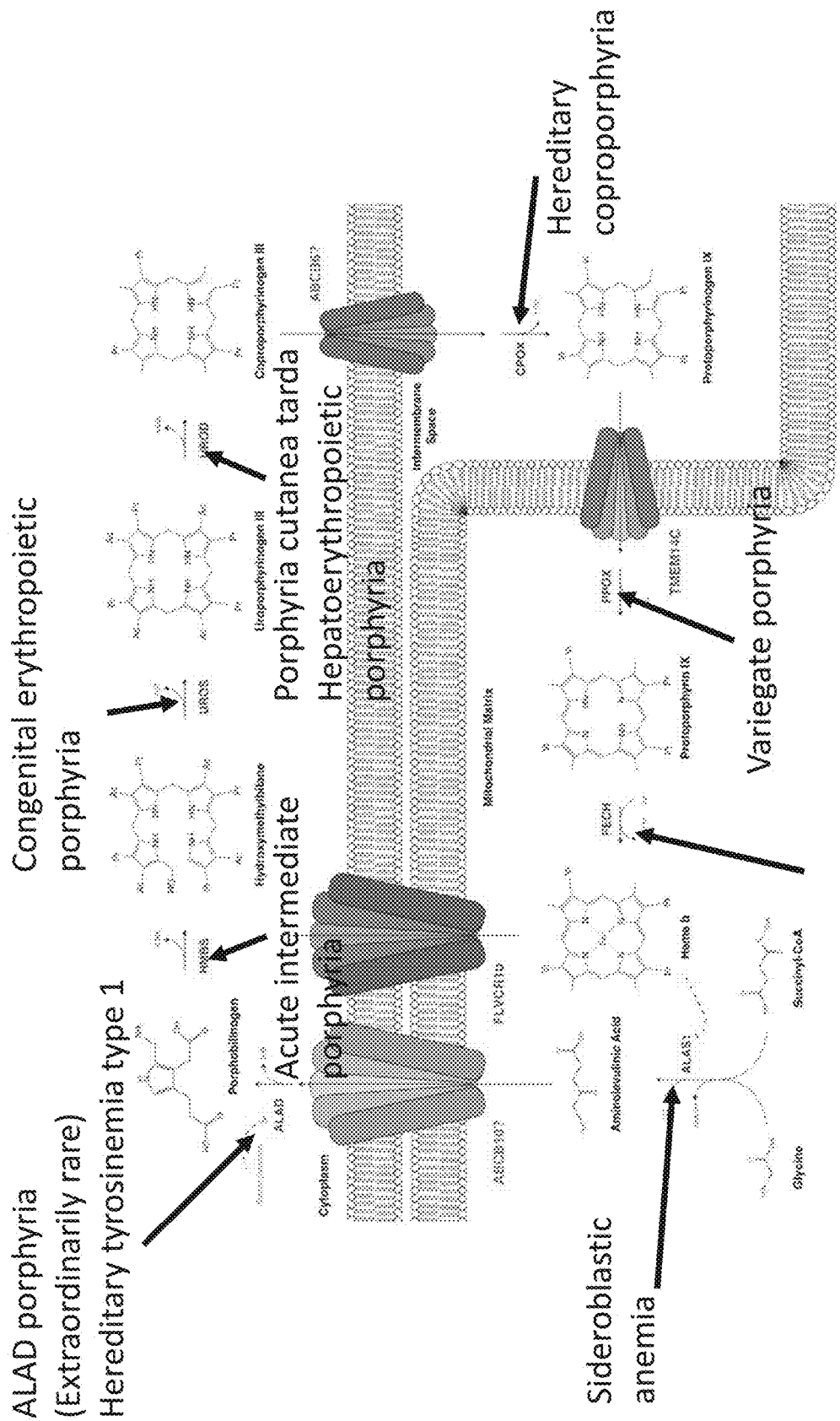

FIG. 33 depicts a diagram demonstrating a schematic of the heme synthesis pathway. Blue Arrows point to the enzymes that are found mutated in humans that have the indicated porhpyrias.

Figure 34A:
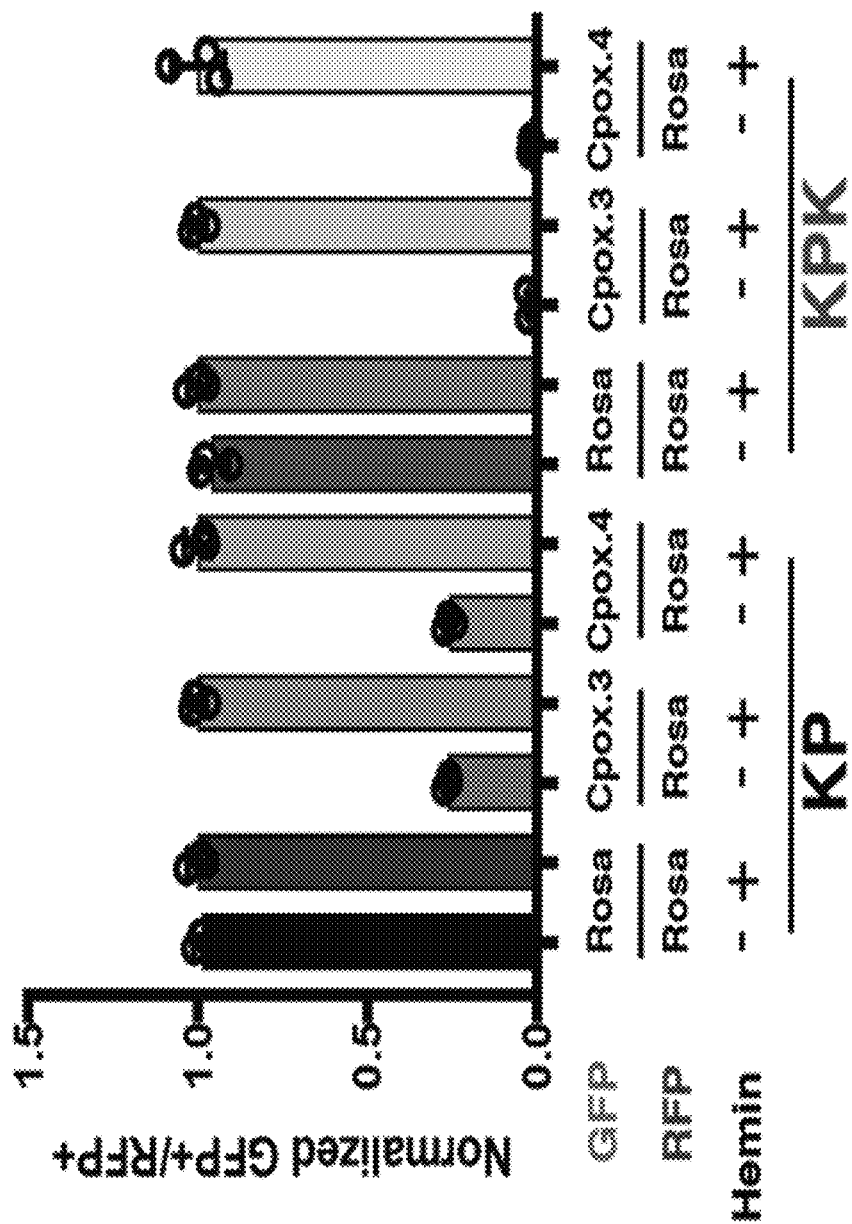
Figure 34B:
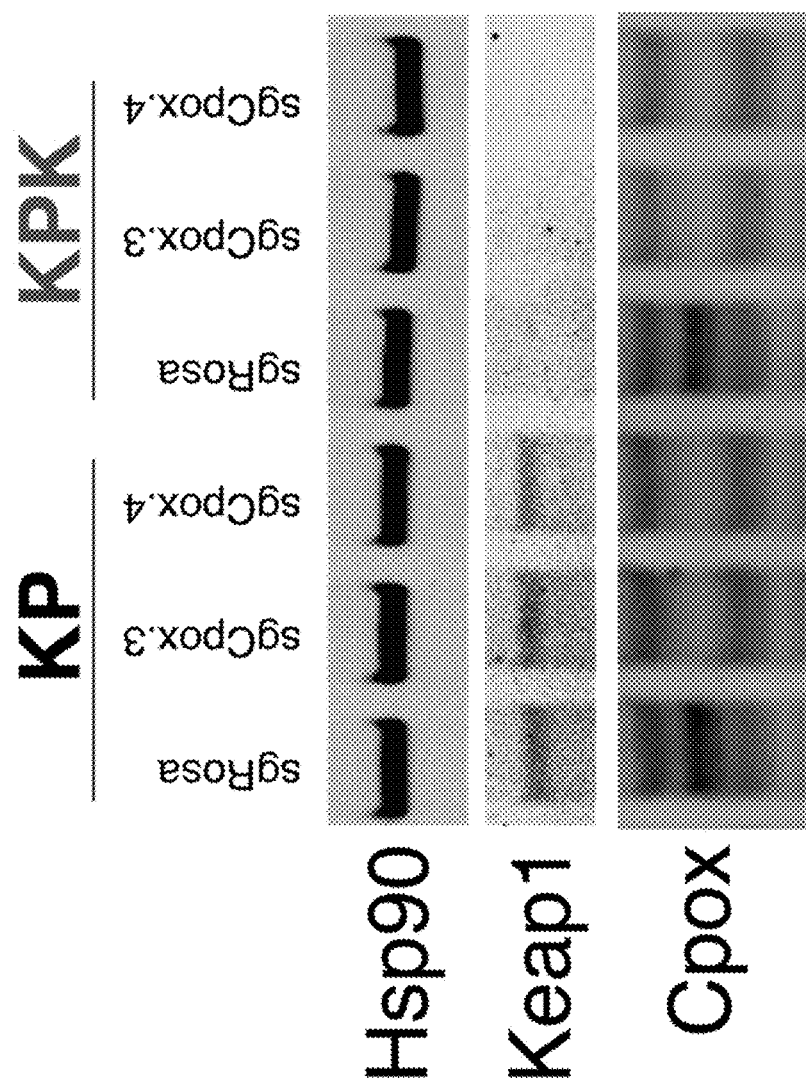

FIG. 34A and FIG. 34B depict the results of exemplary experiments demonstrating that Keap1-mutant cells are more sensitive to heme pathway inhibition in a competitive growth assay. FIG. 34A depicts a competitive growth assay of KP/KPK cells carrying one of two independent guide RNAs against Cpox or the Rosa locus (control) after 11 days of co-culture. FIG. 34B depicts a western bot validation of Cpox deletion.

Figure 35A:
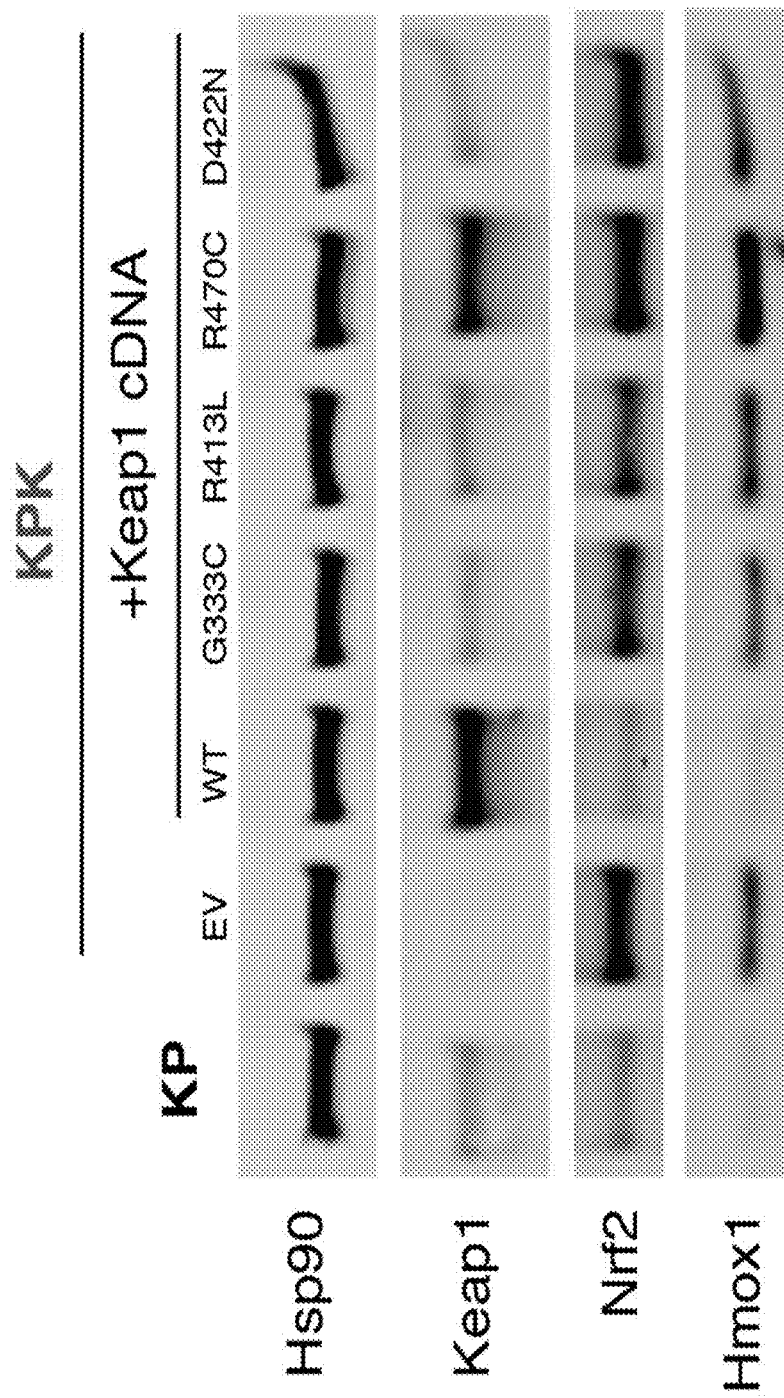
Figure 35B:
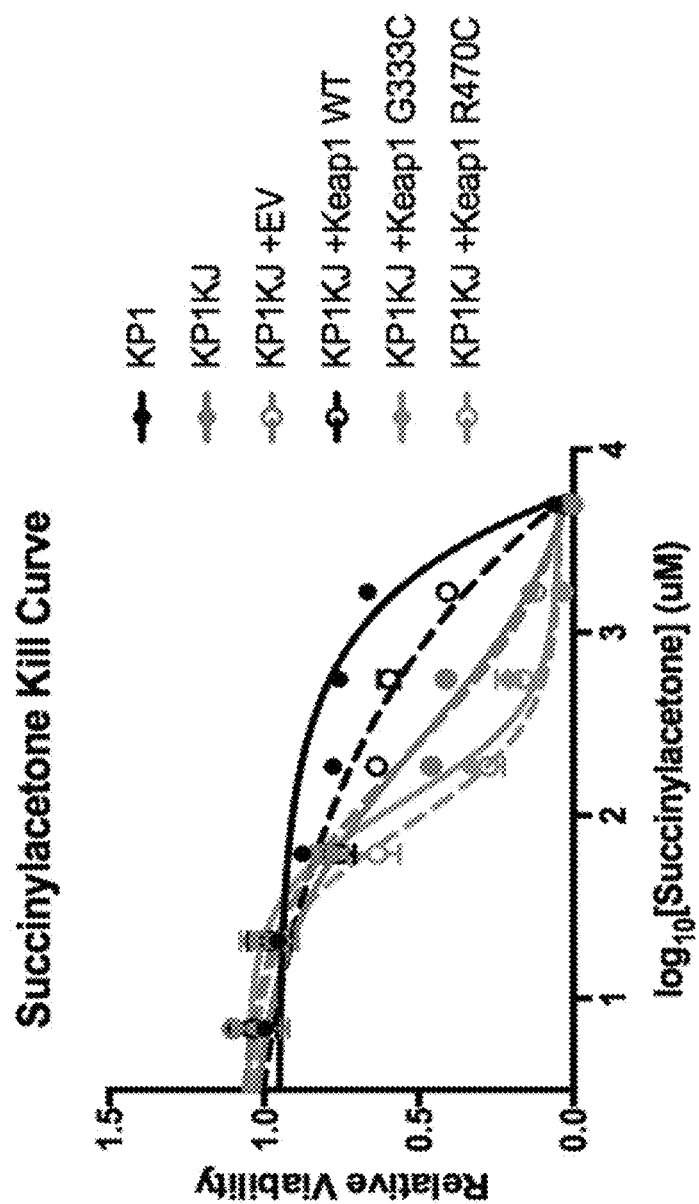

FIG. 35A and FIG. 35B depict the results of exemplary experiments demonstrating that dominant negative Keap1 alleles further sensitize Keap1 mutant cells to heme synthesis inhibition. FIG. 35A depicts a western blot validation of various Keap1 cDNA constructs including WT and multiple mutants found in LUAD. FIG. 35B depicts the relative viability of cell lines with different genetic status of Keap1 in response to different concentrations of succinylacetone, an inhibitor of Alas1.

Figure 36A:
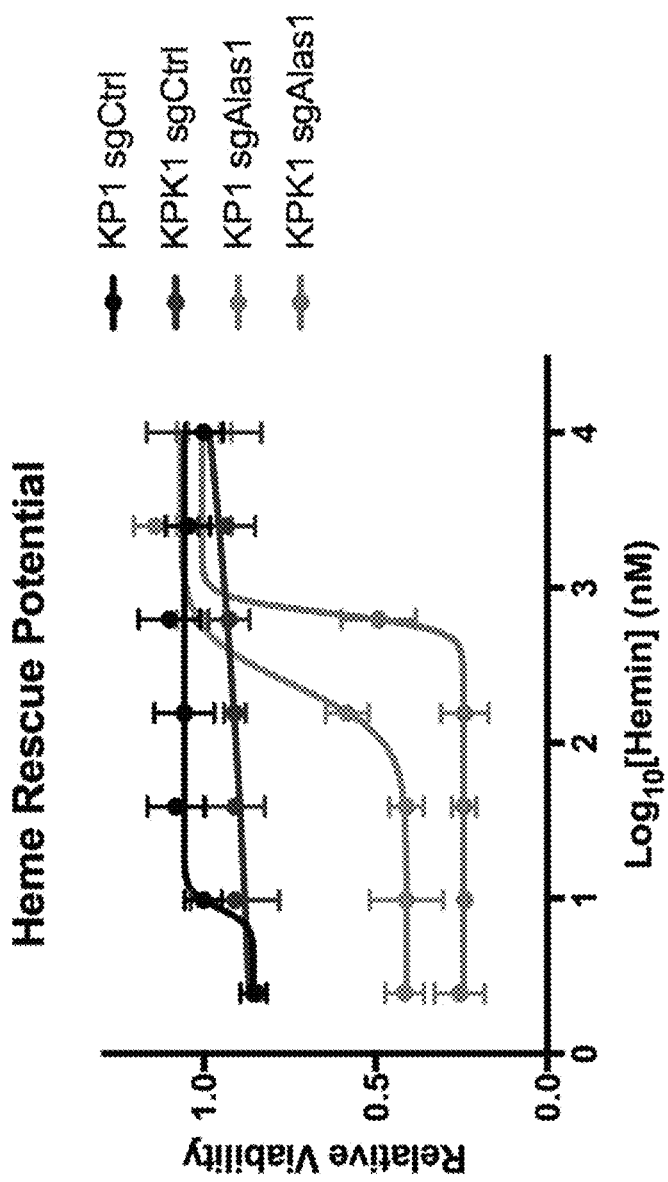
Figure 36B:
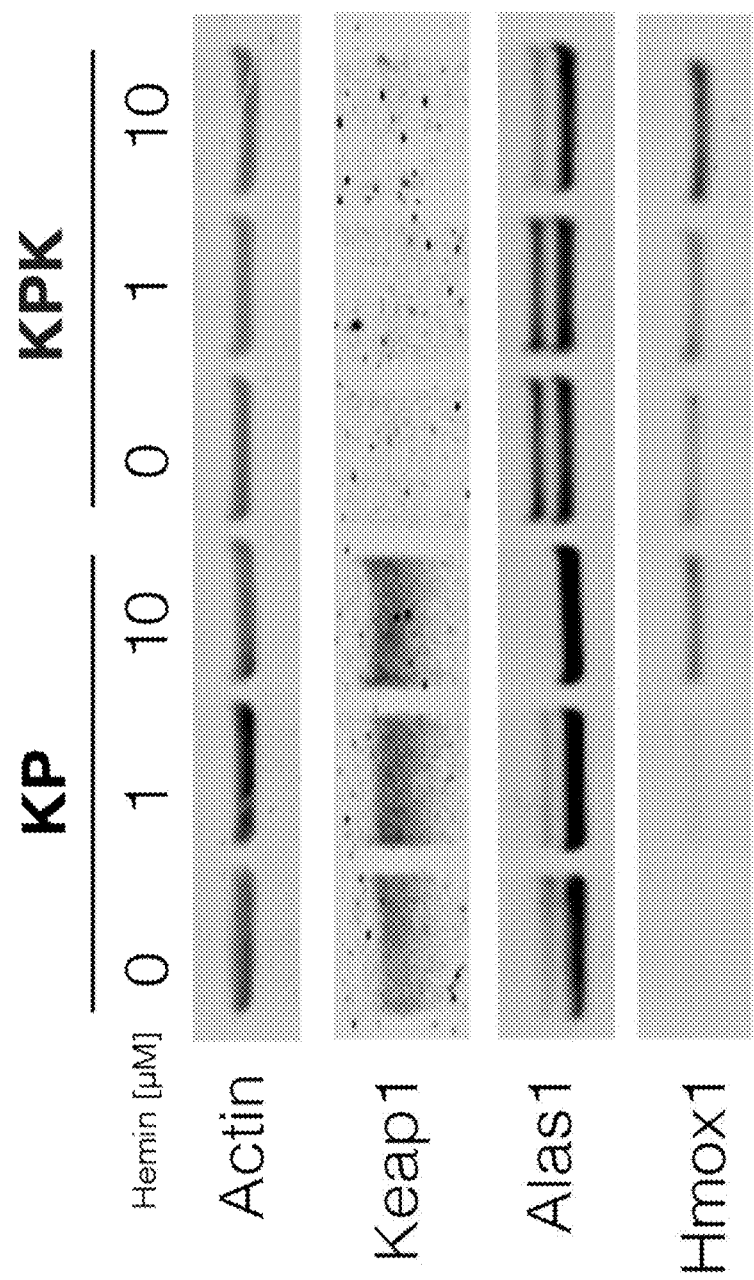

FIG. 36A and FIG. 36B depict the results of exemplary experiments demonstrating that Keap1-mutant cells require higher levels of exogenous heme to rescue growth. FIG. 36A depicts the cell viability of KP or KPK cells with guide RNAs against Alas1 or control in the presence of increasing amounts of Heme/Hemin. FIG. 36B depicts a western blot demonstrating that KPK cells have higher levels of Alas1 and Hmox1 and that increasing amounts of exogenous heme/hemin decrease Alas1 and increase Hmox1.

Figure 37A:
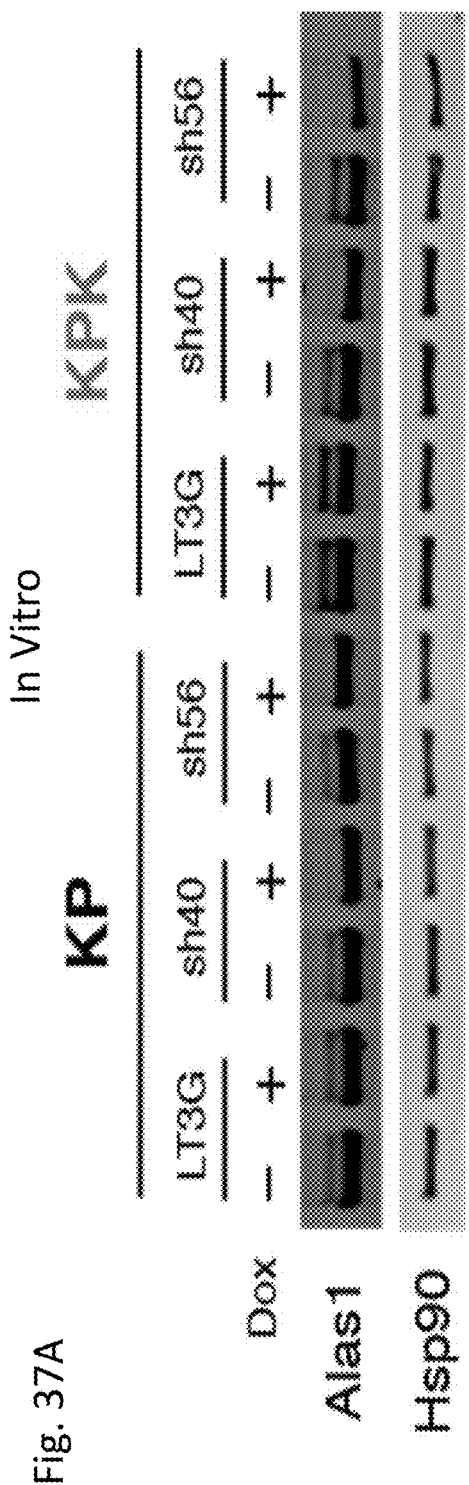
Figure 37B:
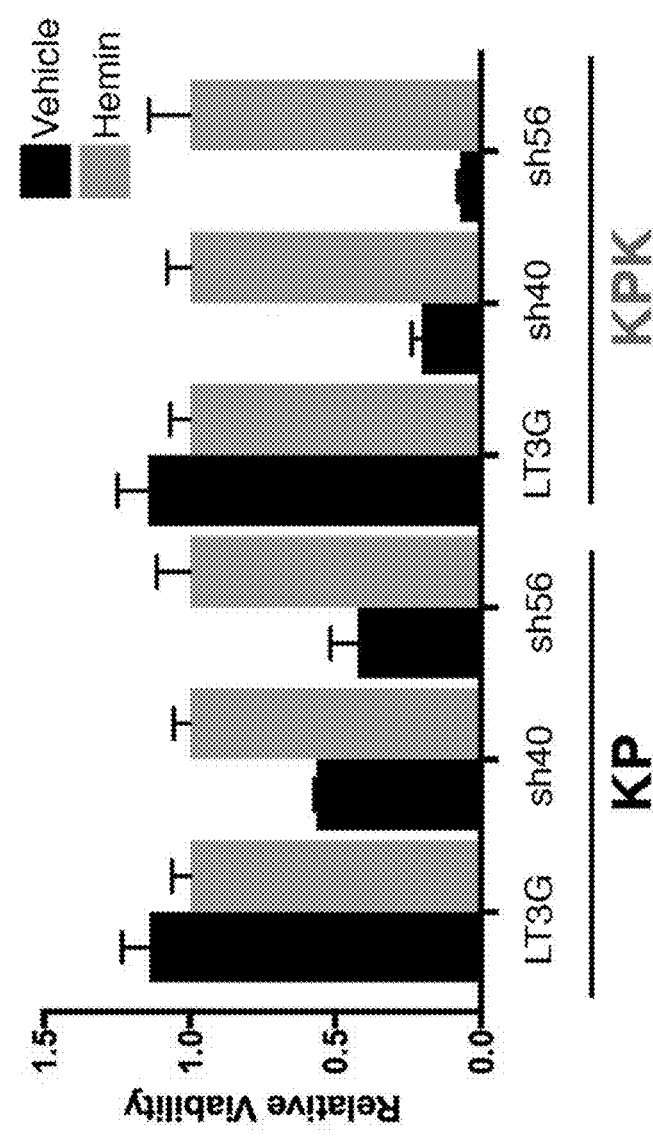

FIG. 37A and FIG. 37B depict the results of exemplary experiments demonstrating that Keap1-mutant cells show increased sensitivity to Alas1 knock-down/out. FIG. 37A depicts a western blot validation of control or Alas1 targeting shRNAs in KP/KPK cells. FIG. 37B depicts the relative viability of KP/KPK cells in response to doxycycline inducible shRNA knockdown of Alas1. Addition of heme/hemin completely rescues any growth defects in the absence of Alas1.

Figure 38:
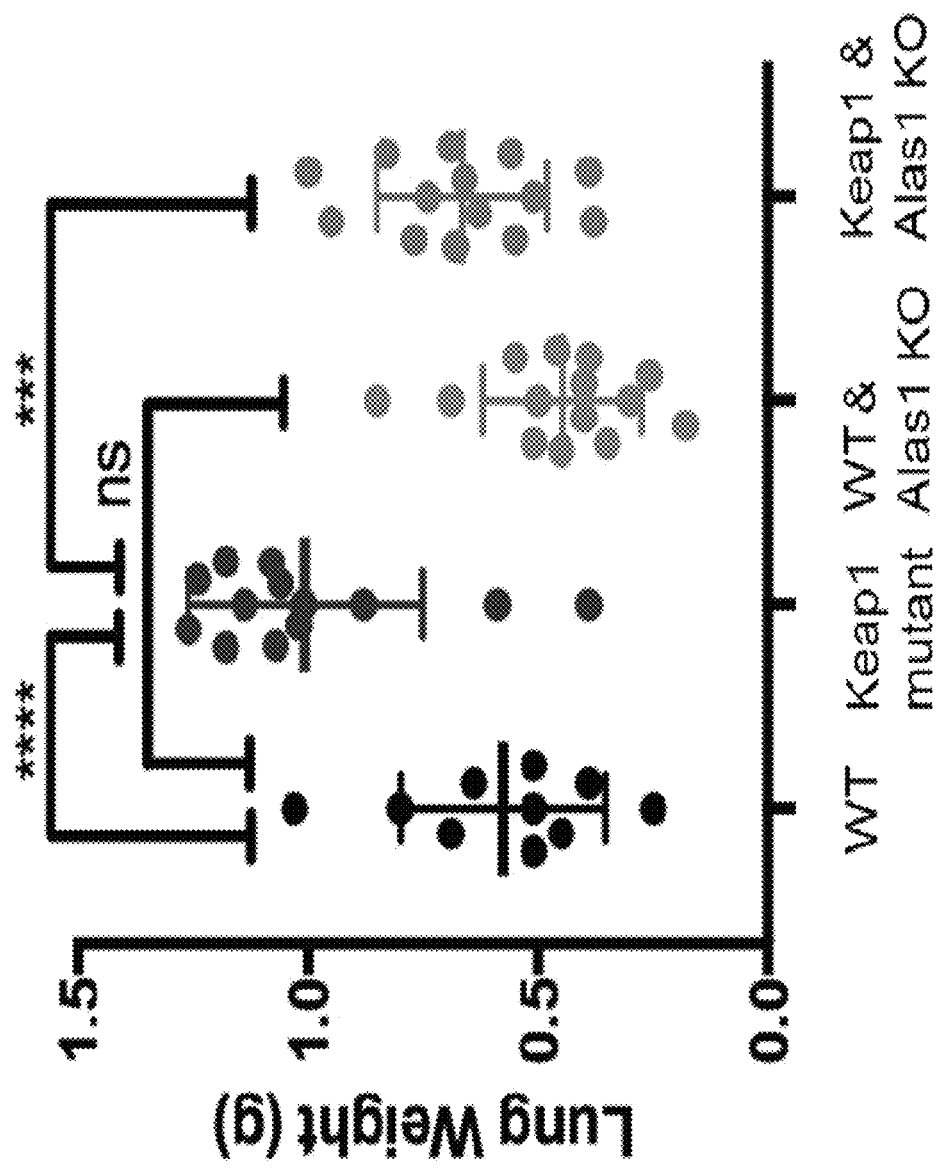

FIG. 38 depict the results of exemplary experiments demonstrating that Keap1-mutant cells show increased sensitivity to Alas1 knockout in vivo. Lung weights, a readout for tumor burden, from Kras-driven from WT or Keap1 mutant LUAD tumors where Alas1 is also deleted using CRISPR/Cas9-based methods. Alas1 loss suppresses tumors growth (synthetic lethal) only in Keap1 mutant tumors.

Figure 39A:
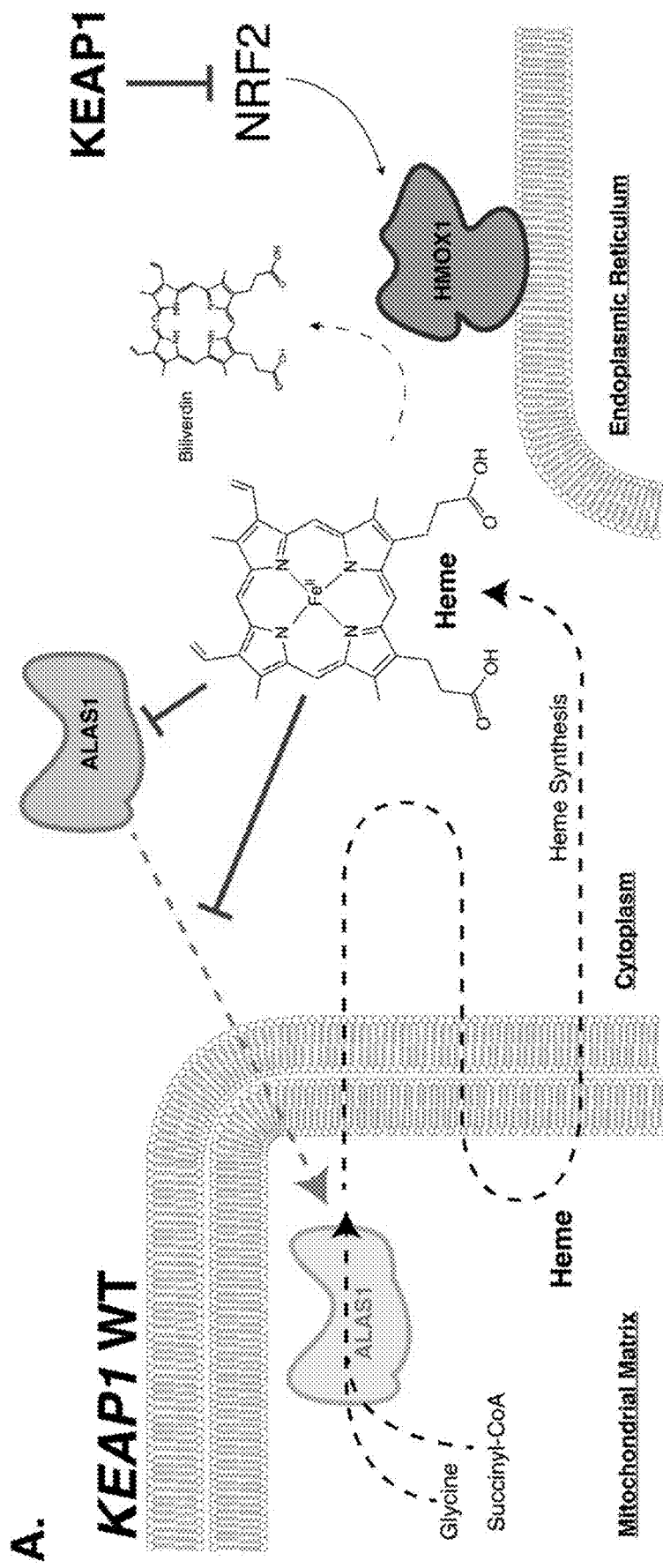

FIG. 39A depicts a diagram demonstrating that heme synthesis is regulated by product inhibition.

Figure 39B:
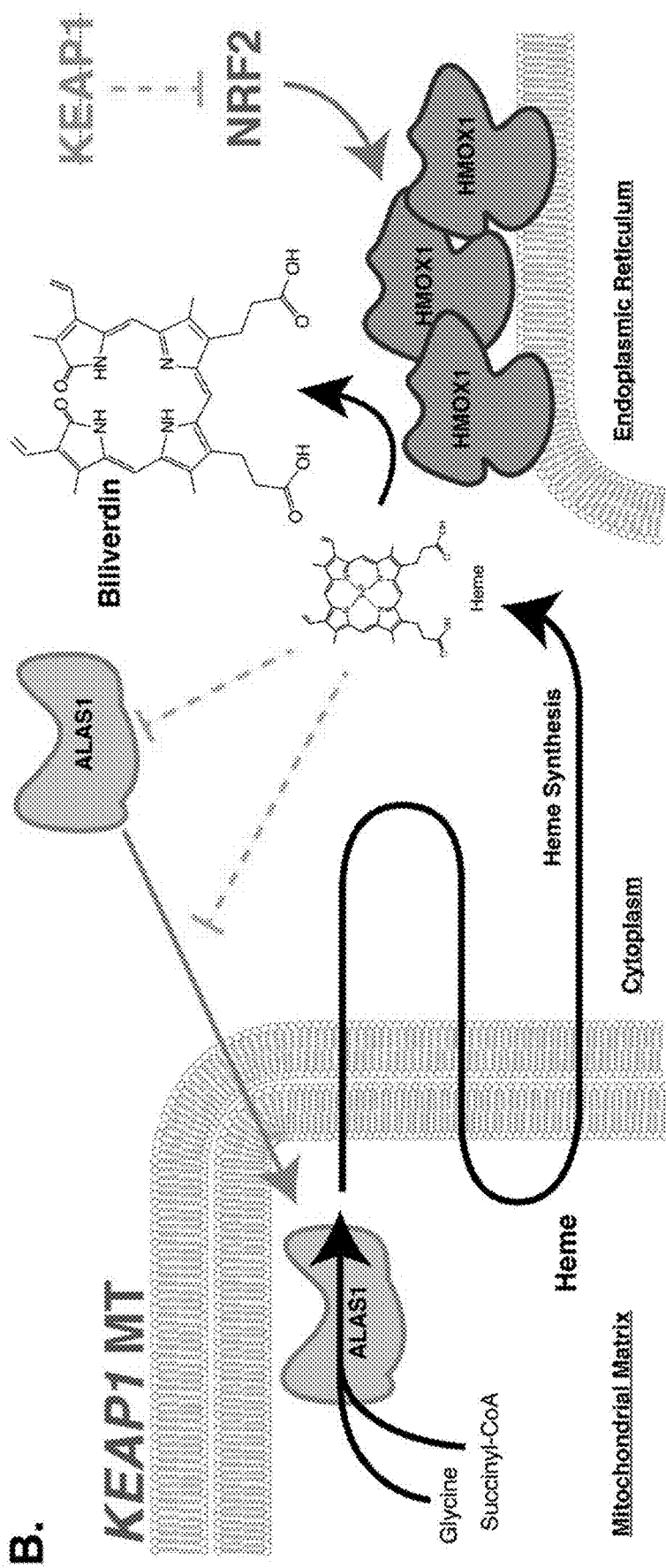

FIG. 39B depicts a diagram demonstrating that the Keap1/Nrf2 signaling axis influences heme metabolism.

DETAILED DESCRIPTION

The invention is based, in part, on the discovery that genetic, pharmacologic, and ROS-dependent activation of NRF2 axis results in a dependency on multiple nonessential amino acids (NEAAs). This dependency is mediated by the NRF2-dependent excretion of glutamate through the system $x_c^-$ antiporter which limits availability of intracellular glutamate for NEAA synthesis. Therefore, the invention relates, in part, to a novel metabolic strategy to target cancers characterized as having activation of the Nrf2 antioxidant response pathway by restricting exogenous sources of NEAAs. The invention relates, in part, methods for treating cancers through activation of the Nrf2 antioxidant response pathway in combination with restricting exogenous sources of NEAAs.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "analog" as used herein generally refers to compounds that are generally structurally similar to the compound of which they are an analog, or "parent" compound. Generally, analogs will retain some characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while at least one distinct biological activities of the parent are unaffected in the "analog."

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes, examination of cells, cytogenetics, and immunophenotyping of blood cells.

As used herein, "conjugated" refers to covalent attachment of one molecule to a second molecule.

The term "comparator" describes a material comprising none, or a normal, low, or high level of one of more of the marker (or biomarker) expression products of at least one the markers (or biomarkers) of the invention, such that the comparator may serve as a control or reference standard against which a sample can be compared.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of at least one polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

As used herein, the term "diagnosis" means detecting a disease or disorder or determining the stage or degree of a disease or disorder. Usually, a diagnosis of a disease or disorder is based on the evaluation of at least one factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

As used herein "endogenous" refers to any material from or produced inside an organism, cell, tissue or system.

As used herein "exogenous" refers to any material from or produced outside an organism, cell, tissue or system.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means. "Polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of at least one nucleotides, or fusion to other polynucleotide sequences.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "pharmaceutically acceptable carrier" means a pharmaceutically acceptable material, composition or carrier, such as a liquid or solid filler, diluent, excipient, solvent or encapsulating material, involved in carrying or transporting an agent to the subject such that it can perform its intended function. Agents can be carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the therapeutic agent, and are physiologically acceptable to the subject. Supplementary active compounds can also be incorporated into the compositions.

The terms "subject," "patient," "individual," and the like are used interchangeably herein, and refer to any animal, or cells thereof whether in vitro or in situ, amenable to the methods described herein. Thus, the individual may include, for example, dogs, cats, pigs, cows, sheep, goats, horses, rats, monkeys, and mice and humans. In some non-limiting embodiments, the patient, subject or individual is a human.

A "therapeutic" treatment is a treatment administered to a subject who exhibits a sign or symptom of a disease or disorder, for the purpose of diminishing or eliminating the sign or symptom of the disease or disorder.

The terms "treat," "treating," and "treatment," refer to therapeutic or preventative measures described herein. The methods of "treatment" employ administration to a subject, in need of such treatment, a composition of the present invention. For example, a subject afflicted with a disease or disorder, or a subject who ultimately may acquire such a disease or disorder, in order to prevent, cure, delay, reduce the severity of, or ameliorate at least one sign or symptom of the disease or disorder.

The terms "treat," "treating," and "treatment," refer to therapeutic or preventative measures described herein. The methods of "treatment" employ administration to a subject, in need of such treatment, a composition of the present invention, for example, a subject afflicted a disease or disorder or a subject who ultimately may acquire such a disease or disorder, in order to prevent, cure, delay, reduce the severity of, or ameliorate at least one symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on experiments demonstrating that a combination of increased levels of reactive oxygen species (ROS) and depletion of at least one non-essential amino acid (NEAA) can suppress tumor growth. The present invention is based, in part, on experiments demonstrating a synthetic lethality between Keap1/Nrf2 inhibition and inhibition of the pentose phosphate pathway (PPP). The invention is further based, in part, on experiments demonstrating that the Keap1/Nrf2 signaling axis influences heme metabolism.

Therefore, the invention, in part, provides methods for treating cancer comprising administering to the subject an agent for reducing at least one NEAA, inhibiting the PPP pathway, inhibiting the sorbitol pathway, inhibiting heme biosynthesis, or any combination thereof. The invention, in part, provides methods for treating cancer comprising identifying a tumor as having an increased level of ROS and administering to the subject an agent for reducing at least one NEAA, inhibiting the PPP pathway, inhibiting the sorbitol pathway or inhibiting heme biosynthesis, or any combination thereof. The invention, in part, provides methods for treating cancer comprising administering to the subject a treatment for increasing the level of ROS in combination with a treatment for reducing at least one NEAA.

Methods of Increasing ROS

In one embodiment, the invention provides a method of treating cancer comprising administering at least one agent that increases the level of ROS in the tumor. In one embodiment, at least one agent increases the level of ROS is selected from an inhibitor of Keap1; an inhibitor of glutathione (GSH); an activator of NRF2; an inhibitor of thioredoxin reductases; and an electrophile that reacts with Keap1 cysteines and leads to Nrf2 stabilization.

In various embodiments, the agent of the invention increases the quantity, number, amount or percentage of ROS or at least one oxidized product by at least 1%, at least 10%, at least 25%, at least 30%, at least 40%, at least 50%, at least 65%, at least 75%, at least 85%, at least 95%, at least 99% or by more than 99% relative to a negative control. The quantity or percentage of ROS or at least one oxidized product can be measured by any method known in the art. Exemplary methods for measuring ROS or oxidized products include, but are not limited to, chemiluminescence, nitroblue tetrazolium test (NBT), cytochrome c reduction, flow cytometry, electron spin resonance, and xylenol orange-based assay.

Activators of NRF2

In various embodiments, the present invention includes NRF2 activator compositions and methods of use thereof to increase ROS in a subject, a tissue, or an organ in need thereof. In various embodiments, the NRF2 activator compositions and methods of treatment of the invention increase the amount or stability of NRF2 polypeptide, the amount or stability of NRF2 mRNA, the amount of NRF2 enzymatic activity, the amount of NRF2 substrate binding activity, or a combination thereof.

One of skill in the art will realize that in addition to activating NRF2 directly, diminishing the amount or activity of a molecule that itself diminishes the amount or activity of NRF2 can serve to increase the amount or activity of NRF2. Thus, an NRF2 activator can include, but should not be construed as being limited to, a chemical compound, a protein, a peptidomemetic, an antibody, a ribozyme, and an antisense nucleic acid molecule. Further, one of skill in the art would, when equipped with this disclosure and the methods exemplified herein, appreciate that an NRF2 activator includes such activators as discovered in the future, as can be identified by well-known criteria in the art of pharmacology, such as the physiological results of activation of NRF2 as described in detail herein and/or as known in the art. Additionally, an NRF2 activator encompasses a chemically modified compound, and derivatives, as is well known to one of skill in the chemical arts.

It will be understood by one skilled in the art, based upon the disclosure provided herein, that an increase in the level of NRF2 encompasses the increase in NRF2 expression, including transcription, translation, or both. The skilled artisan will also appreciate, once armed with the teachings of the present invention, that an increase in the level of NRF2 includes an increase in NRF2 activity (e.g., enzymatic activity, substrate binding activity, etc.). Thus, increasing the level or activity of NRF2 includes, but is not limited to, increasing the amount of NRF2 polypeptide, and increasing transcription, translation, or both, of a nucleic acid encoding NRF2; and it also includes increasing any activity of an NRF2 polypeptide as well. The NRF2 activator compositions and methods of the invention can selectively activate NRF2, or can activate both NRF2 and another molecule.

The increased level or activity of NRF2 can be assessed using a wide variety of methods, including those disclosed herein, as well as methods well-known in the art or to be developed in the future. That is, the person of skill in the art would appreciate, based upon the disclosure provided herein, that increasing the level or activity of NRF2 can be readily assessed using methods that assess the level of a nucleic acid encoding NRF2 (e.g., mRNA), the level of NRF2 polypeptide, and/or the level of NRF2 activity in a biological sample obtained from a subject.

One of skill in the art would readily appreciate, based on the disclosure provided herein, that an NRF2 activator encompasses a chemical compound that increases the enzymatic activity of NRF2. Exemplary compounds that increase the enzymatic activity of NRF2 include, but are not limited to, electrophilic compounds that react with Keap1 cysteines such as isothiocyanate sulforaphane (1-isothiocyanato-4R-(methylsulfinyl)butane), HBB2 (bis(2-hydroxybenzylidene) acetone), TP-225 (2-cyano-3,12-dioxooleana-1,9(11)-dien-28-onitrile), TBE-31 ((±)-(4bS,8aR,10aS)-10a-ethynyl-4b,8,8-trimethyl-3,7-dioxo-3.4b,7,8,8a,9,10,10a-octahydrophenanthrene-2,6-dicarbonitrile), MCE-1 (3-ethynyl-3-methyl-6-oxocyclohexa-1,4-dienecarbonitrile) and MCE-5 (3,3,5,5-tetramethyl-6-oxocyclohex-1-enecarbonitrile).

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of NRF2.

Inhibitors of Keap1

One of skill in the art will realize that diminishing the amount or activity of a molecule that itself diminishes the amount or activity of NRF2 can serve to increase the amount or activity of NRF2. Therefore, in one embodiment, the invention relates to a method of administering an inhibitor of Keap1, which itself is a negative regulator of NRF2.

It will be understood by one skilled in the art, based upon the disclosure provided herein, that a decrease in the level of Keap1 encompasses the decrease in Keap1 expression, including transcription, translation, or both. The skilled artisan will also appreciate, once armed with the teachings of the present invention, that a decrease in the level of Keap1 includes a decrease in Keap1 activity (e.g., enzymatic activity, substrate binding activity, etc.). Thus, decreasing the level or activity of Keap1 includes, but is not limited to, decreasing transcription, translation, or both, of a nucleic acid encoding Keap1; and it also includes decreasing any activity of an Keap1 polypeptide as well. The Keap1 inhibitor compositions and methods of the invention can selectively inhibit Keap1, or can inhibit both Keap1 and another molecule.

The Keap1 inhibitor compositions and methods of the invention that decrease the level or activity (e.g., enzymatic activity, substrate binding activity, etc.) of Keap1 include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that an Keap1 inhibitor composition encompasses a chemical compound that decreases the level or activity of Keap1. Additionally, an Keap1 inhibitor composition encompasses a chemically modified compound, and derivatives, as is well known to one of skill in the chemical arts. In one embodiment, the inhibitor of Keap1 is KI-696 or an imidazole derivative of 2-cyano-3,12-dioxooleana-1,9(11)-dien-28-oic acid (CDDO-Im).

Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity Keap1. Contemplated in the present invention are antisense oligonucleotides that are synthesized and provided to the cell by way of methods well known to those of ordinary skill in the art. As an example, an antisense oligonucleotide can be synthesized to be between about 10 and about 100, and in some embodiments between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of Keap1 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

In one embodiment, the inhibitor of Keap1 may comprise one or more components of a CRISPR-Cas system. CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligo to hybridize to target and recruit the Cas/gRNA complex. In one embodiment, a guide RNA (gRNA) targeted to a gene encoding PTPN22, and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

The Keap1 inhibitor compositions of the invention include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to Keap1.

Further, one of skill in the art, when equipped with this disclosure and the methods exemplified herein, would appreciate that an Keap1 inhibitor composition includes such inhibitors as discovered in the future, as can be identified by well-known criteria in the art of pharmacology, such as the physiological results of inhibition of Keap1 as described in detail herein and/or as known in the art. Therefore, the present invention is not limited in any way to any particular Keap1 inhibitor composition as exemplified or disclosed herein; rather, the invention encompasses those inhibitor compositions that would be understood by the person of skill in the art to be useful as are known in the art and as are discovered in the future.

Inhibitors of Antioxidant Pathways

In one embodiment, an agent for increasing the level of ROS is an inhibitor of at least one molecule, peptide, protein or enzyme involved in an antioxidant pathway. In one embodiment, the antioxidant pathway is selected from the thioredoxin pathway and the glutathione (GSH) pathway.

The antioxidant pathway inhibitor compositions of the invention that increase the level of ROS include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof.

In one embodiment, the inhibitor of the invention inhibits GSH biosynthesis. For example, in one embodiment, the inhibitor of the invention inhibits an enzyme selected from the group consisting of glutamate cysteine ligase (GCL) and GSH synthetase (GSS). Exemplary GSH inhibitors include, but are not limited to, buthionine sulfoxime and 1-chloro-2,4-dinitrobenzene (DNCB).

In one embodiment, the inhibitor of the invention inhibits the thioredoxin pathway. For example, in one embodiment, the inhibitor of the invention inhibits thioredoxin or thioredoxin reductase. Thioredoxin pathway inhibitors include, but are not limited to, mitomycin C, auranofin (3,4,5-triacetyloxy-6-(acetyloxymethyl) oxane-2-thiolate; triethylphosphanium), aurothiomalate, aurothiosulfate, aurothioglucose, and DNCB.

Methods of Decreasing NEAA

In one embodiment, the invention provides a method of treating cancer comprising decreasing the level of at least of NEAA in the tumor. Exemplary NEAA that can be decreased in accordance with the methods of the invention include, but are not limited to glutamate, glutamine, proline, serine, alanine, glycine, arginine, lysine, asparagine, methionine, threonine, and isoleucine. Therefore, in one embodiment, the invention provides a method of treating cancer comprising administering at least one agent that decreases the level of at least one of glutamate, glutamine, proline, serine, alanine, glycine, arginine, lysine, asparagine, methionine, threonine, and isoleucine. In one embodiment, the invention provides a method of treating cancer comprising administering a dietary regimen that decreases the level of at least one of glutamate, glutamine, proline, serine, alanine, glycine, arginine, lysine, asparagine, methionine, threonine, and isoleucine.

The compositions that decrease the level of at least one NEAA of the invention include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof.

In various embodiments, the agent of the invention decreases the quantity, number, amount or percentage of at least one NEAA by at least 1%, at least 10%, at least 25%, at least 30%, at least 40%, at least 50%, at least 65%, at least 75%, at least 85%, at least 95%, at least 99% or by more than 99% relative to a negative control. The quantity or percentage of NEAA can be measured by any method known in the art.

Exemplary agents that can be administered to decreases the level of at least one NEAA include, but are not limited to, an asparaginase, a serine degrading enzyme, an inhibitor of phosphoserine aminotransferase, an inhibitor of an amino acid transporter, an inhibitor of glutaminase (GLS), an inhibitor of glutamate dehydrogenase (GLUD), an aminotransferase inhibitor, and a competitive inhibitors of glutamine.

In one embodiment, the asparaginase is a native asparaginase derived from *Escherichia coli;* a pegylated form of the native *E. coli*-asparaginase (polyethylene glycol-asparaginase); or an asparaginase enzyme isolated from *Erwinia chrysanthemi*.

In one embodiment, the serine degrading enzyme is L-serine ammonia lyase (SDH).

In one embodiment, the amino acid transporter is a transporter for glutamate, glutamine, proline, serine, alanine, glycine, arginine, lysine, asparagine, methionine, threonine, or isoleucine. Exemplary amino acid transporters that can be inhibited according to the methods of the invention include, but are not limited to, EAAT1, EAAT2, EAAT3, SLC1A5, SLC1A3, SLC6A7, ASCT1, GlyT1, GlyT2, SLC7A2, SLC6A14, MetNIQ, and an ABC transporter. Exemplary inhibitors of amino acid transporters include, but are not limited to, 2-amino-4-bis(aryloxybenzyl)aminobutanoic acids (AABA), benzylserine, gamma-L-Glutamyl-p-Nitroanilide (GPNA).

Exemplary agents for decreasing the level of at least one NEAA that can be administered according to the methods of the invention include, but are not limited to, GPNA, γ-FBP, benzylserine, BPTES, CB-839, compound 968, EGCG, R162, GCN2iA, 6-diazo-5-oxo-1-norleucine (DON) and AOA.

Inhibitors of the PPP Pathway

In one embodiment, the invention relates to an agent for inhibition of at least one molecule, peptide, protein or enzyme involved in the PPP pathway, which is responsible for the generation of NADPH. Exemplary enzymes involved in the PPP pathway that can be inhibited include, but are not limited to, glucose-6-phosphate dehydrogenase (G6PD or G6PDH), 6-phosphogluconolactonase, 6-phosphogluconate dehydrogenase, fructose-bisphosphate aldolase B, ribose-5-phosphate isomerase, Ribulose 5-Phosphate 3-Epimerase, transaldolase, solute carrier family 16 member 1 (SLC16A1 or MCT1) and lactate dehydrogenase A (LDHA).

The PPP inhibitor compositions of the invention include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, sgRNA etc.), or combinations thereof, as described in detail elsewhere herein.

Exemplary agents for inhibiting the PPP that can be administered according to the methods of the invention include, but are not limited to, dehydropiandrosterone (DHEA), N-(4-Hydroxynaphthalen-1-yl)-2,5-dimethylbenzenesulfonamide (CB-83), 6-Aminonicotinamide, SR13800, AZD 3965, R-GNE-140, NCI-006 and G6PDi-1 (Ghergurovich et al., 2020, Nat Chem Biol, 16(7):731-739).

Inhibitors of the Sorbitol Pathway

In one embodiment, the invention relates to a method of inhibiting the sorbitol pathway to increase the sorbitol pool. Exemplary enzymes involved in the sorbitol pathway that can be inhibited include, but are not limited to, sorbitol dehydrogenase (SORD), ketohexokinase, Triokinase and FMN Cyclase (TKFC), aldo-keto reductase family 1, member B1 (AKR1b1), aldo-keto reductase family 1, member B3 (AKR1b3), aldo-keto reductase family 1, member B7 (AKR1b7), aldo-keto reductase family 1, member B8 (AKR1b8), aldo-keto reductase family 1, member B10 (AKR1b10), sterol regulatory element binding protein-1c (SREBP-1c), Carbohydrate-responsive element-binding protein (ChREBP), fructose transporter solute carrier family 2 member 5 (SLC2A5 or GLUT5), solute carrier family 16 member 1 (SLC16A1 or MCT1) and lactate dehydrogenase A (LDHA).

The sorbitol pathway inhibitor compositions of the invention include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, sgRNA etc.), or combinations thereof, as described in detail elsewhere herein.

Exemplary agents for inhibiting the sorbitol pathway that can be administered according to the methods of the invention include, but are not limited to, aldose reductase inhibitors, Epalrestat, KHK-IN-1 hydrochlorid, PF-06835919, 2,5-Anhydro-D-mannitol, SR13800, AZD 3965, R-GNE-140, and NCI-006.

Inhibitors of the Heme Biosynthesis Pathway

In one embodiment, the invention relates to a method of inhibiting heme biosynthesis or the heme biosynthesis pathway. Exemplary enzymes involved in the heme biosynthesis pathway that can be inhibited include, but are not limited to, 5-aminolevulinic acid synthase-1 (ALAS1), delta-aminolevulinic acid dehydratase (ALAD), hydroxymethylbilane synthase (HMBS), uroporphyrinogen III synthase (UROS), uroporphyrinogen decarboxylase (UROD), coproporphyrinogen oxidase (CPOX), protoporphyrinogen oxidase (PPOX), transmembrane protein 14C (TMEM14C), FLVCR heme transporter 1 (FLVCR1), solute carrier family 48 member 1 (SLC48A1) and ferrochelatase (FECH).

The heme biosynthesis inhibitor compositions of the invention include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, sgRNA etc.), or combinations thereof, as described in detail elsewhere herein.

Exemplary agents for inhibiting the heme pathway that can be administered according to the methods of the invention include, but are not limited to, heme, 4,6-Dioxoheptanoic acid (Succinylacetone), 6-Methyl-PBG, PI-16, SH-11052 and glucose.

Proteins and Peptides

In one embodiment, at least one of an agent for increasing the level of ROS, inhibiting the sorbitol pathway, inhibiting heme biosynthesis, inhibiting PPP, inhibiting Keap1 or decreasing the level of at least one NEAA, or any combination thereof, of the invention comprises a protein or peptide. The peptide of the present invention may be made using chemical methods. For example, peptides can be synthesized by solid phase techniques cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

In one embodiment, the peptide is made by recombinant means or by cleavage from a longer polypeptide. The composition of a peptide may be confirmed by amino acid analysis or sequencing.

The peptides can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103, 489) to a standard translation reaction. A peptide or protein of the invention may be modified, e.g., phosphorylated, using conventional methods.

The peptides may include unnatural amino acids formed by post-translational modification or by introducing unnatural amino acids during translation. A variety of approaches are available for introducing unnatural amino acids during protein translation.

In one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, of the invention comprises a cyclic peptide. Cyclization of peptide may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulfide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The peptide may be synthesized by conventional techniques. For example, the peptides or chimeric proteins may be synthesized by chemical synthesis using solid phase peptide synthesis or solution phase synthesis methods. By way of example, a peptide may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain a peptide fused to the selected protein or marker protein as described herein. Examples of proteins which may be used to prepare fusion proteins include immunoglobulins, glutathione-S-transferase (GST), hemagglutinin (HA), and truncated myc.

Peptides may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. Libraries may also be constructed by concurrent synthesis of overlapping peptides.

Peptides and proteins may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In one embodiment, the composition comprising at least one agent for increasing the level of ROS, inhibiting the sorbitol pathway, inhibiting heme biosynthesis, inhibiting PPP, inhibiting Keap1 or decreasing the level of at least one NEAA, or any combination thereof, comprises an antibody, or antibody fragment, that specifically binds to a target. In some embodiments, the antibody can inhibit the target to provide a beneficial effect.

Antibody Therapeutic Agents

In one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, comprises an antibody, or antibody fragment, that specifically binds to a target. In some embodiments, the antibody can inhibit the target to provide a beneficial effect.

In various embodiments, the antibody is a monoclonal antibody, polyclonal antibody, immunologically active fragments of an antibody (e.g., a Fab or (Fab)2 fragment), antibody heavy chain, antibody light chain, humanized antibody, genetically engineered single chain FV molecule, or a chimeric antibody. In some embodiments, the chimeric antibody contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using an intact polypeptide, or a fragment of the polypeptide containing an immunizing antigen of interest. The polypeptide or fragment used to immunize an animal may be obtained from the translation of RNA, or can be synthesized chemically, and can be conjugated to a carrier protein, if desired. Suitable carriers that may be chemically coupled to polypeptides and fragment thereof include bovine serum albumin, thyroglobulin, and keyhole limpet hemocyanin. The coupled polypeptide can then be used to immunize an animal (e.g., a mouse, a rat, or a rabbit).

Small Molecule Therapeutic Agents

In various embodiments, the agent is a small molecule chemical compound. When the therapeutic agent is a small molecule, the small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule therapeutic agent comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determine the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the agents depicted here, as well as the non-salt and non-solvate form of the agents, as is well understood by the skilled artisan. In some embodiments, the salts of the agents of the invention are pharmaceutically acceptable salts.

Where tautomeric forms may be present for any of the agents described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diastereomeric forms of the agents described. The recitation of the structure or name herein is intended to embrace all possible stereoisomers of agents depicted. All forms of the agents are also embraced by the invention, such as crystalline or non-crystalline forms of the agents. Compositions comprising an agent of the invention are also intended, such as a composition of substantially pure agent, including a specific stereochemical form thereof, or a composition comprising mixtures of agents of the invention in any ratio, including two or more stereochemical forms, such as in a racemic or non-racemic mixture.

In one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, of the invention comprises an analog or derivative of a therapeutic agent described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule therapeutic agents described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by at least one chemical reactions. As such, an analog can be a structure having a structure similar to that of the small molecule therapeutic agents described herein or can be based on a scaffold of a small molecule therapeutic agent described herein, but differing from it in respect to certain components or structural makeup, which may have a similar or opposite action metabolically. An analog or derivative of any of a small molecule agent in accordance with the present invention can be used to treat a disease or disorder.

In one embodiment, the small molecule therapeutic agents described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having at least one hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Therapeutic Agents

In some embodiments, the agent is an isolated nucleic acid. In various embodiments, the isolated nucleic acid molecule is a DNA molecule or an RNA molecule. In various embodiments, the isolated nucleic acid molecule is a cDNA, mRNA, miRNA, siRNA, antagomir, antisense molecule, or CRISPR guide RNA molecule. In one embodiment, the isolated nucleic acid molecule encodes a therapeutic peptide. In some embodiments, the therapeutic agent is an siRNA, miRNA, sgRNA or antisense molecule, which inhibits a targeted nucleic acid. In one embodiment, the nucleic acid comprises a promoter/regulatory sequence such that the nucleic acid is capable of directing expression of the nucleic acid. Thus, in one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, of the invention comprises an expression vector, and the invention comprises a method for the introduction of exogenous DNA into cells with concomitant expression of the exogenous DNA in the cells.

In one embodiment of the invention, a targeted gene or protein, can be inhibited by way of inactivating and/or sequestering the targeted gene or protein. As such, inhibiting the activity of the targeted gene or protein can be accomplished by using an antisense nucleic acid molecule or a nucleic acid molecule encoding a transdominant negative mutant.

In one embodiment, siRNA is used to decrease the level of a targeted protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. In one embodiment, an siRNA comprises a chemical modification that aids in intravenous systemic delivery. Optimizing siRNAs involves consideration of overall G/C content, C/T content at the termini, Tm and the nucleotide content of the 3' overhang. Therefore, the present invention also includes methods of decreasing levels of expression products (i.e., mRNA and protein) of a target gene using RNAi technology.

In one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, of the invention comprises a vector comprising an siRNA or antisense polynucleotide. In one embodiment, the siRNA or antisense polynucleotide is capable of inhibiting the expression of a target polypeptide. The incorporation of a desired polynucleotide into a vector and the choice of vectors is well-known in the art.

In certain embodiments, the expression vectors described herein encode a short hairpin RNA (shRNA) therapeutic agent. shRNA molecules are well known in the art and are directed against the mRNA of a target, thereby decreasing levels of the expression products (i.e., mRNA and protein) of the target gene of interest. In certain embodiments, the encoded shRNA is expressed by a cell, and is then processed into siRNA. For example, in certain instances, the cell possesses native enzymes (e.g., dicer) that cleaves the shRNA to form siRNA.

In order to assess the expression of the siRNA, shRNA, or antisense polynucleotide, the expression vector to be introduced into a cell can also contain either a selectable marker gene or a reporter gene or both to facilitate identification of expressing cells from the population of cells contacted with at least one agent for increasing the level of ROS, inhibiting the sorbitol pathway, inhibiting heme biosynthesis, inhibiting PPP, inhibiting Keap1 or decreasing the level of at least one NEAA, or any combination thereof. In one embodiment, the selectable marker may be carried on a separate piece of DNA. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in one embodiment, at least one agent for increasing the level of ROS, inhibiting the sorbitol pathway, inhibiting heme biosynthesis, inhibiting PPP, inhibiting Keap1 or decreasing the level of at least one NEAA, or any combination thereof, may be in the form of a vector, comprising the nucleotide sequence or the construct to be delivered. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

By way of illustration, the vector in which the nucleic acid sequence is introduced can be a plasmid, which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art. In a particular embodiment, the vector is a vector useful for transforming animal cells.

In one embodiment, the recombinant expression vectors may also contain nucleic acid molecules, which encode a peptide or peptidomimetic.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, and other techniques known in the art. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene, which facilitates the selection of host cells. Suitable selectable marker genes are genes encoding proteins such as G418 and hygromycin, which confer resistance to certain drugs, β-galactosidase, chloramphenicol acetyltransferase, firefly luciferase, or an immunoglobulin or portion thereof such as the Fc portion of an immunoglobulin, such as IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like.

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

In one embodiment of the invention, an antisense nucleic acid sequence, which is expressed by a plasmid vector is used as a therapeutic agent to inhibit the expression of a target protein. The antisense expressing vector is used to transfect a mammalian cell or the mammal itself, thereby causing reduced endogenous expression of the target protein.

Antisense molecules and their use for inhibiting gene expression are well known in the art. Antisense nucleic acids are DNA or RNA molecules that are complementary to at least a portion of a specific mRNA molecule. In the cell, antisense nucleic acids hybridize to the corresponding mRNA, forming a double-stranded molecule thereby inhibiting the translation of genes.

The use of antisense methods to inhibit the translation of genes is known in the art. Such antisense molecules may be provided to the cell via genetic expression using DNA encoding the antisense molecule.

Alternatively, antisense molecules of the invention may be made synthetically and then provided to the cell. In one embodiment, antisense oligomers of between about 10 to about 30 nucleotides are used since they are easily synthesized and introduced into a target cell. Synthetic antisense molecules contemplated by the invention include oligonucleotide derivatives known in the art which have improved biological activity compared to unmodified oligonucleotides.

In one embodiment of the invention, a ribozyme is used as a therapeutic agent to inhibit expression of a target protein. Ribozymes useful for inhibiting the expression of a target molecule may be designed by incorporating target sequences into the basic ribozyme structure, which are complementary, for example, to the mRNA sequence encoding the target molecule. Ribozymes targeting the target molecule, may be synthesized using commercially available reagents or they may be genetically expressed from DNA encoding them.

In one embodiment, the therapeutic agent may comprise at least one component of a CRISPR-Cas system, where a guide RNA (gRNA) targeted to a gene encoding a target molecule, and a CRISPR-associated (Cas) peptide form a complex to induce mutations within the targeted gene. In one embodiment, the therapeutic agent comprises a gRNA or a nucleic acid molecule encoding a gRNA. In one embodiment, the therapeutic agent comprises a Cas peptide or a nucleic acid molecule encoding a Cas peptide.

Pharmaceutical Compositions

The present invention provides pharmaceutical compositions comprising at least one agent for use in the methods of the invention. The relative amounts of the agent(s), any pharmaceutically acceptable carrier, and any additional ingredients in a pharmaceutical composition of the invention will vary, depending upon the identity, size, and condition of the subject treated and further depending upon the route by which the composition is to be administered.

The formulations of the pharmaceutical compositions described herein may be prepared by any method known or hereafter developed in the art of pharmacology. In general, such preparatory methods include the step of bringing the active ingredient into association with a carrier or at least one other accessory ingredients. Said compositions may comprise additional medicinal agents, pharmaceutical agents, carriers, buffers, adjuvants, dispersing agents, diluents, and the like depending on the intended use and application.

Examples of suitable pharmaceutical carriers, excipients and/or diluents are well known in the art and include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, e.g., serum albumin or immunoglobulin, in some embodiments of human origin.

At least one agent for increasing the level of ROS, inhibiting the sorbitol pathway, inhibiting heme biosynthesis, inhibiting PPP, inhibiting Keap1 or decreasing the level of at least one NEAA, or any combination thereof, may be administered alone, or in combination with other drugs and/or agents as pharmaceutical compositions. The composition may contain at least one added materials such as carriers and/or excipients. As used herein, "carriers" and "excipients" generally refer to substantially inert, non-toxic materials that do not deleteriously interact with other components of the composition. These materials may be used to increase the amount of solids in particulate pharmaceutical compositions, such as to form a powder of drug particles. Examples of suitable carriers include water, silicone, gelatin, waxes, and the like.

Examples of normally employed "excipients," include pharmaceutical grades of mannitol, sorbitol, inositol, dextrose, sucrose, lactose, trehalose, dextran, starch, cellulose, sodium or calcium phosphates, calcium sulfate, citric acid, tartaric acid, glycine, high molecular weight polyethylene glycols (PEG), and the like and combinations thereof. In one embodiment, the excipient may also include a charged lipid and/or detergent in the pharmaceutical compositions. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, for example, TWEEN surfactants (Atlas Chemical Industries, Wilmington, Del.), polyoxyethylene ethers, for example, Brij®, pharmaceutically acceptable fatty acid esters, for example, lauryl sulfate and salts thereof (SDS), and the like. Such materials may be used as stabilizers and/or anti-oxidants. Additionally, they may be used to reduce local irritation at the site of administration.

In at least one embodiment, the composition is formulated in a lyophilized form. In certain embodiments, the lyophilized formulation of the composition allows for maintaining structure and achieving remarkably superior long-term stability conditions which might occur during storage or transportation of the composition.

Methods of Treatment

In one embodiment, the method of the invention includes identifying a subject as having a tumor that has an increased level of ROS, and administering to the subject a composition or treatment regimen for decreasing the level of at least one NEAA, inhibiting the PPP pathway, inhibiting the sorbitol pathway or inhibiting the heme biosynthesis pathway, or any combination thereof.

In on embodiment, the subject is identified as having at least one of a decreased level of Keap1 activity, an inactivating mutation of Keap1, an increased level of NRF2 activity, an increased level of a marker of NRf2 activation, and a mutation of a gene, wherein the mutation is associated with an increased level of NRF2 activity, in the tumor.

In one embodiment, the invention relates to methods of administering a composition comprising an agent for decreasing the level of at least one NEAA, inhibiting the PPP pathway, inhibiting the sorbitol pathway or inhibiting the heme biosynthesis pathway, or any combination thereof, to a subject identified as having a tumor having an increased level of ROS. In one embodiment, the invention relates to methods of administering a dietary regimen for decreasing the level of at least one NEAA to a subject identified as having a tumor having an increased level of ROS.

In one embodiment, the method of the invention includes altering one or more metabolic pathways in a subject. In one embodiment, the method includes administering one or more agent for modulation of the level of ROS, Keap1 activity, the level of at least one NEAA, the PPP pathway, the sorbitol pathway or the heme biosynthesis pathway, or any combination thereof. In one embodiment, the method includes altering a combination of metabolic pathways in a subject. In one embodiment, the method includes administering a combination of agents, wherein the combination of agents increases the level of ROS, inhibits Keap1, decreases the level of at least one NEAA, inhibits the PPP pathway, inhibits the sorbitol pathway or inhibits the heme biosynthesis pathway, or any combination thereof.

In one embodiment, the invention relates to methods of altering a combination of a level of reactive oxygen species (ROS) and a level of at least one NEAA in a subject in need thereof. In one embodiment, the invention is a method of increasing the level of ROS and decreasing the level of at least one NEAA in a subject in need thereof.

In one embodiment, the invention relates to methods of altering a combination of a level of reactive oxygen species (ROS) and the PPP in a subject in need thereof. In one embodiment, the invention is a method of increasing the level of ROS and inhibiting the PPP a subject in need thereof.

In one embodiment, the invention relates to methods of altering a combination of Keap1 and the PPP in a subject in need thereof. In one embodiment, the invention is a method of inhibiting Keap1 and inhibiting the PPP in a subject in need thereof.

In one embodiment, the invention relates to methods of altering a combination of a level of reactive oxygen species (ROS) and heme biosynthesis in a subject in need thereof. In one embodiment, the invention is a method of increasing the level of ROS and decreasing the level of heme biosynthesis in a subject in need thereof.

In one embodiment, the invention relates to methods of altering a combination of a level of reactive oxygen species (ROS) and sorbitol in a subject in need thereof. In one embodiment, the invention is a method of increasing the level of ROS and inhibiting the sorbitol pathway in a subject in need thereof.

In one embodiment, the invention relates to methods of altering a combination of Keap1 and the sorbitol pathway in a subject in need thereof. In one embodiment, the invention is a method of inhibiting Keap1 and inhibiting the sorbitol pathway in a subject in need thereof.

By way of an example, in one embodiment, the invention relates to methods of administering a first composition comprising an agent for decreasing the level of at least one NEAA in combination with a second agent for increasing the level of ROS. In one embodiment, the invention relates to methods of administering a dietary regimen for decreasing the level of at least one NEAA to a subject in combination with an agent for increasing the level of ROS.

In one embodiment, one or more agent of the invention is administered to a subject having cancer. Thus in one embodiment, the invention provides methods of modulating at least one of the level of ROS, Keap1 activity, the level of at least one NEAA, the PPP pathway, the sorbitol pathway or the heme biosynthesis pathway, or any combination thereof in a subject having cancer. In one embodiment, the method includes altering a combination of metabolic pathways in a subject having cancer. In one embodiment, the method includes administering a combination of agents, wherein the combination of agents increases the level of ROS, inhibits Keap1, decreases the level of at least one NEAA, inhibits the PPP pathway, inhibits the sorbitol pathway or inhibits the heme biosynthesis pathway, or any combination thereof in a subject having cancer.

The present invention also provides a method of treating or preventing a disease or disorder in a subject. In one embodiment, the disease or disorder is cancer or a cancer-associated disease or disorder. The following are non-limiting examples of cancers that can be treated by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilms tumor.

In various embodiments, at least one agent for increasing ROS, decreasing the level of at least one NEAA, inhibiting the PPP pathway, inhibiting the sorbitol pathway or inhibiting the heme biosynthesis pathway, or any combination thereof, is administered to a subject in need in a wide variety of ways. In various embodiments, at least one agent for increasing ROS, decreasing the level of at least one NEAA, inhibiting the PPP pathway, inhibiting the sorbitol pathway or inhibiting the heme biosynthesis pathway, or any combination thereof, is administered orally, intraoperatively, intratumorally, intravenously, intravascularly, intramuscularly, subcutaneously, intracerebrally, intraperitoneally, by soft tissue injection, by surgical placement, by arthroscopic placement, and by percutaneous insertion, e.g., direct injection, cannulation or catheterization. Any administration may be a single administration of a composition of invention or multiple administrations. Administrations may be to single site or to more than one site in the subject being treated. Multiple administrations may occur essentially at the same time or separated in time.

In certain embodiments, the composition of the invention is administered during surgical resection or debulking of a tumor or diseased tissue. For example, in subjects undergoing surgical treatment of diseased tissue or tumor, the composition may be administered to the site in order to further treat the tumor.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous (i.v.) injection, or intraperitoneally.

The composition comprising at least one agent as described herein can be incorporated into any formulation known in the art. For example, at least one agent for increasing ROS, at least one agent for decreasing at least one NEAA, or a combination thereof may be incorporated into formulations suitable for oral, parenteral, intravenous, subcutaneous, percutaneous, topical, buccal, or another route of administration. Suitable compositions include, but are not limited to, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

In the method of treatment, the administration of the composition of the invention may be for either "prophylactic" or "therapeutic" purpose. When provided prophylactically, the composition of the present invention is provided in advance of any sign or symptom, although in particular embodiments the invention is provided following the onset of at least one sign or symptom to prevent further signs or symptoms from developing or to prevent present signs or symptoms from becoming more severe. The prophylactic administration of the composition serves to prevent or ameliorate subsequent signs or symptoms. When provided therapeutically, the pharmaceutical composition is provided at or after the onset of at least one sign or symptom. Thus, the present invention may be provided either prior to the anticipated exposure to a disease-causing agent or disease state or after the initiation of the disease or disorder.

Dietary Restriction

In various embodiments, the invention includes administering a restrictive diet regimen to (i) a subject identified as having a tumor with an increased levels of ROS or (ii) in combination with an agent for increasing ROS, inhibiting the PPP pathway, inhibiting the sorbitol pathway or inhibiting the heme biosynthesis pathway, or any combination thereof. In one embodiment, the dietary regimen may comprise identifying a subset of food products that have low levels of at least one NEAA and including the identified food products in a dietary program. In one embodiment, the food products included in the dietary program are those identified as having less than 1%, less than 0.5% or less than 0.01% of a NEAA. In one embodiment, the invention relates to the use of a dietary product comprising a plurality of amino acids, comprising all essential amino acids and substantially lacking at least one NEAA. At least one of the non-essential amino acids may be selected from the group consisting of glycine, serine, cysteine, tyrosine and arginine. In one embodiment, the dietary product lacks at least 2, at least 3 or more than 3 NEAA. Exemplary combinations of NEAA that can be lacking in the dietary product include, but are not limited to, serine and glycine; cysteine and glycine; glycine, serine and cysteine; glycine, serine and arginine; and glycine, serine and tyrosine. In one embodiment, the dietary product may further comprise at least one macronutrient and/or at least one micronutrient. The dietary product of the invention can be formulated to at least provide a recommended daily intake of essential amino acids based on the average daily total protein consumption. The dietary product for use in the methods of the present invention may take the form of a solid or a beverage.

Methods of Identifying Mutations

In some embodiments, a test biological sample from a subject is assessed for the presence of at least one mutation in at least one gene associated with an antioxidant pathway, including, but not limited to an inactivating mutation of Keap1, an activating mutation of NRF2, or a mutation of a gene that results in an increase in NRF2 activity.

The test biological sample can be an in vitro sample or an in vivo sample. In various embodiments, the subject is a human subject, and may be of any race, sex and age. Representative subjects include those who are suspected of having cancer. In one embodiment, the cancer is lung cancer or pancreatic cancer.

In some embodiments, a binding molecule specific for an inactivating mutation of Keap1, an activating mutation of NRF2, or a mutation of a gene that results in an increase in NRF2 activity is used to identify a subject as having a tumor with increased levels of ROS. In some embodiments, the binding molecule is an antibody that specifically binds to an inactivating mutation of Keap1, an activating mutation of NRF2, or a mutation of a gene that results in an increase in NRF2 activity. In various embodiments, the binding molecule is detectably labeled. In some embodiments, the binding molecule is administered to a subject for a sufficient amount of time to allow the binding molecule to localize to the sites (e.g., tissues, cells, fluids, etc.) in the subject where Keap1, NRF2 or a targeted antioxidant pathway protein is present. The binding of the specifically-binding molecule, or specifically binding molecules, is then detected by various imaging methods, for example, by radiolocalization, radioimaging, magnetic resonance imaging (MRI), positron emission tomography (PET) scan, immuno-PET scan, and fluorescence imaging, by using, for example, a detectibly labeled binding molecule. When a combination of more than one specifically binding molecule is used, the ratio of the binding of the more than one specifically binding molecule can be determined and the ratio can be used as information for diagnosis. These imaging methods include MRI (for example, but not limited to, using a biotinylated antibody and avidin-iron oxide), PET (for example, but not limited to, using an antibody labeled with $^{68}$GA, $^{18}$F, $^{64}$Cu, $^{86}$Y, $^{76}$Br, $^{89}$Zr, $^{111}$In, or $^{124}$I), and optical imaging (for example, but not limited to, using luciferase or green fluorescent protein labeled antibodies). Examples of labeling and imaging assays useful with the compositions and methods of the invention include those described in Wu (2009, J. Nuclear Medicine 50:2-5), Valk et al. (2006, Positron Emission Tomography: Clinical Practice, Springer), Reilly (2010, Monoclonal Antibody and Peptide-Targeted Radiotherapy of Cancer, John Wiley and Sons), Schiepers and Allen-Auerbach (2006, Diagnostic Nuclear Medicine, Birkhauser), Kontermann (2010, Antibody Engineering, Springer), and Vallabhajosula (2009, Molecular Imaging: Radiopharmaceuticals for PET and SPECT, Springer).

In one embodiment, the test sample is a sample containing at least a fragment of a Keap1, NRF2, or antioxidant pathway protein or a nucleic acid molecule encoding at least a fragment of a Keap1, NRF2, or antioxidant pathway protein. The term, "fragment," as used herein, indicates that the portion of the polypeptide or nucleic acid (e.g., DNA, mRNA or cDNA) that is sufficient to identify it as a fragment of Keap1, NRF2, or an antioxidant pathway protein. In one representative embodiment, a fragment comprises at least one exon of Keap1, NRF2, or an antioxidant pathway protein. In another representative embodiment, a fragment comprises part of an exon of Keap1, NRF2, or an antioxidant pathway protein. In some embodiments, the fragment can also include an intron/exon junction of Keap1, NRF2, or an antioxidant pathway protein.

In some embodiments, the test sample is prepared from a biological sample obtained from the subject. The biological sample can be a sample from any source which contains a Keap1, NRF2, or an antioxidant pathway protein or nucleic acid (e.g., DNA, chromosomal nucleic acid, or RNA), such as a body fluid (e.g., blood, plasma, serum, etc.), or a tissue, or a tumor, or a cell, or a combination thereof. A biological sample can be obtained by appropriate methods, such as, by way of examples, biopsy or fluid draw. In certain embodiments, a biological sample containing genomic DNA is used. The biological sample can be used as the test sample; alternatively, the biological sample can be processed to enhance access to polypeptides, nucleic acids, or copies of nucleic acids (e.g., copies of nucleic acids comprising a mutation associated with an adrenal disease or disorder), and the processed biological sample can then be used as the test sample. For example, in various embodiments, nucleic acid (e.g., genomic DNA or cDNA prepared from mRNA) is prepared from a biological sample, for use in the methods. Alternatively, or in addition, if desired, an amplification method can be used to amplify nucleic acids comprising all or a fragment of an mRNA or genomic DNA in a biological sample, for use as the test sample in the assessment for the presence or absence of a mutation associated with decreased Keap1 activity, increased NRF2 activity, or an increased level of ROS.

The test sample is assessed to determine whether at least one mutation associated with decreased Keap1 activity, increased NRF2 activity, or an increased level of ROS are present in the polypeptide or nucleic acid of the subject. In general, detecting a mutation may be carried out by determining the presence or absence of a polypeptide or nucleic acid containing a mutation of interest in the test sample.

In various embodiments of the invention, methods of detecting at least one mutation associated with decreased Keap1 activity, increased NRF2 activity, or an increased level of ROS include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, a FACS assay, an enzyme-substrate binding assay, an enzymatic assay, an enzymatic assay employing a detectable molecule, such as a chromophore, fluorophore, or radioactive substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of a mutation associated with decreased Keap1 activity, increased NRF2 activity, or an increased level of ROS can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., at least one exon), a vector comprising the gene, a probe or primer, etc. For representative examples of use of nucleic acid probes, see, for example, U.S. Pat. Nos. 5,288,611 and 4,851,330.

In one embodiment, to detect at least one mutation of interest, a hybridization sample is formed by contacting the test sample with at least one nucleic acid probe. In one embodiment, a probe for detecting mRNA or genomic DNA is a labeled nucleic acid probe capable of hybridizing to mRNA, cDNA or genomic DNA. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA, cDNA or genomic DNA. The hybridization sample is maintained under conditions which are sufficient to allow specific hybridization of the nucleic acid probe to mRNA, cDNA or genomic DNA. Specific hybridization can be performed under high stringency conditions or moderate stringency conditions, as appropriate. In one embodiment, the hybridization conditions for specific hybridization are high stringency. Specific hybridization, if present, is then detected using standard methods. If specific hybridization occurs between the nucleic acid probe having a mutant sequence and a gene, mRNA or cDNA in the test sample, the mutation that is present in the nucleic acid probe is also present in the nucleic acid sequence of the subject. More than one nucleic acid probe can also be used concurrently in this method. Specific hybridization of any one of the nucleic acid probes is indicative of the presence of the mutation of interest, as described herein.

In Northern analysis, the hybridization methods described above are used to identify the presence of a mutation of interest in an RNA, such as a mRNA. For Northern analysis, a test sample comprising RNA is prepared from a biological sample from the subject by appropriate means. Specific hybridization of a nucleic acid probe, as described above, to RNA from the subject is indicative of the presence of a mutation of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising at least one mutation of interest. Hybridization of the PNA probe to a nucleic acid sequence is indicative of the presence of the mutation of interest.

In another embodiment of the methods of the invention, mutation analysis by restriction digestion can be used to detect a mutation associated with decreased Keap1 activity, increased NRF2 activity, or an increased level of ROS. A sample containing nucleic acid from the subject is used. Polymerase chain reaction (PCR) can be used to amplify all or a fragment of a nucleic acid (and, if necessary, the flanking sequences) in the sample. RFLP analysis is conducted as described (see Current Protocols in Molecular Biology, supra). The digestion pattern of the relevant fragments indicates the presence or absence of a mutation associated with decreased Keap1 activity, increased NRF2 activity, or an increased level of ROS.

Direct sequence analysis can also be used to detect specific mutations associated with decreased Keap1 activity, increased NRF2 activity, or an increased level of ROS. A sample comprising DNA or RNA can be used, and PCR or other appropriate methods can be used to amplify all or a fragment of the nucleic acid, and/or its flanking sequences, if desired. The sequence, or a fragment thereof (e.g., at least one exon), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of Keap1, NRF2 or an antioxidant pathway gene, as appropriate. The presence or absence of a mutation can then be identified.

Allele-specific oligonucleotides can also be used to detect the presence of a mutation associated with decreased Keap1 activity, increased NRF2 activity, or an increased level of ROS, through, for example, the use of dot-blot hybridization of amplified oligonucleotides with allele-specific oligonucleotide (ASO) probes (see, for example, 1986, Saiki et al., Nature 324:163-166). An "allele-specific oligonucleotide" (also referred to herein as an "allele-specific oligonucleotide probe") is an oligonucleotide of approximately 10-50 base pairs, in some instances approximately 15-30 base pairs, that specifically hybridizes to the mutant sequence, and that contains a mutation. An allele-specific oligonucleotide probe that is specific for a particular mutation can be prepared, using standard methods (see Current Protocols in Molecular Biology, supra). To identify a mutation associated with decreased Keap1 activity, increased NRF2 activity, or an increased level of ROS, a sample comprising nucleic acid is used. PCR can be used to amplify all or a fragment of the test nucleic acid sequence. The nucleic acid containing the amplified sequence (or fragment thereof) is dot-blotted, using standard methods (see Current Protocols in Molecular Biology, supra), and the blot is contacted with the oligonucleotide probe. The presence of specific hybridization of the probe to the amplified nucleic acid is then detected. Specific hybridization of an allele-specific oligonucleotide probe containing the mutation of interest, to test nucleic acid from the subject is indicative of the presence of the mutation of interest.

In another embodiment of the invention, fluorescence resonance energy transfer (FRET) can be used to detect the presence of a mutation. FRET is the process of a distance-dependent excited state interaction in which the emission of one fluorescent molecule is coupled to the excitation of another. A typical acceptor and donor pair for resonance energy transfer consists of 4-[[4-(dimethylamino) phenyl] azo]benzoic acid (DABCYL) and 5-[(2-aminoethylamino] naphthalene sulfonic acid (EDANS). EDANS is excited by illumination with 336 nm light, and emits a photon with wavelength 490 nxn. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the mutations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer in close proximity. The presence or absence of a mutation associated with decreased Keap1 activity, increased NRF2 activity, or an increased level of ROS interest can be assessed by comparing the fluorescence intensity profile obtained from the test sample, to fluorescence intensity profiles of control samples comprising known mutations of interest.

In another embodiment, arrays of oligonucleotide probes that are complementary to target nucleic acid sequence segments from a subject can be used to identify mutations associated with decreased Keap1 activity, increased NRF2 activity, or an increased level of ROS. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for mutations associated with decreased Keap1 activity, increased NRF2 activity, or an increased level of ROS. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes at least one previously identified mutation or marker is amplified by well-known amplification techniques, e.g., PCR. Typically, this involves the use of primer sequences that are complementary to the two strands of the target sequence both upstream and downstream of the mutation. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although often described in terms of a single detection block (e.g., for detection of a single mutation), arrays can include multiple detection blocks, and thus be capable of analyzing multiple, specific mutations. In alternate arrangements, it will generally be understood that detection blocks may be grouped within a single array or in multiple, separate arrays so that varying, optimal conditions may be used during the hybridization of the target to the array. This allows for the separate optimization of hybridization conditions for each situation. Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect mutations of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as $E.$ $coli$ mutS protein (see, for example, U.S. Pat. No. 5,459,039); Luminex xMAP™ technology; high-throughput sequencing (HTS) (2011, Gundry and Vijg, Mutat Res, doi:10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi:10.1038/nmeth.f.330; 2011, Rothberg et al., Nature 475:348-352) and/or allele-specific PCR, for example. These and other methods can be used to identify the presence of at least one mutation of interest in a biological sample obtained from a subject. In one embodiment of the invention, the methods of assessing a biological sample for the presence or absence of a mutation, as described herein, are used to identify a subject as having a tumor associated with increased ROS.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the cells using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a fresh or fixed tissue sample.

Routine methods also can be used to extract genomic DNA from a tissue sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. In one embodiment, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, in some embodiments, the nucleic acid probe is labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, at least 15 nucleotides, or at least 25 nucleotides, having a sequence complementary to a desired region of the gene, or mutant gene, of interest is hybridized in a sample, subjected to depolymerizing conditions, and the sample is treated with an ATP/luciferase system, which will luminesce if the nucleic sequence is present. In quantitative Southern blotting, levels of the mutant gene can be compared to wild-type levels of the gene.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. In one embodiment, the detection of the duplex is done using at least one primer directed to Keap1, NRF2 or an antioxidant pathway gene. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the Keap1, NRF2 or antioxidant pathway gene nucleic acid sequence are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. In one embodiment, the Tm for the amplification step is in the range of about 59° C. to about 72° C. In one embodiment, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

In one embodiment, the process for determining the quantitative and qualitative profile according to the present invention is characterized in that the amplifications are real-time amplifications performed using a labeled probe capable of specifically hybridizing in stringent conditions with a segment of a nucleic acid sequence of interest. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes is the Tm, which is in the range of about 65° C. to 75° C. In one embodiment, the Tm for any one of the hydrolysis-probes of the present invention is in the range of about 67° C. to about 70° C. In one embodiment, the Tm applied for any one of the hydrolysis-probes invention is about 67° C.

In another embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a nucleic acid sequence flanking the mutation of interest, and more particularly the primer includes 12 or more contiguous nucleotides substantially complementary to the sequence flanking the mutation of interest. In one embodiment, a primer featured in the invention includes a nucleotide sequence sufficiently complementary to hybridize to a nucleic acid sequence of about 12 to 25 nucleotides. In one embodiment, the primer differs by no more than 1, 2, or 3 nucleotides from the target flanking nucleotide sequence. In another aspect, the length of the primer can vary in length, in certain embodiments about 15 to 28 nucleotides in length (e.g., 16, 17, 18, 19, 20, 21, 22, 23, 24, 25, 26, or 27 nucleotides in length).

Kits of the Invention

The invention also includes a kit comprising compounds useful within the methods of the invention and an instructional material that describes, for instance, the method of administering the compositions as described elsewhere herein. The kit may comprise formulations of a pharmaceutical composition comprising the active ingredient combined with a pharmaceutically acceptable carrier, such as sterile water or sterile isotonic saline. The kit may comprise injectable formulations that may be prepared, packaged, or sold in unit dosage form, such as in ampules or in multi dose containers containing a preservative. The kit may comprise formulations including, but not limited to, suspensions, solutions, emulsions in oily or aqueous vehicles, pastes, and implantable sustained-release or biodegradable formulations. Such formulations may further comprise at least one additional ingredient including, but not limited to, suspending, stabilizing, or dispersing agents. In one embodiment of a kit, the active ingredient is provided in dry (i.e., powder or granular) form for reconstitution with a suitable vehicle (e.g., sterile pyrogen free water) prior to administration of the reconstituted composition.

The kit may comprise pharmaceutical compositions prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other formulations which are useful include those which comprise the active ingredient in microcrystalline form, in a liposomal preparation, or as a component of a biodegradable polymer system.

In certain embodiments, the kit comprises instructional material. Instructional material may include a publication, a recording, a diagram, or any other medium of expression which can be used to communicate the usefulness of the device or implant kit described herein. The instructional material of the kit of the invention may, for example, be affixed to a package which contains at least one instruments which may be necessary for the desired procedure. Alternatively, the instructional material may be shipped separately from the package, or may be accessible electronically via a communications network, such as the Internet.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, are not to be construed as limiting in any way the remainder of the disclosure.

Example 1: Activation of Oxidative Stress Response in Cancer Generates a Druggable Dependency on Exogenous Non-Essential Amino Acids The data presented here demonstrates that mutations in KEAP1 confer a dependency on exogenous uptake of multiple NEAAs in Kras-driven cell lines. The data demonstrates that KEAP1 mutant cells have increased uptake of NEAAs and are sensitive to deprivation of asparagine, glycine and serine in vitro and in vivo. Despite their ability to synthesize most NEAAs, KEAP1 mutant cells are unable to maintain amino acids pools by de novo synthesis under NEAA deprivation conditions. Blocking the efflux of glutamate thereby increasing intracellular glutamate levels through system $x_c^-$ inhibition is sufficient to rescue amino acid synthesis and cell proliferation under NEAA deprivation conditions. Furthermore, these phenotypes are Nrf2-dependent and can be acutely induced by use of a small molecule activator of Nrf2 or by chronic ROS-dependent post-translational activation of Nrf2 in Keap1 wildtype adenocarcinomas originating from both lung and pancreas. Importantly, pharmacologic or Nrf2-dependent restriction of intracellular glutamate can suppress tumor growth by either dietary or enzymatic depletion of NEAAs in vivo. Together the data provides evidence for a general mechanism by which intracellular glutamate availability dictates the dependency of cancer cells on exogenously supplied NEAAs and this dependency may be therapeutically exploited through pharmacologic or dietary intervention.

The materials and methods are now described.
Cell Lines and Culture

Murine $Kras^{G12D/+}$;$p53^{-/-}$ wildtype and Keap1 mutant isogenic clonal cell lines and LKR10/13 cell lines were previously established (Romero et al., 2017, Nat Med 23, 1362-1368). Additional KP parental cell lines were previously established and described (Dimitrova et al., 2016, Cancer Discov 6, 188-201). Murine $Kras^{G12D/+}$;$p53^{-/-}$ pancreatic cancer cell lines were provided by the Kimmelman lab. Human cell lines were acquired from ATCC. All cell lines tested negative for mycoplasma. All cell lines were cultured in a humidified incubator at 37° C. and 5% $CO_2$.

Cells were maintained in either DMEM or RPMI-1640 (Cellgro) supplemented with 10% fetal bovine serum (Sigma Aldrich) and gentamicin (Invitrogen).
Cell Proliferation and Viability Assays For cell proliferation assays conducted under different drug or media conditions as indicated, cells growing in DMEM were trypsinized, counted and plated into 12 well plate dishes (BD/Falcon) in 1 mL of RPMI media. For rescue experiments, cells were treated with indicated drugs after attachment, 500 nM Erastin (Sigma Aldrich), 6 mM Glutamate (Sigma Aldrich), 50 uM Trolox (Acros Organics), 0.5 mM N-acetyl-L-cysteine (NAC, Sigma Aldrich), 30 uM hypoxanthine, 3 mM formate (Sigma Aldrich), 16 μM thymidine (Sigma Aldrich), or 1 uM KI-696 (Nrf2 activator). For deprivation experiments, cells were washed with PBS and media was replaced with 1 mL of complete RPMI or RPMI lacking indicated amino acid and supplemented with 10% dialyzed FBS and cells were re-treated with indicated drugs. RPMI was prepared from a powder mix without amino acids (US Biological) according to manufacturer's instructions. All other amino acids besides those indicated were added to the RPMI mixture in the same concentrations present in RPMI-1640 formulation (Cellgro, Corning). Proliferation experiments were carried out for 5 days post drug treatment and collected by staining. Cells were stained with a 0.5% crystal violet (Fisher) solution in 20% methanol. Plates were then washed, dried, and crystal violet was eluted in 400 μL of 10% acetic acid.

For cell viability assays cells were plated in a white, opaque 96-well plate with clear bottom at a density of 1000 cells/well in RPMI or RPMI with modified amino acid content. After attachment, CB-839 (Selleck) or L-Asparaginase (AbCam) were added at the indicated concentrations. After 3 days, cell viability in the presence of all compounds was assessed by cell titer glo (Promega).
Animal Experiments $5 \times 10^5$ cells were implanted subcutaneously into C57B6 mice. Tumor volume was measured by caliper and volume was calculated (Length×Width$^2$×0.5). After tumor establishment phase (tumor volume ~50 mm$^3$), animals were randomized and assigned to a treatment group. Animals either received an amino acid control diet, diet lacking both serine and glycine, or a diet lacking asparagine (Envigo and TestDiet), 200 mg/kg CB-839 or vehicle (Calithera) twice daily administered through oral gavage as previously described (Davidson et al., 2016, Cell Metab 23, 517-528), 60 U of L-Asparaginase (Abcam) or vehicle once daily administered through intraperitoneal injection as before (Knott et al., 2018, Nature 554, 378-381) or some treatment combination as indicated.
Cell Line Generation (Keap1 Complement Cells & SLC1a3)

Keap1 complemented cells were generated by cloning mouse Keap1 cDNA into Gibson compatible lentiviral backbone with a hygromycin resistance cassette. Cells over expressing SLC1a3 were generated by cloning human SLC1a3 into the PMXS-puro retroviral backbone. Lenti or retroviruses were then produced by co-transfection of HEK293 cells with lentiviral or retroviral backbone constructs and packaging vectors (delta8.2 and VSV-G) using JetPrime (PolyPlus). Viral supernatant was collected 48 hours and 72 hours after transfection. Recipient cells were incubated with viral supernatant for 24 hours after each collection. Cells were then selected with either puromycin or hygromycin.

GC/MS Analysis of Polar Metabolites and Stable Isotope Tracing.

For analysis of cells, $1\times10^5$ cells were seeded in 1 mL of RPMI-1640 in 12 well plates. Where indicated, cells were pretreated with 6 mM glutamate, 500 nM Erastin or 1 uM KI696. Media was then replaced with fresh RPMI lacking serine or asparagine where indicated and supplement with 10% FBS. For tracing experiments media contained 11 mM $[U^{13}C]$-D-glucose, 2 mM $[U^{13}C]$-L-glutamine, 2 mM $[\alpha^{15}N]$-L-glutamine, or 285 µM $[U^{13}C]$-L-serine (Cambridge Isotope Laboratory). Cells were treated with 250 nM CB-839 and cultured for 1-3 hours. Cells were washed 2× in ice cold saline and then collected by scraping in 250 µL of 80% (v/v) of ice cold methanol containing 1.4 µg/mL norvaline (Sigma Aldrich). Samples were vortexed for 10 min at 4° C. and then centrifuged at max speed for 5 minutes. Supernatant was transferred to fresh tubes and then dried in a speed vac. For analysis of mouse plasma, whole blood was collected at the time of sacrifice by a retro-orbital bleed with heparin coated capillary tubes (Fisher) into EDTA containing microcentrifuge tubes. Whole blood was centrifuged for 5 minutes at 1600 g. Cleared plasma was transferred to fresh tubes and 4 µL of plasma was then aliquoted and used for analysis. 80% (v/v) methanol containing 1.4 µg/mL norvaline was added to plasma and samples were then dried in a speed vac. Dried metabolite extracts were then derivatized with 20 µL MOX reagent (Sigma) for 60 min at 37° C. and 30 µL of N-tert-butyldimethylsilyl-N-Methyltrifluoracetamide with 1% tert-Butyldimethylchlorosilane (TBDMS, Sigma) for 30 min at 37° C. After derivatization, samples were analyzed by GC-MS using an HP-5MS column (Agilent Technologies) in an Agilent Intuvo gas chromatograph coupled to an Agilent 5997B mass spectrometer. Helium was used as the carrier gas at a flow rate of 1.2 mL/minute. One microliter of sample was injected in split mode (split 1:1) at 270° C. After injection the GC oven was held at 100° C. for one minute and then increased to 300° C. at 3.5° C./min. The oven was then ramped to 320° C. at 20° C./min and held for 5 min at 320° C.

The MS system operated under electron impact ionization at 70 eV and the MS source and quadrupole were held at 230° C. and 150° C. respectively the detector was used in scanning mode, and the scanned ion range was 10-650 m/z. Mass isotopomer distributions were determined by integrating the appropriate ion fragments for each metabolite (Lewis et al., 2014, Molecular cell 55, 253-263) using MATLAB (Mathworks) and an algorithm adapted from Fernandez and colleagues (Fernandez et al., 1996, Journal of mass spectrometry: JMS 31, 255-262) that corrects for natural abundance.

The results of the experiments are now described.

KEAP1 Loss Increases Dependency on Exogenous Supply of NEAAs

Figure 1A:
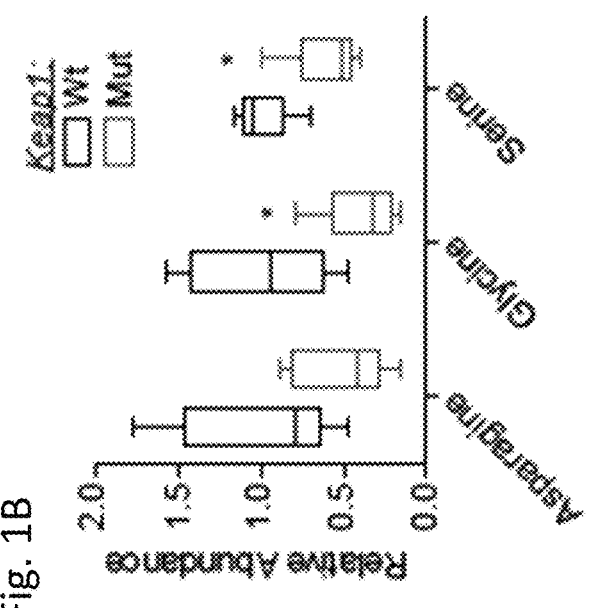
FIG. 1A through FIG. 1E depict exemplary data demonstrating that Keap1 loss increases dependency on exogenous supply of NEAAs.

KEAP1 mutations accelerate tumor progression (Romero et al., 2017, Nat Med 23, 1362-1368) and result in metabolic reprograming of cancer cells (DeNicola et al., 2015, Nat Genet 47, 1475-1481; Koppula et al., 2017, J Biol Chem 292, 14240-14249; Mitsuishi et al., 2012, Cancer Cell 22, 66-79; Romero et al., 2017, Nat Med 23, 1362-1368; Sayin et al., 2017, Elife 6), including depletion of intracellular glutamate levels (Romero et al., 2017, Nat Med 23, 1362-1368; Sayin et al., 2017, Elife 6). KEAP1 mutant tumors may possess an impaired ability to synthesize NEAAs and may be more reliant on exogenous sources to sustain amino acid pools. In order to identify differential amino acid requirements in tumors carrying KEAP1 mutations, in vitro uptake rates of NEAAs were profiled between isogenic mouse $Kras^{G12D/+}$; $p53^{-/-}$ mutant lung adenocarcinoma cell lines that are either wildtype (Wt) or Keap1 null (Mut) (Romero et al., 2017, Nat Med 23, 1362-1368). Indeed, Keap1 mutant cells exhibited increased uptake of a number of NEAAs including asparagine, glutamine, alanine, and glycine when compared to Keap1 wild-type cells (FIG. 1A). Using $[UC^{13}]$-L-serine, it was confirmed that Keap1 mutant cells uptake significantly more serine compared to Keap1 wildtype cells (FIG. 2A).

Figure 1B:
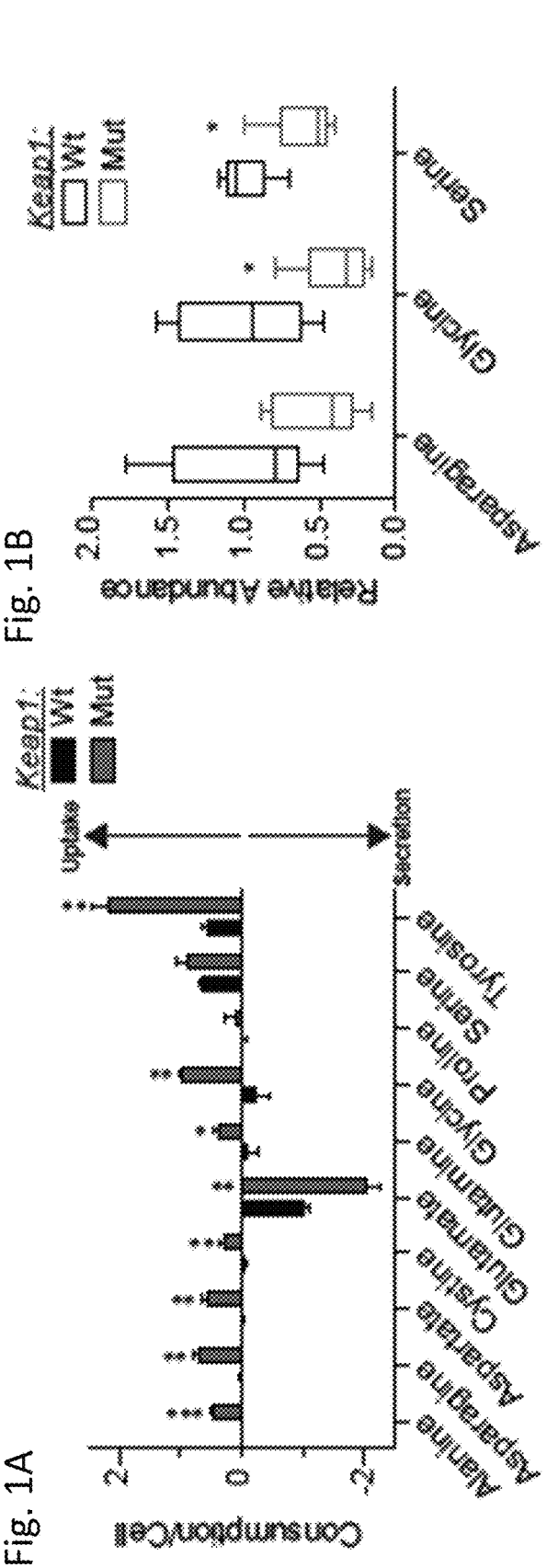

While Keap1 mutant cells uptake more NEAAs in vitro, cell metabolism can be drastically different in vivo (Davidson et al., 2016, Cell Metab 23, 517-528). To assess whether the increased uptake of NEAAs in vitro by Keap1 mutant cells is physiologically relevant in vivo, wildtype and Keap1 mutant cells were subcutaneously transplanted in C57B6/J syngeneic animals and the levels of NEAAs in the serum of tumor-bearing mice was monitored. Mice bearing Keap1 mutant tumors had decreased levels of multiple NEAAs, including serine and glycine (FIG. 1B and FIG. 2B).

Figure 1C:
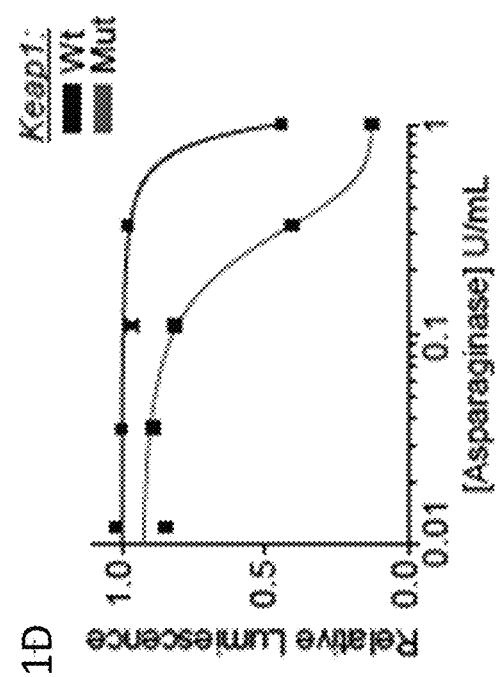
Figure 1D:
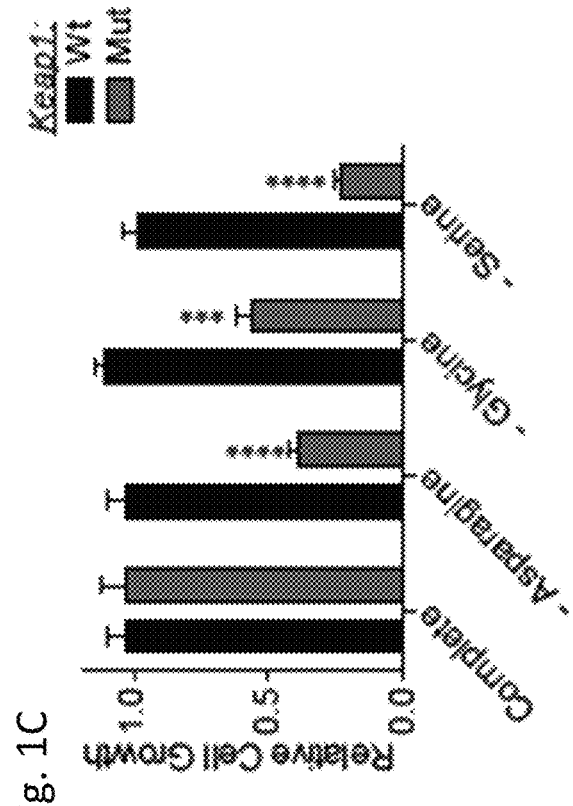

To assess whether this increased uptake of NEAAs is functionally relevant for the growth of Keap1 mutant cells, individual NEAAs were depleted from the media and a marked growth suppression of Keap1 mutant cells was observed upon depletion of asparagine, serine and glycine (FIG. 1C and FIG. 2C). Alanine, another highly consumed NEAA (FIG. 1A) could not be depleted from the media (present in serum but not in DMEM or RPMI). However, supplementation of alanine to Keap1 mutant cells led to an increase in cancer cell proliferation (FIG. 2D). Additionally, Keap1 mutant cells showed increased sensitivity to L-asparaginase (FIG. 1D), a recombinant enzyme that catalyzes the degradation of asparagine to glutamate and aspartate, which is currently used for the treatment of acute lymphoblastic leukemia (Richards and Kilberg, 2006, Annu Rev Biochem 75, 629-654).

Figure 1E:
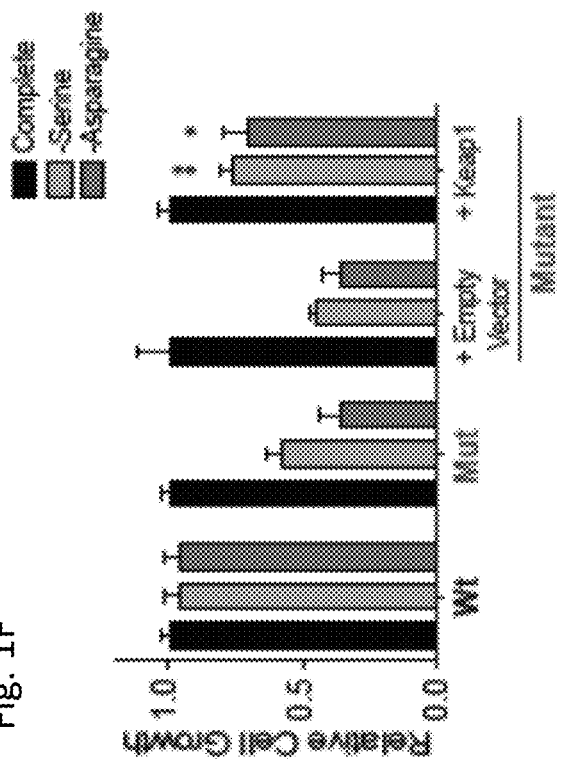
Figure 1F:
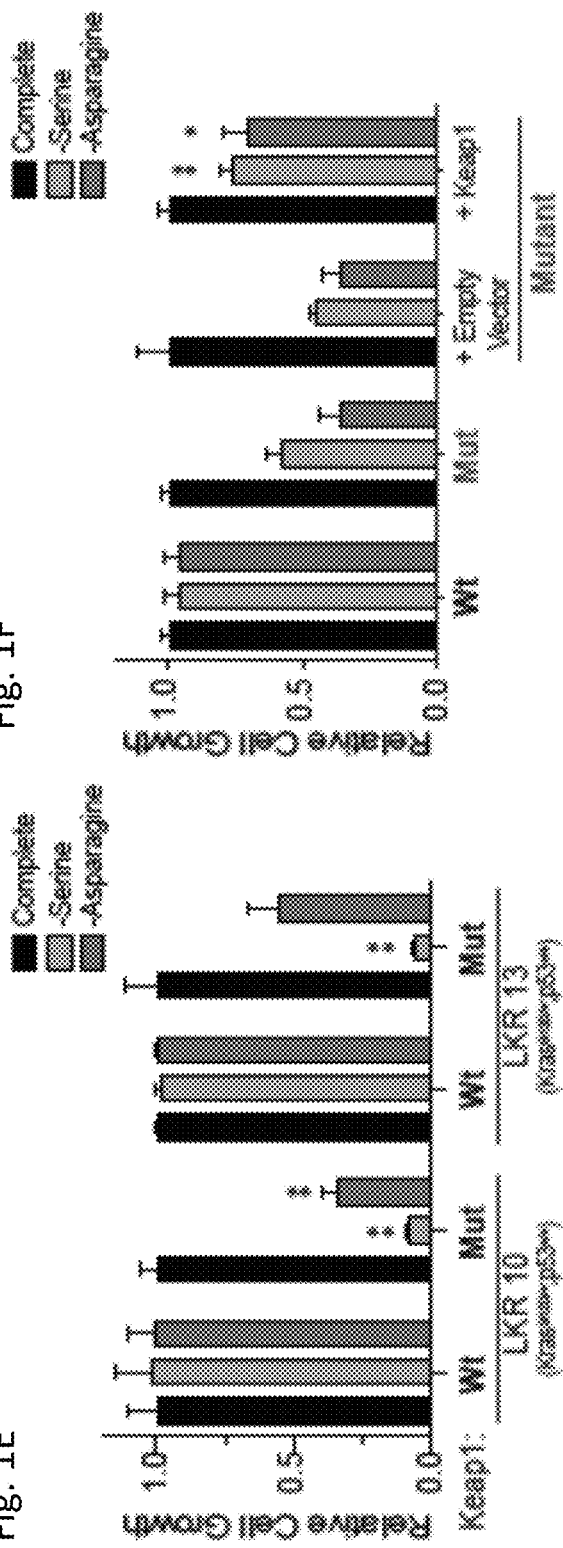
FIG. 1F depicts proliferation of wildtype, Keap1 mutant, and Keap1 mutant cells expressing an empty vector control or WT Keap1 in RPMI lacking serine or asparagine. All data points are relative to vehicle treated controls.
Figure 2F:
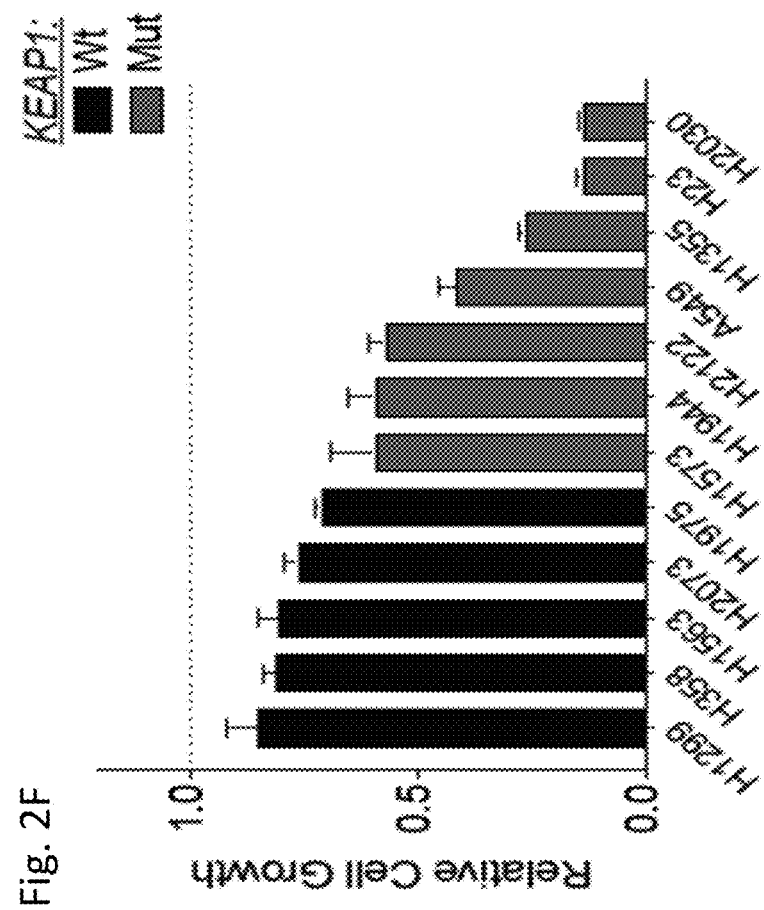
Figure 2E:
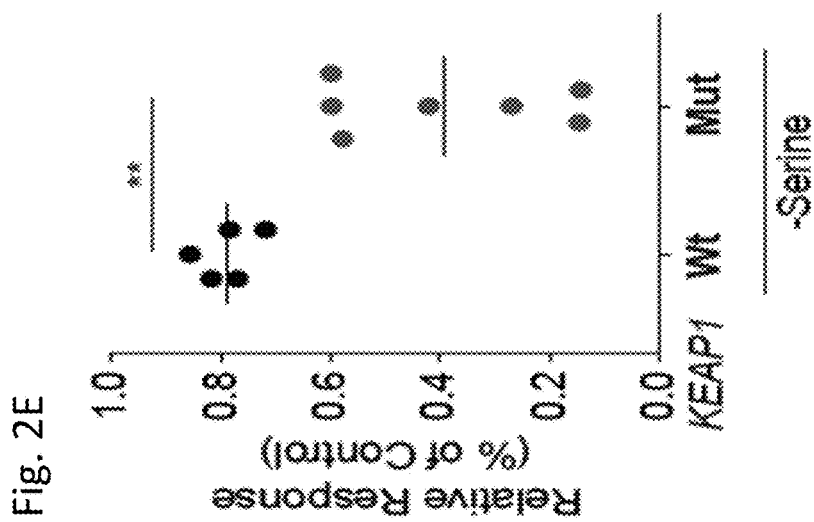
Figure 3A:
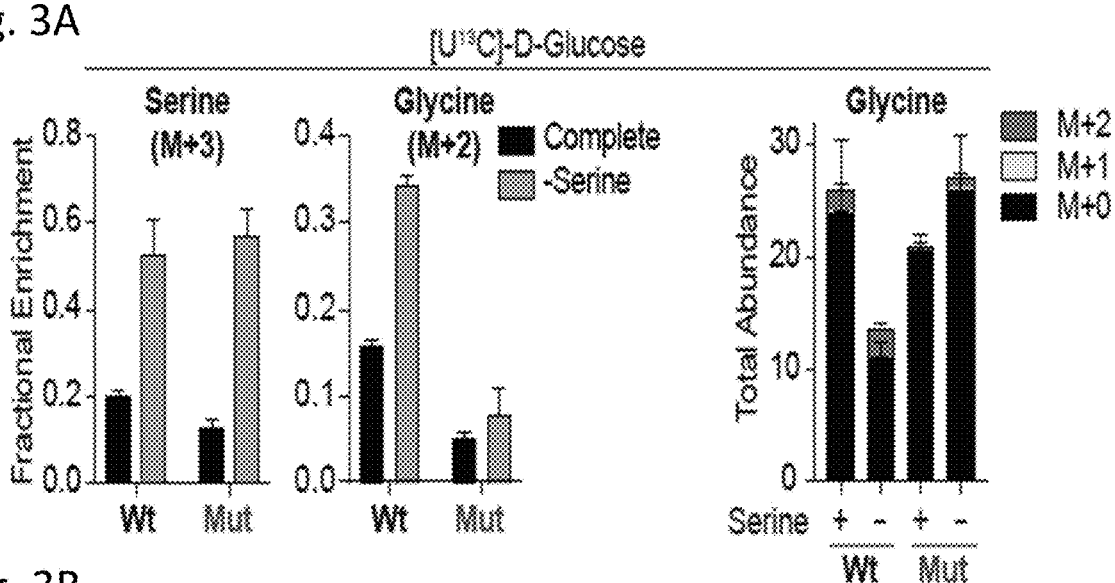
FIG. 3A through FIG. 3C depicts the results of exemplary experiments demonstrating that rates of NEAA synthesis are roughly equivalent between Keap1 mutant and wildtype cells.
Figure 3B:
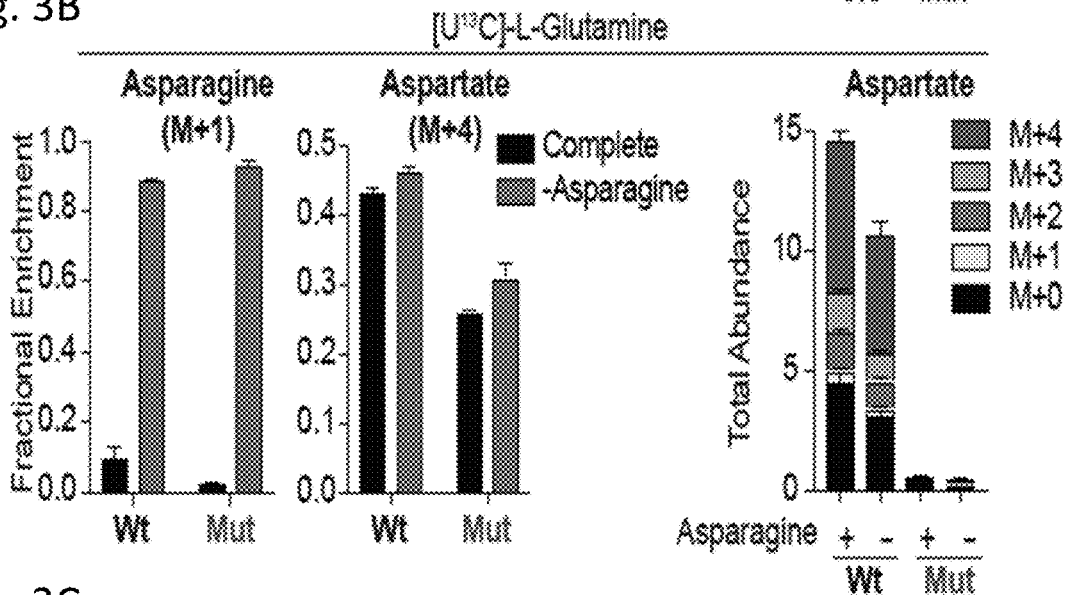
Figure 3C:
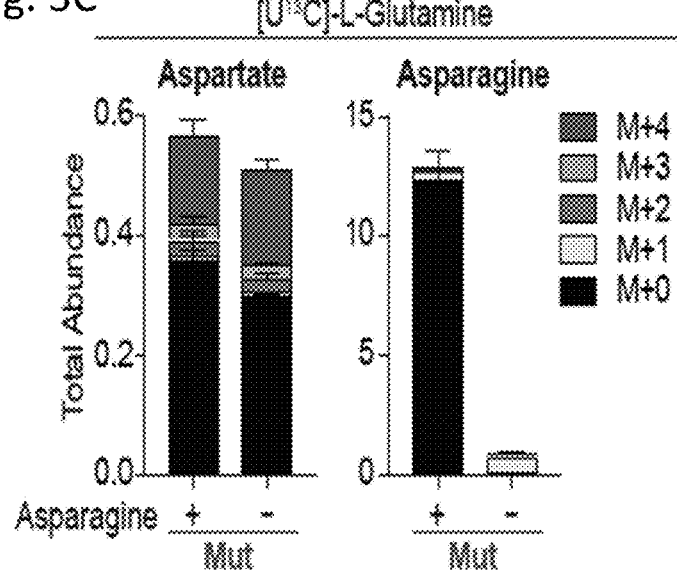

The genetic status of Trp53 has been previously shown to characterize dependency on exogenous serine (Maddocks et al., 2013, Nature 493, 542-546). To exclude the possibility that the observed dependency of Keap1 mutant cells on exogenous NEAAs is driven by loss of p53, $Kras^{G12D}$ mutant lung adenocarcinoma cell lines with wildtype p53 ($Kras^{G12D/+}$; $p53^{+/+}$; LKR10 and LKR13; (Meylan et al., 2009, Nature 462, 104-107)) were used that were either wildtype or mutant for Keap1 (Romero et al., 2017, Nat Med 23, 1362-1368; Sayin et al., 2017, Elife 6). Consistent with the data in p53 null Keap1 wildtype cells, Keap1 loss rendered p53 wildtype cells sensitive to both serine and asparagine deprivation (FIG. 1E). Additionally, genetic complementation of Keap1 by over-expression of wildtype Keap1 cDNA in Keap1 null cell lines, was sufficient to rescue sensitivity to serine and asparagine depletion (FIG. 1F), confirming that sensitivity to NEAA depletion is dependent on Keap1 loss. Similar, to mouse cells, human KEAP1 mutant lung adenocarcinoma cell lines were more sensitive to serine deprivation than KEAP1 wildtype cell lines (FIG. 2E and FIG. 2F). Taken together, these results indicate that Nrf2-activation generates a dependency on exogenous uptake of multiple NEAAs independent of the genetic status of Kras or p53.

Figure 1G:
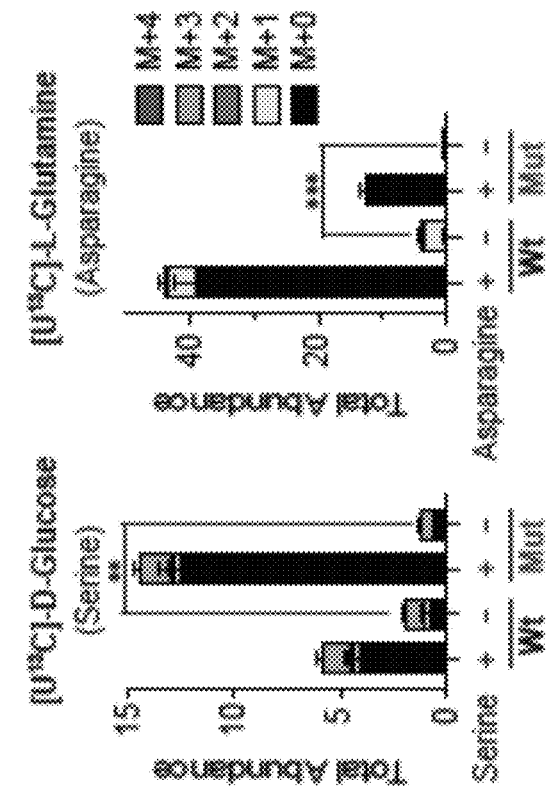
FIG. 1G depicts a schematic depicting synthesis of serine from glucose (top) and asparagine from glutamine (bottom). Filled blue circles represent 13C atoms derived from [U13C]-D-glucose or [U$^{13}$C]-L-glutamine.
Figure 1H:
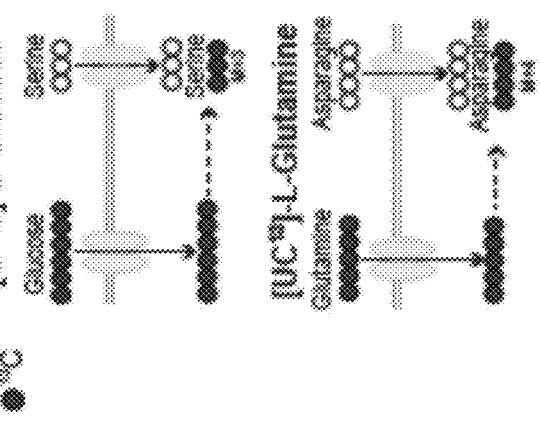
FIG. 1H depicts a mass isotopomer analysis of serine and asparagine in KP and KPK cells cultured in complete or amino acid deprived conditions. For serine, cells were cultured for 3 hrs with [U-C13]-D-glucose and for asparagine, cells were cultured for 3 hrs with [U$^{13}$C]-L-glutamine. Relative pool sizes are normalized to cell counts for each condition. All error bars depict s.e.m. *p<0.05, p<0.01, *p<0.001, ****p<0.0001.

It was examined whether the increased uptake of NEAAs may be a result of increased basal demand in Keap1 mutant cells, and whether when exogenous NEAAs are depleted from the culture media, rates of de novo synthesis in Keap1 mutant are insufficient to sustain cellular proliferation. To test this, stable isotope tracing was performed with $[UC^{13}]$-D glucose and $[UC^{13}]$-L glutamine to assess synthesis of NEAAs in replete as well as serine and asparagine deprived conditions (FIG. 1G). It was observed that when serine or asparagine are depleted from the culture media, rates of NEAA synthesis are roughly equivalent between Keap1 mutant and wildtype cells (FIG. 1H and FIG. 3A-FIG. 3C). However, when serine or asparagine are removed from the media the total pool of these metabolites is significantly reduced in Keap1 mutant compared to wildtype cells (FIG. 1H) suggesting that de novo synthesis in Keap1 mutant cells is unable to maintain adequate pools of these metabolites to sustain proliferation in nutrient depleted conditions (FIG. 1C). These findings are consistent with the idea that to support growth and increased anabolism, Keap1 mutant cells rely on uptake of exogenous NEAAs.

Acute Activation of Nrf2 Induces Dependency on Nonessential Amino Acids

Given that genetic activation of Nrf2 in Keap1 mutant cells leads to a dependency on exogenous serine and asparagine, it was examined whether pharmacological dependent stabilization of Nrf2 may lead to a similar metabolic demand. Indeed, it was observed that acute activation of Nrf2 with a small molecule activator (KI696) (Davies et al., 2016, Journal of medicinal chemistry 59, 3991-4006; Sayin et al., 2017, Elife 6) led to suppression of growth upon deprivation of serine or asparagine (FIG. 4A and FIG. 4B) or treatment with L-asparaginase (FIG. 4C). Furthermore, to ensure this is not a cell line specific phenomenon, a panel of five different murine lung adenocarcinoma $Kras^{G12D/+}$; $p53^{-/-}$ cell lines was used and it was demonstrated that small molecule induced activation of Nrf2 led to a dependency on exogenous serine and asparagine (FIG. 5A). Similarly, dependency on exogenous NEAAs was independent of p53 status as Nrf2 activation in p53 wildtype ($Kras^{G12D/+}$; $p53^{+/+}$) LKR lines lead to growth suppression in serine or asparagine depleted conditions (FIG. 5B).

Furthermore, it was examined whether Nrf2 activation would lead to dependency on exogenous NEAAs independent of cancer subtype. To test this, a murine $Kras^{G12D/+}$; $p53^{-/-}$ pancreatic ductal adenocarcinoma cell line was treated with the Nrf2 activator and robust growth suppression was observed upon serine deprivation or treatment with L-asparaginase (FIG. 5C and FIG. 5D).

Oxidative Stress Sensitizes Keap1 Wildtype Cells to NEAA Deprivation

Figures 5E, 5F:
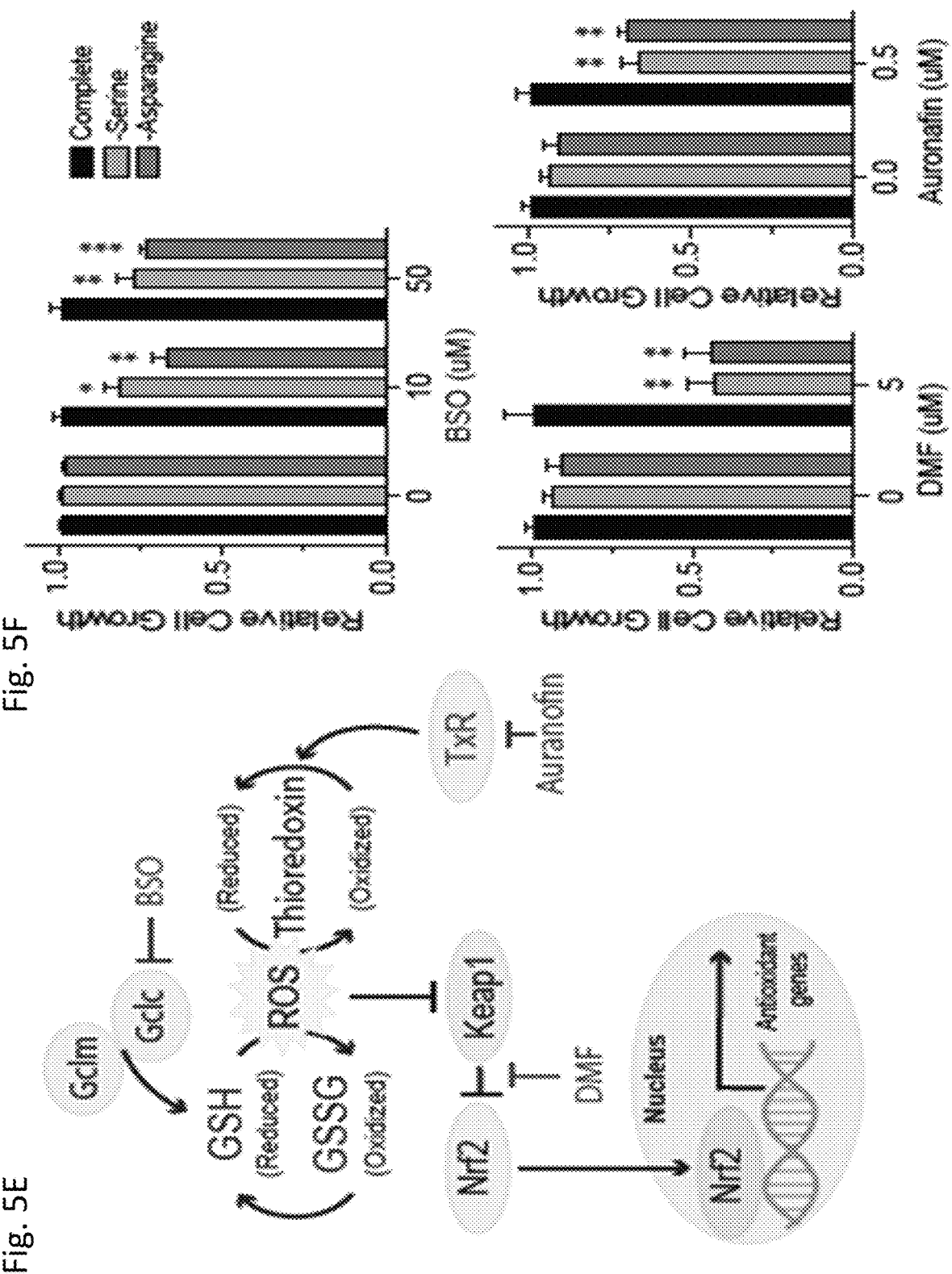

Activation of Nrf2 either through genetic loss of Keap1 or by pharmacological activation strongly sensitizes cells to NEAA depletion. In wildtype cells, Nrf2 is stabilized in response to ROS-dependent post-translational modifications of Keap1 and remains active until ROS are cleared. It was examined whether, during periods of chronic ROS stress, wildtype cells would undergo Nrf2-mediated metabolic rewiring and would therefore efflux glutamate through system $x_c^-$ and become sensitive to NEAA depletion, similar to Keap1 mutant cells. To test this, wildtype cells were treated with various oxidants that interfere with different arms of the endogenous anti-oxidant response and activate Nrf2. Using a Thioredoxin reductase (TxR) inhibitor (Auranofin) (Urig and Becker, 2006), an inhibitor of GSH synthesis (L-buthionine-sulfoximine, BSO) (Griffith and Meister, 1979) and a general oxidative stress agent that will react with free cysteines (di-methyl fumarate, DMF) (Wang et al., 2015, International Journal of Molecular Sciences 16, 13885-13907), whether Keap1 wildtype cells would become dependent on exogenous NEAAs (FIG. 5E) was assessed. Indeed, it was observed that wildtype cells were sensitized to NEAA depletion in the context of all three oxidative stress agents (FIG. 5F).

Low Intracellular Glutamate Levels in Cells with Nrf2 Activation Generates a Dependency on Exogenous NEAAs NEAAs are synthesized from α-ketoacids to which an amino group is added via a glutamate or glutamine-dependent transamination reaction (Lehninger et al., 2000, Principles of Biochemistry). Previously, it was reported that Nrf2 activation leads to a marked decrease in intracellular glutamate by utilization of glutamate for glutathione synthesis and the secretion of glutamate through system $x_c^-$ to enable cystine uptake (Romero et al., 2017, Nat Med 23, 1362-1368; Sayin et al., 2017, Elife 6). Given the increased dependency of cells with Nrf2 activation on exogenous NEAAs, it was examined whether increasing intracellular glutamate levels, either by inhibiting system $x_c^-$ or by expressing additional glutamate transporters (FIG. 6A), would enhance synthesis of NEAAs and decrease the dependency of Keap1 mutant cells on exogenous NEAAs. To inhibit system $x_c^-$ activity, cells were either pretreated with the small molecule inhibitor Erastin (Dixon et al., 2014, Elife 3, e02523) or high glutamate (6 mM) which forces the import of glutamate and export of cystine through system $x_c^-$ in a concentration dependent manner (Briggs et al., 2016, Cell 166, 126-139; Sayin et al., 2017, Elife 6; Watanabe and Bannai, 1987, The Journal of experimental medicine 165, 628-640). Both Erastin and glutamate treatment of Keap1 mutant cells significantly increased intracellular glutamate levels (FIG. 6B and FIG. 6C) and were able to completely rescue Keap1 mutant cell growth when serine or asparagine were depleted from the media (FIG. 6D and FIG. 6E), or when cells were treated with L-asparaginase (FIG. 4D). In line with what was observed in murine lung adenocarcinoma, glutamate was also able to rescue sensitivity to NEAA depletion in a murine pancreatic ductal adenocarcinoma cell line after pharmacological activation of Nrf2 (FIG. 4E).

As a negatively charged amino acid, glutamate cannot freely diffuse across the plasma membrane and requires a dedicated transporter to enter the cell. To increase glutamate uptake, SLC1A3 (Garcia-Bermudez et al., 2018, Nat Cell Biol 20, 775-781), a glutamate transporter that is normally expressed in the central nervous system by glial cells (Storck et al., 1992, Proc Natl Acad Sci USA 89, 10955-10959), was over-expressed. Expression of SLC1A3 resulted in dramatic increase in the re-uptake of glutamate which is normally exported through system $x_c^-$ (FIG. 6F) and as expected, rescued sensitivity of Keap1 mutant cells to glutaminase inhibition by CB-839 (FIG. 4F) (Romero et al., 2017, Nat Med 23, 1362-1368; Sayin et al., 2017, Elife 6). Similar to treatment with glutamate or Erastin, expression of SLC1A3 completely rescued Keap1 mutant cell growth when serine and asparagine were depleted from the culture media (FIG. 6G and FIG. 6J) or when treated with L-asparaginase (FIG. 4G).

Previously, it has been shown that Keap1 mutant cells are highly sensitive to CB-839, a glutaminase inhibitor which blocks the conversion of glutamine to glutamate (Romero et al., 2017, Nat Med 23, 1362-1368; Sayin et al., 2017, Elife 6). Since increasing intracellular glutamate levels rescues cell growth when serine and asparagine are limited, it was examined whether CB-839 treatment would decrease glutamine-derived glutamate and NEAA synthesis, and further sensitize Keap1 mutant cells to NEAA deprivation. Cells were cultured in either 0.1 U/mL of L-asparaginase or reduced the amount of serine in the media to 10% of its normal concentration. An increased sensitivity of Keap1 mutant cells to very low doses of CB-839 was observed (FIG. 6I and FIG. 6J), which alone do not affect cell growth, suggesting possible synergistic effects of combining glutaminase treatment with NEAA deprivation. These results suggest that the increased efflux of glutamate by Keap1 mutant cells generates a major bottleneck in their ability to sustain amino acid pools under NEAA deprived conditions. Furthermore, by blocking the secretion of glutamate and increasing intracellular glutamate pools by modulating the concentration of glutamate and cystine in the microenvironment, cells are able to maintain NEAA synthesis under nutrient deprived conditions. Together these data show that intracellular glutamate levels determine a cell's dependency on exogenous NEAAs.

Glutamate Availability Restricts Serine Biosynthesis

In addition to protein synthesis, serine is an important carbon source to generate nucleotides, methyl groups, other amino acids, and contributes to GSH synthesis (DeNicola et al., 2015, Nat Genet 47, 1475-1481; Mehrmohamadi and Locasale, 2015, Molecular & cellular oncology 2, e996418; Yang and Vousden, 2016, Nat Rev Cancer 16, 650-662). To determine which of these metabolites is limiting during serine deprivation supplementation with antioxidants was tested to restore redox buffering or nucleotides could rescue Keap1 mutant cell growth in serine deprived conditions. Supplementation with the antioxidants N-acetylcysteine (NAC) or Trolox, did not rescue cell growth under serine deprived conditions FIG. 7A and FIG. 8A. However, supplementation with formate, which rescues the one-carbon cycle, or thymidine, which rescues nucleotide synthesis, led to a complete rescue of cell growth in Keap1 mutant cells under serine deprived conditions. This data suggests that nucleotide synthesis, and not antioxidant availability limits growth of Keap1 mutant cells in serine depleted conditions.

Serine can be synthesized de novo from glucose in a multi-step reaction. The enzyme phosphoserine aminotransferase (PSAT) is the transaminase that transfers the amino group from glutamate to phosphohydroxypyruvate (PHP) to generate phosphor-serine and α-ketoglutarate (FIG. 7B) (DeNicola and Cantley, 2015). It was examined whether rescue of Keap1 mutant cell growth in the absence of exogenous serine by Erastin or glutamate supplementation was due to increasing glutamate availability for serine biosynthesis. To test this, PSAT knockout wildtype and Keap1 mutant cells were generated using CRISPR/Cas9. The ability of Erastin or glutamate to rescue cell growth in serine deprivation is dependent on the presence of PSAT (FIG. 7C and FIG. 8B), suggesting that increasing intracellular glutamate levels rescues cell growth in the absence of serine by restoring serine biosynthesis.

Figure 8E:
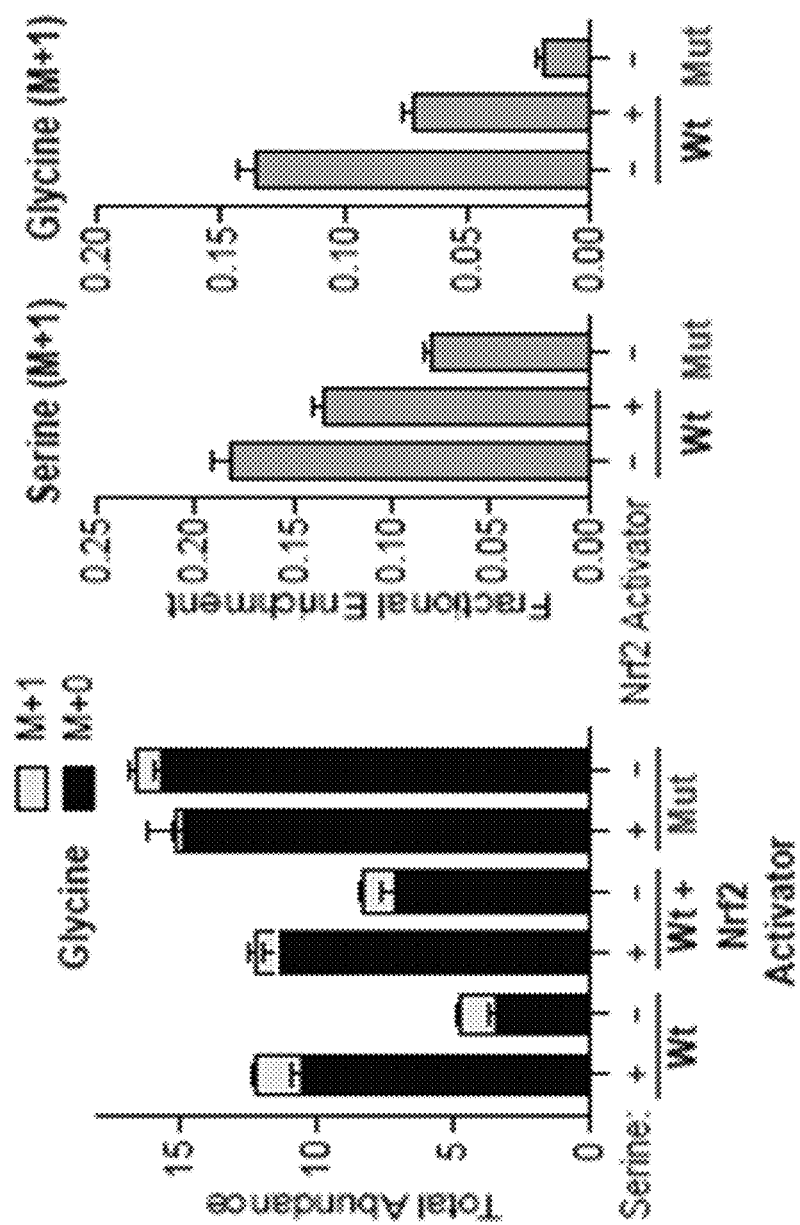
Figure 8D:
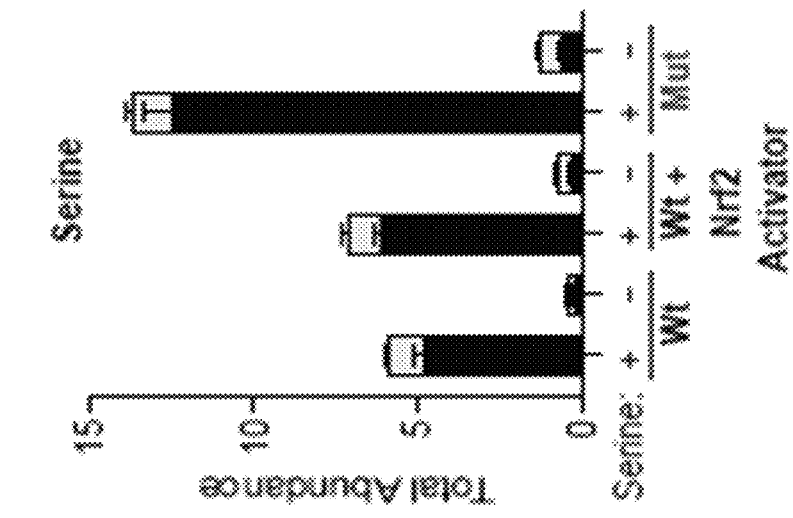

To confirm that modulation of intracellular glutamate levels alters serine biosynthesis, stable isotope tracing of $[U^{13}C]$-D glucose in serine depleted conditions was performed and $C^{13}$ incorporation into newly synthesized serine and its downstream metabolite, glycine (FIG. 7D) was evaluated. When glutamate availability was limited by treatment with CB-839 there was a decrease in both serine and glycine synthesis (FIG. 7E). Conversely, when intracellular glutamate was increased by glutamate supplementation an increase in both serine and glycine synthesis (FIG. 7E and FIG. 8C) was observed. To confirm that the nitrogen from glutamate is used for serine synthesis, cells were cultured in the presence of $[\alpha^{15}N]$-L glutamine to determine the fate of the amino group of glutamate (FIG. 7F). It was observed that serine deprivation increases the incorporation of labeled nitrogen in both serine and glycine (FIG. 7G and FIG. 8D). Additionally, decreased incorporation of labeled nitrogen in Keap1 mutant cells is seen in serine deprived conditions (FIG. 7G and FIG. 8E) suggesting that diminished glutamate availability in Keap1 mutant cells reduces serine synthesis. This is further supported by treating Keap1 wildtype cells with a small molecule activator of Nrf2 which subsequently results in decreased incorporation of labeled nitrogen in serine and glycine (FIG. 7G and FIG. 8E).

Keap1 Mutant Tumors Require Exogenous NEAAs In Vivo

Figure 9E:
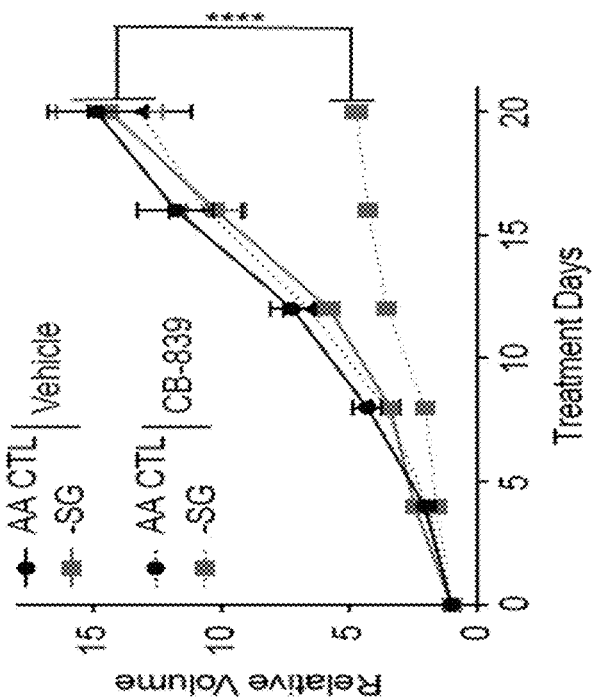
Figure 10A:
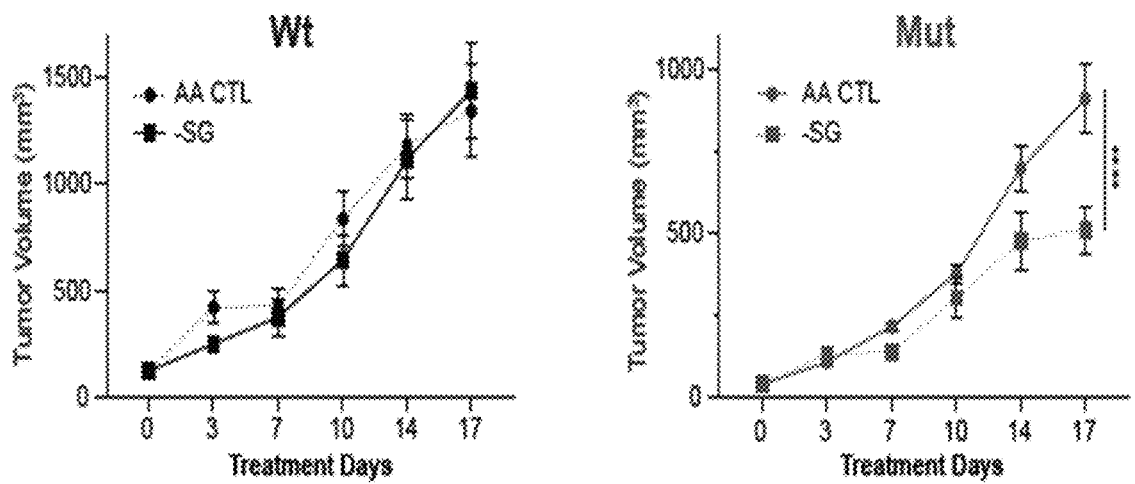
FIG. 10A through FIG. 10C depicts the results of exemplary experiments demonstrating that Keap1 mutant tumors require exogenous NEAAs in vivo.
Figure 10B:
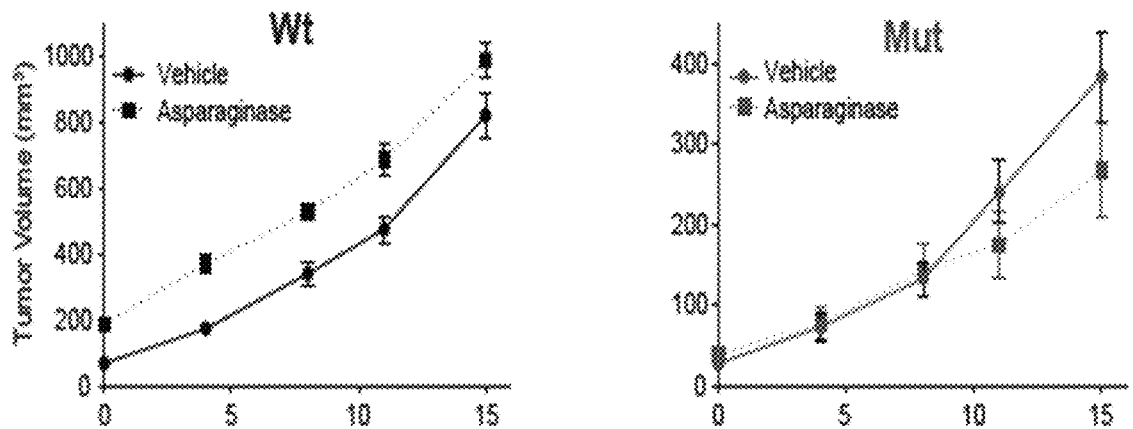
Figure 10C:
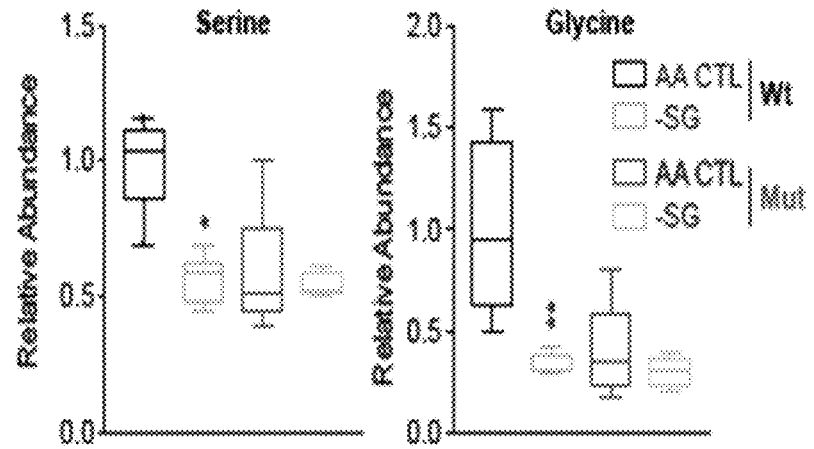
Figure 11A:
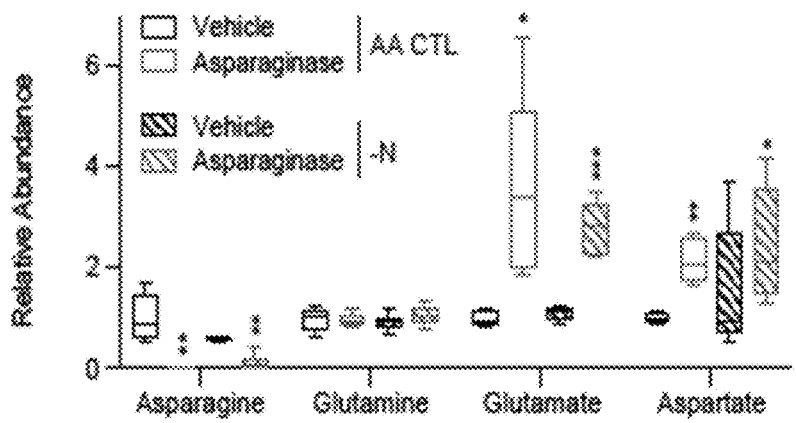
FIG. 11A through FIG. 11C depicts the results of exemplary experiments demonstrating that amino acid defined diets and L-asparaginase treatments impact amino acid levels.
Figure 11B:
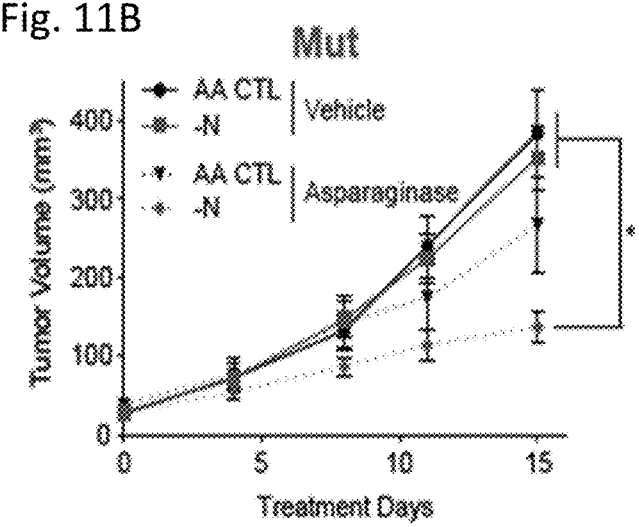
Figure 11C:
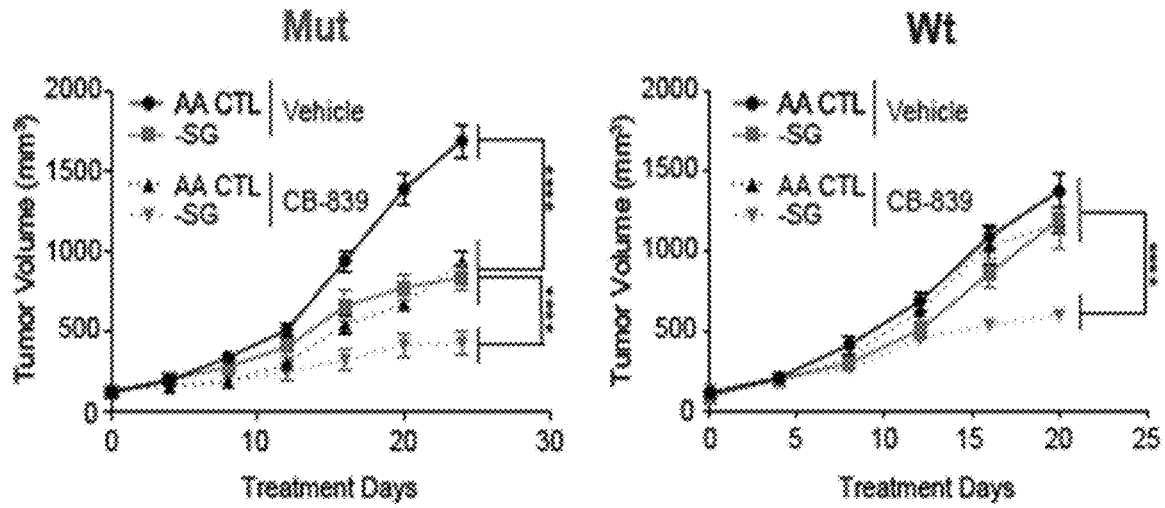

Given the differential sensitivity of Keap1 mutant and wildtype cells to exogenous serine or asparagine depletion in vitro, their dependency on these NEAAs in vivo was assessed. To do so, a diet lacking both serine and glycine (−SG) (Maddocks et al., 2013, Nature 493, 542-546; Maddocks et al., 2017, Nature 544, 372-376), or a diet lacking asparagine were utilized, or mice were treated with L-asparaginase (Gwinn et al., 2018, Cancer Cell 33, 91-107.e106; Knott et al., 2018, Nature 554, 378-381). Mice were subcutaneously injected with either wildtype or Keap1 mutant cells and upon tumor formation mice were randomized to different treatment groups. When depleting dietary serine and glycine (−SG), growth of Keap1 mutant tumors was significantly attenuated compared to mice with Keap1 mutant tumors on an amino acid control diet (AA CTL) (FIG. 9A and FIG. 10A). In contrast, no effect was observed on wildtype tumor growth in response to −SG diet (FIG. 9A and FIG. 10A). Similarly, treatment with L-asparaginase, or a diet lacking asparagine (−N) blunted growth of Keap1 mutant but not wildtype tumors (FIG. 9B, FIG. 9C and FIG. 10B). To validate that the amino acid defined diets and L-asparaginase treatments are impacting amino acid levels, depletion of serine, glycine, and asparagine was confirmed in plasma (FIG. 10C and FIG. 11A). In the case of asparagine, treatment with L-asparaginase was more effective at reducing plasma levels of asparagine than the asparagine diet (FIG. 11A). While not wishing to be bound by any particular theory, this is likely because L-asparaginase is able to degrade circulating asparagine coming from the diet or that is produced by other cells while the asparagine deficient diet only eliminates dietary sources of asparagine. When combining an asparagine free diet with L-asparaginase treatment, the asparagine free diet alone results in a moderate reduction in tumor growth, but L-asparaginase treatment alone or in combination with the asparagine diet strongly blunts the growth of Keap1 mutant tumors (FIG. 9D and FIG. 11B). These results are in line with the degree to which asparagine is reduced in the plasma for each treatment group (FIG. 11A).

Figure 9F:
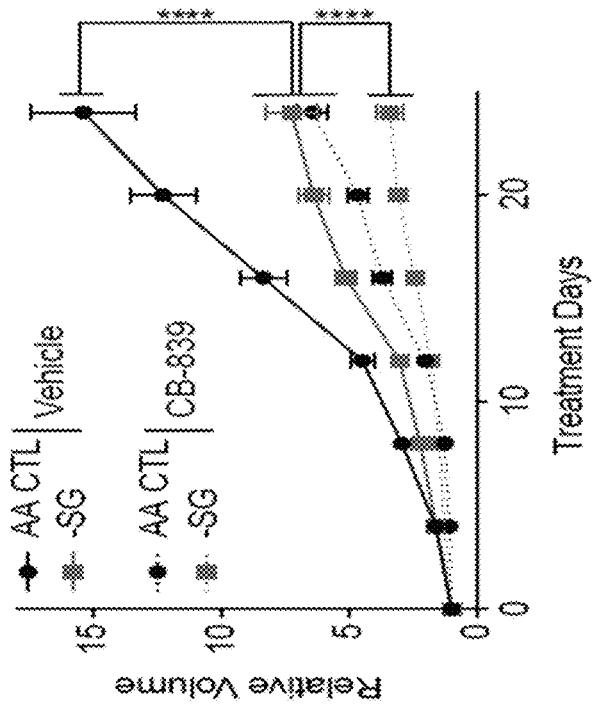

As NEAA limitation was synergistic with CB-839 treatment in vitro (FIG. 6I and FIG. 6J), the impact of combining −SG diet with CB-839 treatment was evaluated in vivo. As has been previously shown, Keap1 mutant but not wildtype tumors are sensitive to treatment with CB-839 (Romero et al., 2017, Nat Med 23, 1362-1368) (FIG. 9E and FIG. 9F). −SG diet along with CB-839 treatment further reduced Keap1 mutant tumor growth in mice compared to either monotherapy. Surprisingly, wildtype tumors were extremely sensitive to combination therapy (FIG. 9F). −SG diet or CB-839 treatment alone had no effect on wildtype tumor growth. However, administration of CB-839 in combination with the −SG diet had a strong synergistic effect and significantly reduced wildtype tumor growth (FIG. 9F). Taken together, using both defined diets and enzymatic methods to deplete NEAAs, the data demonstrate that Keap1 mutant tumors have an increased dependency on exogenous NEAAs in vivo. Furthermore, using existing therapeutic strategies to decrease intracellular glutamate levels, tumor growth can be suppressed by limiting exogenous NEAAs in Keap1 WT tumors. These results provide novel therapeutic strategies for targeting Kras mutant NSCLC.

Rewiring of cellular metabolism is a hallmark of cancer and is necessary to sustain chronic cellular proliferation (Hanahan and Weinberg, 2011, Cell, 144, 646-674). The activation of oncogenes and loss of tumor suppressors directly regulates metabolism to support increased cell growth (Heiden and DeBerardinis, 2017, Cell 168, 657-669; Vander Heiden et al., 2009, Science (New York, N.Y.) 324, 1029-1033). Although, much effort has been focused on understanding how changes to tumor cell metabolism can be leveraged for effective cancer therapies, there is a limited understanding of the metabolic differences between common genetic subtypes of cancer and how those can be targeted by rationale metabolic therapies. Nrf2 activation by Keap1 mutation results in the system $x_c^-$ dependent export of glutamate, depleting intracellular glutamate levels (Romero et al., 2017, Nat Med 23, 1362-1368; Sayin et al., 2017, Elife 6) (FIG. 6B, FIG. 6C and FIG. 6F). It was examined whether low intracellular glutamate in Keap1 mutant tumors might impose a limitation for NEAA synthesis under conditions of nutrient stress. NEAAs are important building blocks for proteins, serve as signaling molecules (Briggs et al., 2016, Cell 166, 126-139; Larson et al., 2007, Gastrointestinal and liver physiology 293, G1262-1271; Nicklin et al., 2009, Cell 136, 521-534; Rhoads et al., 1997, The American journal of physiology 272, G943-953), generate essential co-factors and reducing molecules, and are substrates for other macromolecules (Mehrmohamadi and Locasale, 2015, Molecular & cellular oncology 2, e996418). Targeting NEAA availability and synthesis in tumors is an attractive therapeutic strategy as highly proliferating tumor cells often require NEAAs in excess of what de novo synthesis can provide (DeNicola and Cantley, 2015, Molecular cell 60, 514-523).

Here it is demonstrated that limited glutamate availability reduces de novo synthesis of NEAAs (FIG. 1H, FIG. 3, FIG. 7) and drives dependency of Keap1 mutant cells on multiple NEAAs including serine, glycine, and asparagine (FIG. 6D, FIG. 6E, FIG. 6G and FIG. 6H), in a system $x_c^-$-dependent manner. Modulation of glutamate or cystine in the microenvironment can either enhance or restrict cancer cell growth in the context of NEAAs depletion. Further, combined depletion of multiple NEAAs in vitro (FIG. 6I and FIG. 6J) and in vivo (FIG. 9E) has a greater effect in reducing tumor growth in Keap1 mutant tumors. Keap1 mutant cells uptake more NEAAs compared to wildtype cells both in vitro and in vivo and are sensitive to their depletion even as monotherapies (FIG. 1A through FIG. 1D).

This phenotype is Nrf2-dependent (FIG. 4A through FIG. 4C, FIG. 5A, and FIG. 5B), as acute activation of Nrf2 is sufficient to sensitize Keap1 wildtype cells to NEAA depletion in multiple contexts. While the pharmacokinetics of the Nrf2 activator prevent its efficient use in vivo (Davies et al., 2016, Journal of medicinal chemistry 59, 3991-4006), strategies to increase ROS to elevate NRF2 activity are promising ways to sensitize wildtype cells to NEAA depletion (Maddocks et al., 2017, Nature 544, 372-376). Indeed, wildtype cells can be sensitized to serine and asparagine depletion by pre-treatment with oxidants (FIG. 5E). This suggests that modulation of NEAA availability may be widely applicable to both Keap1 mutant and wildtype tumors.

Furthermore, activation of Nrf2 in other cancer subtypes, such as pancreatic cancer, is sufficient to sensitize cells to NEAA deprivation (FIG. 5B and FIG. 5C) indicating that activation of the endogenous antioxidant response via Nrf2 stabilization results in a metabolic phenotype that persists regardless of tissue of origin. Furthermore, pharmacological depletion of intracellular glutamate levels (CB-839) strongly sensitizes Keap1 wildtype tumors to dietary restriction of serine and glycine (FIG. 9F), similar to what is observed in Keap1 mutant tumors (FIG. 9D).

The data provided herein highlights the importance of understanding how particular mutations, other than the well-known drivers (eg. Kras, p53), can strongly impact the metabolic landscape of tumors and their response to metabolic therapies. For example, previously it has been shown that Kras and p53 status is important in regulating serine metabolism and cell survival during serine deprivation (Maddocks et al., 2013, Nature 493, 542-546; Maddocks et al., 2017, Nature 544, 372-376). However, the effect of Keap1 mutations on glutamate availability for NEAA synthesis "overrides" the effects of oncogenic KRAS or p53 mutation on serine and glycine deprivation. These observations further emphasize the need for more comprehensive metabolic characterization of various genotypic subtypes of cancer.

Figure 12A:
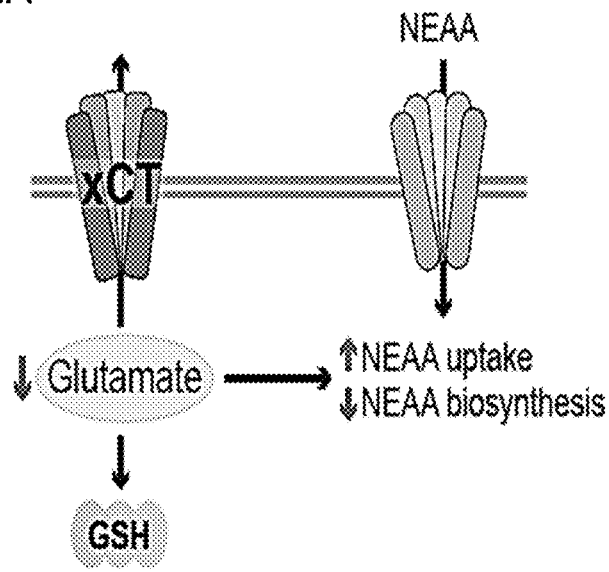
FIG. 12A and FIG. 12B depict the results of exemplary experiments demonstrating that activation of oxidative stress response depletes intracellular glutamate and generates a dependency on exogenous amino acids.
Figure 12B:
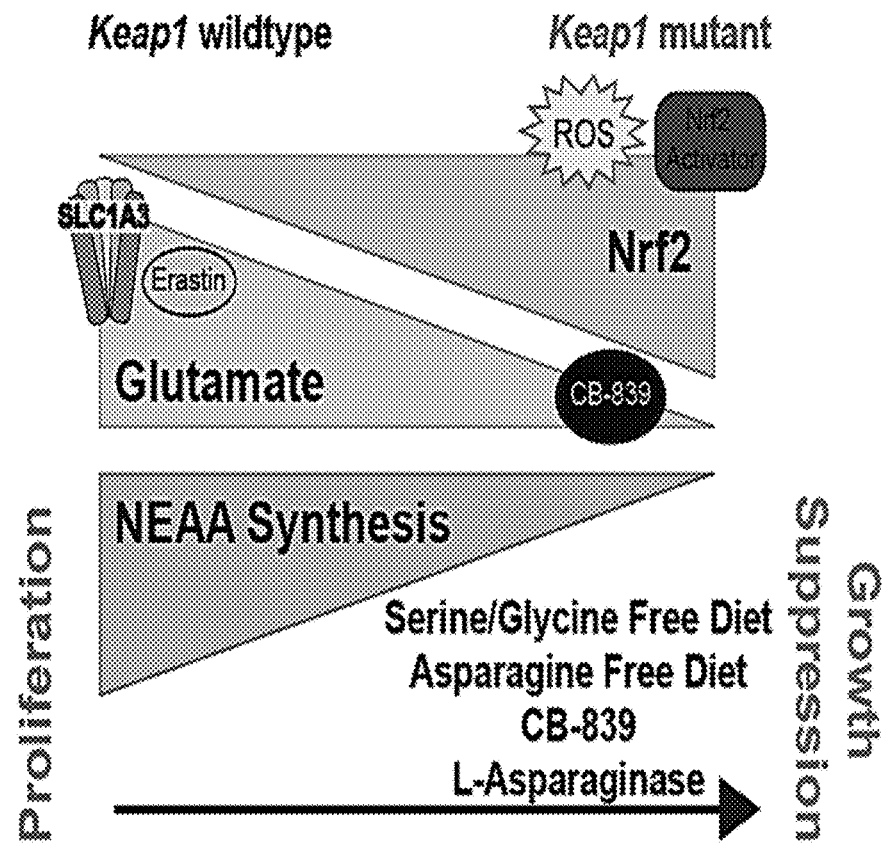

The data uncover a general mechanism in which a specific genotype, renders cells dependent on multiple exogenous NEAAs including serine, glycine and asparagine (FIG. 12). This dependency on exogenous NEAAs can be therapeutically targeted by dietary or enzymatic depletion of specific amino acids to blunt tumor growth (FIG. 12). Using the pre-clinical models, the data show that dietary restriction of asparagine can lead suppression of Keap1 mutant tumor growth (FIG. 9B). Importantly, well-established metabolic therapy currently used for Acute Lymphoblastic Leukemia, L-Asparaginase, is repurposed for the treatment of Keap1 mutant lung cancer. This work supports that metabolite restriction through pharmacological or dietary means can effectively suppress tumor growth. Moving forward, combination of dietary modification with standard of care chemotherapeutics may improve patient response. Additionally, based on these findings, modulation of intracellular glutamate levels through pharmacological intervention may be used to sensitize KRAS driven NSCLC to NEAA depletion, independent of Keap1 status and may be a broadly applicable therapeutic strategy in other cancer subtypes.

Example 2: Identification of Additional Therapeutic Targets

FIGS. 13-30 provide data demonstrating that inhibiting the PPP or sorbitol pathways have a synergetic effect with inhibition of Keap1. Therefore, proteins in the PPP and sorbitol pathways can serve as additional therapeutic targets alone, or in combination with inhibition of Keap1, increasing ROS, or amino acid restriction.

For these experiments:
KP: $Kras^{G12D/+}$; $p53^{-/-}$ mouse lung cancer cell line (Keap1 wt, named as KP)
KP+KI: KP cells treated with KI696, NRF2 activator, at least two weeks (NRF2 activator, named as KI)
KPKJ: KP cells with Keap1 knocked out
KPKJ Vector: KPKJ cells overexpressing vector (Keap1 knockout, named as KO)
KPKJ wt: KPKJ cells overexpressing Keap1 wt cDNA (Keap1 wt, named as KO+Keap1).

Inhibition of KEAP1 and G6PD has synergy lethality in mouse lung adenocarcinoma (FIG. 13) and in human lung adenocarcinoma (FIGS. 14-16).

G6PD is the rate-limiting enzyme of the pentose phosphate pathway (PPP) (FIG. 17). Pyruvate, a-KG and glutamate can rescue G6PD KO cells (FIG. 18). FIG. 19 shows the results of a G6PD shRNA model.

FIG. 20 shows the quantification of cell ROS level in KPKJ wt (Keap1 wildtype) and KPKJ V (Keap1 KO) cells expressing shRFP (control) or shG6pd.

FIG. 21 shows a western blot analysis of KPKJ wt cells inducible expressing Vector (control), cytoplasma TPNOX or mitochondria TPNOX.

FIG. 22 and FIG. 23 show that NADPH depletion affects cell growth.

The polyol pathway is also connected with Keap1 and the PPP pathway (FIG. 24). Akr1b1/Akr1b8/Sord/Cherbp are NRF2 substrates (FIG. 25). KEAP1 mutants are sensitive to polyol enzymes KO (FIG. 26).

FIG. 27 shows a mass isotopomer analysis of sorbitol pool-size in KP (Keap1wildtype), KP+KI (NRF2 activator), KPKJ wt (Keap1 wildtype) and KPKJ V (Keap1 KO) cells expressing sgTOM or sgG6PD. FIG. 28 shows a mass isotopomer analysis of sorbitol labeling percentage in KP (Keap1 wildtype), KP+KI (NRF2 activator), KPKJ wt (Keap1 wildtype) and KPKJ V (Keap1 KO) cells expressing sgTOM or sgG6PD. FIG. 29 shows a mass isotopomer analysis of sorbitol pool-size and labeling percentage in KPKJ wt (Keap1 wildtype) and KPKJ V (Keap1 KO) cells expressing sgTOM or sgAkr1b1/1b7/1b8/1b10. FIG. 30 shows a mass isotopomer analysis of sorbitol pool-size and labeling percentage in H1299 (Keap1 wildtype) and A549 (Keap1 KO) cells expressing sgTOM or sgAKR1B1/1B10/1B15.

Example 3: Identification of Additional Therapeutic Targets

FIGS. 31-39 provide data demonstrating that inhibition of heme biosynthesis genes are synthetic lethal in Keap1-mutant and Nrf2-activated KP LUAD cells.

FIG. 31 shows the general experimental work schematic used for experiments to detect additional therapeutic targets. ~200 genes targeted, with 5 guides per gene. Targets represent broad sampling of metabolic pathways (low representation from each pathway). Heme biosynthesis genes Cpox and Hmbs were identified as candidate targets (FIG. 32 and FIG. 33). Keap1-mutant cells are more sensitive to heme pathway inhibition in a competitive growth assay (FIG. 34). Dominant negative Keap1 alleles further sensitize Keap1 mutant cells to heme synthesis inhibition (FIG. 35).

Keap1-mutant cells require higher levels of exogenous heme to rescue growth (FIG. 36), which supports the notion that increased levels of heme cause an increase in hmox1-dependent heme degradation and a decrease in alas1-dependent heme synthesis.

Keap1-mutant cells also show increased sensitivity to Alas1 knock-down/out (FIG. 37 and FIG. 38).

Based on these results, it has been demonstrated that the Keap1/Nrf2 signaling axis influences heme metabolism, and further that the heme biosynthesis pathway can function as an additional therapeutic target.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating or preventing tumor growth or metastasis in a subject in need thereof, the method comprising:
   a) detecting at least one selected from the group consisting of a decreased level of Keap1 activity, and an inactivating mutation of Keap1, in the tumor; and
   b) administering to the subject a composition, or treatment regimen, selected from the group consisting of:
      i) an agent or treatment regimen for reducing the level of at least one amino acid comprising at least one selected from the group consisting of an asparaginase, a serine degrading enzyme, an inhibitor of phosphoserine aminotransferase, an inhibitor of an amino acid transporter, wherein the amino acid is selected from the group consisting of glutamate, glutamine, proline, serine, alanine, glycine, arginine, lysine, asparagine, methionine, threonine, and isoleucine, an inhibitor of glutaminase (GLS), an inhibitor of glutamate dehydrogenase (GLUD), an aminotransferase inhibitor, and a competitive inhibitor of glutamine;
      ii) an agent for inhibiting the pentose phosphate pathway (PPP) comprising an inhibitor of at least one selected from the group consisting of glucose-6-phosphate dehydrogenase (G6PD or G6PDH), 6-phosphogluconolactonase, 6-phosphogluconate dehydrogenase, fructose-bisphosphate aldolase B, ribose-5-phosphate isomerase, Ribulose 5-Phosphate 3-Epimerase, transaldolase, solute carrier family 16 member 1 (SLC16A1 or MCT1) and lactate dehydrogenase A (LDHA);
      iii) an agent for inhibiting the sorbitol pathway comprising an inhibitor of at least one selected from the group consisting of sorbitol dehydrogenase (SORD), ketohexokinase, Triokinase and FMN Cyclase (TKFC), aldo-keto reductase family 1, member B1 (AKR1b1), aldo-keto reductase family 1, member B3 (AKR1b3), aldo-keto reductase family 1, member B7 (AKR1b7), aldo-keto reductase family 1, member B8 (AKR1b8), aldo-keto reductase family 1, member B10 (AKR1b10), sterol regulatory element binding protein-1c (SREBP-1c), Carbohydrate-responsive element-binding protein (ChREBP), fructose transporter solute carrier family 2 member 5 (SLC2A5 or GLUT5), solute carrier family 16 member 1 (SLC16A1 or MCT1) or lactate dehydrogenase A (LDHA); and
      iv) an agent for inhibiting the heme biosynthesis pathway comprising an inhibitor of at least one selected from the group consisting of 5-aminolevulinic acid synthase-1 (ALAS1), delta-aminolevulinic acid dehydratase (ALAD), hydroxymethylbilane synthase (HMBS), uroporphyrinogen III synthase (UROS), uroporphyrinogen decarboxylase (UROD), coproporphyrinogen oxidase (CPOX), protoporphyrinogen oxidase (PPOX), transmembrane protein 14C (TMEM14C), FLVCR heme transporter 1 (FLVCR1), solute carrier family 48 member 1 (SLC48A1) or ferrochelatase (FECH).

2. The method of claim 1, wherein the composition comprises at least one selected from the group consisting of a chemical compound, a protein, a peptide, a peptidomemetic, an antibody, a ribozyme, a small molecule chemical compound, a nucleic acid, a vector, and an antisense nucleic acid molecule.

* * * * *